(12) United States Patent  
Argenta et al.

(10) Patent No.: US 8,834,520 B2  
(45) Date of Patent: *Sep. 16, 2014

(54) DEVICES AND METHODS FOR TREATING SPINAL CORD TISSUE

(75) Inventors: Louis C. Argenta, Winston-Salem, NC (US); David L. Carroll, Winston-Salem, NC (US); Nicole H. Levi, Winston-Salem, NC (US); Jie Liu, Woodbury, MN (US); Michael J. Morykwas, Winston-Salem, NC (US); Stephen Tatter, Winston-Salem, NC (US); William D. Wagner, Clemmons, NC (US)

(73) Assignee: Wake Forest University, Winston-Salem, NC (US)

( * ) Notice: Subject to any disclaimer, the term of this patent is extended or adjusted under 35 U.S.C. 154(b) by 1170 days.

This patent is subject to a terminal disclaimer.

(21) Appl. No.: 12/248,346

(22) Filed: Oct. 9, 2008

(65) Prior Publication Data

US 2009/0187259 A1 Jul. 23, 2009

Related U.S. Application Data

(60) Provisional application No. 60/978,884, filed on Oct. 10, 2007, provisional application No. 61/081,997, filed on Jul. 18, 2008, provisional application No. 61/088,558, filed on Aug. 13, 2008.

(51) Int. Cl.
*A61B 17/08* (2006.01)

(52) U.S. Cl.
USPC .......................................... 606/215; 606/213

(58) Field of Classification Search
USPC .................................. 604/213, 215; 424/423
See application file for complete search history.

(56) References Cited

U.S. PATENT DOCUMENTS

| 774,529 | A | 11/1904 | Nieschang |
| 1,000,001 | A | 8/1911 | Holz |
| 1,355,679 | A | 10/1920 | McConnell |
| 1,355,846 | A | 10/1920 | Rannells |
| 1,385,346 | A | 7/1921 | Taylor |
| 1,936,129 | A | 11/1933 | Fisk |
| 2,025,492 | A | 12/1935 | Aird |
| 2,122,121 | A | 6/1938 | Tillotson |

(Continued)

FOREIGN PATENT DOCUMENTS

| AU | 2003231870 | 4/2009 |
| DE | 372727 | 3/1923 |

(Continued)

OTHER PUBLICATIONS

Milner, R.H., et al., "Plasticized polyvinyl chloride film as a primary burns dressing: a microbiological study," Burns, 14(1):62-65 (1988).

(Continued)

*Primary Examiner* — Nicholas Lucchesi
*Assistant Examiner* — Pritesh Patel
(74) *Attorney, Agent, or Firm* — Niels Haun; Dann Dorfman Herrell & Skillman, PC

(57) ABSTRACT

The present invention provides devices and methods that treat damaged spinal cord tissue, such as spinal tissue damaged by disease, infection, or trauma, which may lead to the presence of swelling, compression, and compromised blood flow secondary to interstitial edema.

25 Claims, 8 Drawing Sheets

(56) References Cited

U.S. PATENT DOCUMENTS

| | | | |
|---|---|---|---|
| 2,195,771 | A | 4/1940 | Estler |
| 2,221,758 | A | 11/1940 | Elmquist |
| 2,232,254 | A | 2/1941 | Morgan |
| 2,280,915 | A | 4/1942 | Johnson |
| 2,338,339 | A | 1/1944 | LaMere |
| 2,443,481 | A | 6/1948 | Sene |
| 2,547,758 | A | 4/1951 | Keeling |
| 2,573,791 | A | 11/1951 | Howells |
| 2,577,945 | A | 12/1951 | Atherton |
| 2,632,443 | A | 3/1953 | Lesher |
| 2,682,873 | A | 7/1954 | Evans |
| 2,910,763 | A | 11/1959 | Lauterbach |
| 2,969,057 | A | 1/1961 | Simmons |
| 3,026,874 | A | 3/1962 | Stevens |
| 3,042,041 | A | 7/1962 | Jascalevich |
| 3,115,138 | A | 12/1963 | McElvenny |
| 3,315,665 | A | 4/1967 | MacLeod |
| 3,324,855 | A | 6/1967 | Heimlich |
| 3,367,332 | A | 2/1968 | Groves |
| 3,382,867 | A | 5/1968 | Reaves |
| 3,429,313 | A | 2/1969 | Romanelli |
| 3,486,504 | A | 12/1969 | Austin, Jr. |
| 3,520,300 | A | 7/1970 | Flower et al. |
| 3,528,416 | A | 9/1970 | Chamberlain |
| 3,568,675 | A | 3/1971 | Harvey |
| 3,572,340 | A | 3/1971 | Lloyd et al. |
| 3,610,238 | A | 10/1971 | Rich, Jr. |
| 3,648,692 | A | 3/1972 | Wheeler |
| 3,682,180 | A | 8/1972 | McFarlane |
| 3,713,622 | A | 1/1973 | Dinger |
| 3,753,439 | A | 8/1973 | Brugarolas et al. |
| 3,782,377 | A | 1/1974 | Rychlik |
| 3,782,387 | A | 1/1974 | Falabella |
| 3,812,972 | A | 5/1974 | Rosenblum |
| 3,814,095 | A | 6/1974 | Lubens |
| 3,826,254 | A | 7/1974 | Mellor |
| 3,874,387 | A | 4/1975 | Barbieri |
| 3,896,810 | A | 7/1975 | Akiyama |
| 3,903,882 | A | 9/1975 | Augurt |
| 3,908,664 | A | 9/1975 | Loseff |
| 3,935,863 | A | 2/1976 | Kliger |
| 3,938,540 | A | 2/1976 | Holbrook et al. |
| 3,954,105 | A | 5/1976 | Nordby et al. |
| 3,975,567 | A | 8/1976 | Lock |
| 3,978,855 | A | 9/1976 | McRae et al. |
| 3,992,725 | A | 11/1976 | Homsy |
| 3,993,080 | A | 11/1976 | Loseff |
| 3,998,227 | A | 12/1976 | Holbrook et al. |
| RE29,319 | E | 7/1977 | Nordby et al. |
| 4,080,970 | A | 3/1978 | Miller |
| 4,112,947 | A | 9/1978 | Nehring |
| 4,139,004 | A | 2/1979 | Gonzalez, Jr. |
| 4,149,541 | A | 4/1979 | Gammons et al. |
| 4,156,066 | A | 5/1979 | Gould |
| 4,169,563 | A | 10/1979 | Leu |
| 4,184,510 | A | 1/1980 | Murry et al. |
| 4,187,852 | A | 2/1980 | Urry et al. |
| 4,191,204 | A | 3/1980 | Nehring |
| 4,221,215 | A | 9/1980 | Mandelbaum |
| 4,224,941 | A | 9/1980 | Stivala |
| 4,224,945 | A | 9/1980 | Cohen |
| 4,250,882 | A | 2/1981 | Adair |
| 4,256,109 | A | 3/1981 | Nichols |
| 4,261,363 | A | 4/1981 | Russo |
| 4,275,721 | A | 6/1981 | Olson |
| 4,297,995 | A | 11/1981 | Golub |
| 4,341,209 | A | 7/1982 | Schaar |
| 4,373,519 | A | 2/1983 | Errede et al. |
| 4,382,441 | A | 5/1983 | Svedman |
| 4,392,853 | A | 7/1983 | Muto |
| 4,399,816 | A | 8/1983 | Spangler |
| 4,419,097 | A | 12/1983 | Rowland |
| 4,452,845 | A | 6/1984 | Lloyd et al. |
| 4,457,755 | A | 7/1984 | Wilson |
| 4,459,139 | A | 7/1984 | vonReis et al. |
| 4,465,062 | A | 8/1984 | Versaggi et al. |
| 4,465,485 | A | 8/1984 | Kashmer et al. |
| 4,475,909 | A | 10/1984 | Eisenberg |
| 4,480,638 | A | 11/1984 | Schmid |
| 4,499,896 | A | 2/1985 | Heinecke |
| RE31,887 | E | 5/1985 | Hodgson |
| 4,525,166 | A | 6/1985 | Leclerc |
| 4,533,352 | A | 8/1985 | Van Beek |
| 4,540,412 | A | 9/1985 | Van Overloop |
| 4,543,100 | A | 9/1985 | Brodsky |
| 4,553,967 | A | 11/1985 | Ferguson |
| 4,569,674 | A | 2/1986 | Phillips et al. |
| 4,573,965 | A | 3/1986 | Russo |
| 4,579,555 | A | 4/1986 | Russo |
| 4,605,399 | A | 8/1986 | Weston et al. |
| 4,608,041 | A | 8/1986 | Nielsen |
| 4,624,656 | A | 11/1986 | Clark et al. |
| 4,627,427 | A | 12/1986 | Arco |
| 4,633,863 | A | 1/1987 | Filips |
| 4,637,819 | A | 1/1987 | Ouellette |
| 4,640,688 | A | 2/1987 | Hauser |
| 4,641,643 | A | 2/1987 | Greer |
| 4,655,754 | A | 4/1987 | Richmond et al. |
| 4,661,093 | A | 4/1987 | Beck et al. |
| 4,664,652 | A | 5/1987 | Weilbacher |
| 4,664,662 | A | 5/1987 | Webster |
| 4,667,666 | A | 5/1987 | Fryslie |
| 4,679,590 | A | 7/1987 | Hergenroeder |
| 4,710,165 | A | 12/1987 | McNeil et al. |
| 4,713,052 | A | 12/1987 | Beck |
| 4,717,382 | A | 1/1988 | Clemens et al. |
| 4,733,659 | A | 3/1988 | Edenbaum |
| 4,743,232 | A | 5/1988 | Kruger |
| 4,747,166 | A | 5/1988 | Kuntz |
| 4,753,231 | A | 6/1988 | Lang et al. |
| 4,753,232 | A | 6/1988 | Ward |
| 4,759,354 | A | 7/1988 | Quarfoot |
| 4,764,167 | A | 8/1988 | Tu |
| 4,773,409 | A | 9/1988 | Cilento et al. |
| 4,778,446 | A | 10/1988 | Jensen |
| 4,778,456 | A | 10/1988 | Lokken |
| 4,820,265 | A | 4/1989 | DeSatnick et al. |
| 4,820,284 | A | 4/1989 | Hauri |
| 4,822,278 | A | 4/1989 | Oliva |
| 4,834,110 | A | 5/1989 | Richard |
| 4,836,192 | A | 6/1989 | Abbate |
| 4,838,883 | A | 6/1989 | Matsuura |
| 4,840,187 | A | 6/1989 | Brazier |
| 4,841,962 | A | 6/1989 | Berg et al. |
| 4,851,545 | A | 7/1989 | Song et al. |
| 4,860,737 | A | 8/1989 | Lang et al. |
| 4,863,449 | A | 9/1989 | Therriault |
| 4,872,450 | A | 10/1989 | Austad |
| 4,875,473 | A | 10/1989 | Alvarez |
| 4,878,901 | A | 11/1989 | Sachse |
| 4,890,608 | A | 1/1990 | Steer |
| 4,897,081 | A | 1/1990 | Poirier |
| 4,906,233 | A | 3/1990 | Moriuchi et al. |
| 4,906,240 | A | 3/1990 | Reed |
| 4,917,112 | A | 4/1990 | Kalt |
| 4,921,492 | A | 5/1990 | Schultz et al. |
| 4,925,447 | A | 5/1990 | Rosenblatt |
| 4,931,519 | A | 6/1990 | Song et al. |
| 4,941,882 | A | 7/1990 | Ward et al. |
| 4,953,565 | A | 9/1990 | Tachibana et al. |
| 4,969,880 | A | 11/1990 | Zamierowski |
| 4,969,881 | A | 11/1990 | Viesturs |
| 4,988,336 | A | 1/1991 | Kohn |
| 4,990,144 | A | 2/1991 | Blott |
| 4,991,574 | A | 2/1991 | Pocknell |
| 4,997,425 | A | 3/1991 | Shioya |
| 5,002,528 | A | 3/1991 | Palestrant |
| 5,002,529 | A | 3/1991 | Cunningham |
| 5,003,971 | A | 4/1991 | Buckley |
| 5,014,389 | A | 5/1991 | Ogilvie |
| 5,019,086 | A | 5/1991 | Neward |
| 5,024,841 | A | 6/1991 | Chu et al. |
| 5,034,006 | A | 7/1991 | Hosoda |
| 5,035,884 | A | 7/1991 | Song et al. |

(56) References Cited

U.S. PATENT DOCUMENTS

| | | |
|---|---|---|
| 5,042,978 A | 8/1991 | Quenin |
| 5,060,662 A | 10/1991 | Farnswoth, III |
| 5,071,403 A | 12/1991 | Larason |
| 5,073,172 A | 12/1991 | Fell |
| 5,086,763 A | 2/1992 | Hathman |
| 5,086,764 A | 2/1992 | Gilman |
| 5,100,396 A | 3/1992 | Zamierowski |
| 5,101,808 A | 4/1992 | Kobayashi |
| 5,106,362 A | 4/1992 | Gilman |
| 5,106,629 A | 4/1992 | Cartmell |
| 5,113,871 A | 5/1992 | Viljanto et al. |
| 5,135,518 A | 8/1992 | Vera |
| 5,147,338 A | 9/1992 | Lang |
| 5,149,331 A | 9/1992 | Ferdman et al. |
| 5,152,757 A | 10/1992 | Eriksson |
| 5,160,322 A | 11/1992 | Scheremet |
| 5,167,613 A | 12/1992 | Karami |
| 5,170,781 A | 12/1992 | Loomis |
| 5,176,663 A | 1/1993 | Svedman |
| 5,176,667 A | 1/1993 | DeBring |
| 5,192,282 A | 3/1993 | Draenert |
| 5,215,539 A | 6/1993 | Schoolman |
| 5,224,947 A | 7/1993 | Cooper |
| 5,230,350 A | 7/1993 | Fentress |
| 5,261,893 A | 11/1993 | Zamierowski |
| 5,263,922 A | 11/1993 | Sova |
| 5,298,015 A | 3/1994 | Komatsuzaki |
| 5,330,452 A | 7/1994 | Zook |
| 5,344,415 A | 9/1994 | DeBusk |
| 5,349,965 A | 9/1994 | McCarver |
| 5,358,494 A | 10/1994 | Svedman |
| 5,376,252 A | 12/1994 | Ekstrom |
| 5,395,315 A | 3/1995 | Griep |
| 5,419,768 A | 5/1995 | Kayser |
| 5,431,662 A | 7/1995 | Nicholas |
| 5,437,651 A | 8/1995 | Todd |
| 5,445,604 A | 8/1995 | Lang |
| 5,447,492 A | 9/1995 | Cartmell et al. |
| 5,451,215 A | 9/1995 | Wolter |
| 5,456,267 A | 10/1995 | Stark |
| 5,478,333 A | 12/1995 | Asherman, Jr. |
| 5,484,399 A | 1/1996 | DiResta et al. |
| 5,484,427 A | 1/1996 | Gibbons |
| 5,487,889 A | 1/1996 | Eckert |
| 5,490,962 A | 2/1996 | Cima et al. |
| 5,496,262 A | 3/1996 | Johnson, Jr. |
| 5,520,652 A | 5/1996 | Peterson |
| 5,522,901 A | 6/1996 | Thomas et al. |
| 5,527,293 A | 6/1996 | Zamierowski |
| 5,531,670 A | 7/1996 | Westby |
| 5,542,918 A | 8/1996 | Atkinson |
| 5,549,584 A | 8/1996 | Gross |
| 5,556,375 A | 9/1996 | Ewall |
| 5,578,022 A | 11/1996 | Scherson |
| 5,580,353 A | 12/1996 | Mendes et al. |
| 5,588,955 A | 12/1996 | Johnson, Jr. |
| 5,599,330 A | 2/1997 | Rainin |
| 5,607,388 A | 3/1997 | Ewall |
| 5,628,735 A | 5/1997 | Skow |
| 5,636,643 A | 6/1997 | Argenta et al. |
| 5,645,081 A | 7/1997 | Argenta et al. |
| 5,655,258 A | 8/1997 | Heintz |
| 5,656,027 A | 8/1997 | Ellingboe |
| 5,662,598 A | 9/1997 | Tobin |
| 5,662,624 A | 9/1997 | Sundstrom |
| 5,662,625 A | 9/1997 | Westwood |
| 5,678,564 A | 10/1997 | Lawrence |
| 5,697,920 A | 12/1997 | Gibbons |
| 5,716,360 A | 2/1998 | Baldwin et al. |
| 5,717,005 A | 2/1998 | Richardson |
| 5,717,030 A | 2/1998 | Dunn |
| 5,720,720 A | 2/1998 | Laske |
| 5,733,884 A | 3/1998 | Barbul |
| 5,735,833 A | 4/1998 | Olson |
| 5,736,372 A | 4/1998 | Vacanti et al. |
| 5,738,686 A | 4/1998 | Kubein-Messenburg et al. |
| 5,743,912 A | 4/1998 | Lahille et al. |
| 5,762,640 A | 6/1998 | Kajiwara |
| 5,766,618 A | 6/1998 | Laurencin et al. |
| 5,782,871 A | 7/1998 | Fujiwara |
| 5,810,840 A | 9/1998 | Lindsay |
| 5,817,145 A | 10/1998 | Augustine |
| 5,827,246 A | 10/1998 | Bowen |
| 5,869,080 A | 2/1999 | McGregor et al. |
| 5,876,359 A | 3/1999 | Bock et al. |
| 5,911,222 A | 6/1999 | Lawrence |
| 5,919,476 A | 7/1999 | Fischer |
| 5,921,972 A | 7/1999 | Skow |
| 5,928,174 A | 7/1999 | Gibbins |
| 5,935,136 A | 8/1999 | Hulse et al. |
| 5,941,859 A | 8/1999 | Lerman |
| 5,947,914 A | 9/1999 | Augustine |
| 5,951,295 A | 9/1999 | Lyles et al. |
| 5,954,680 A | 9/1999 | Augustine |
| 5,958,314 A | 9/1999 | Draenert |
| 5,961,480 A | 10/1999 | Augustine |
| 5,964,721 A | 10/1999 | Augustine |
| 5,964,723 A | 10/1999 | Augustine |
| 5,964,733 A | 10/1999 | Laabs et al. |
| 5,968,047 A | 10/1999 | Reed |
| 5,986,163 A | 11/1999 | Augustine |
| 6,010,527 A | 1/2000 | Augustine |
| 6,045,518 A | 4/2000 | Augustine |
| 6,045,541 A | 4/2000 | Matsumoto |
| 6,051,016 A | 4/2000 | Mesaros et al. |
| 6,053,416 A | 4/2000 | Specht |
| 6,071,254 A | 6/2000 | Augustine |
| 6,071,267 A | 6/2000 | Zamierowski |
| 6,071,304 A | 6/2000 | Augustine |
| 6,080,189 A | 6/2000 | Augustine |
| 6,080,243 A | 6/2000 | Insley |
| 6,086,587 A | 7/2000 | Hawk |
| 6,087,553 A | 7/2000 | Cohen et al. |
| 6,093,160 A | 7/2000 | Augustine |
| 6,095,148 A | 8/2000 | Shastri |
| 6,095,992 A | 8/2000 | Augustine |
| 6,106,913 A | 8/2000 | Scardino et al. |
| 6,110,197 A | 8/2000 | Augustine |
| 6,113,561 A | 9/2000 | Augustine |
| 6,117,111 A | 9/2000 | Fleischmann |
| 6,135,116 A | 10/2000 | Vogel |
| 6,142,982 A | 11/2000 | Hunt |
| 6,143,945 A | 11/2000 | Augustine |
| 6,146,423 A | 11/2000 | Cohen et al. |
| 6,159,246 A | 12/2000 | Mendes et al. |
| 6,174,306 B1 | 1/2001 | Fleischmann |
| 6,187,047 B1 | 2/2001 | Kwan et al. |
| 6,190,391 B1 | 2/2001 | Stubbs |
| 6,203,563 B1 | 3/2001 | Fernandez |
| 6,207,875 B1 | 3/2001 | Lindqvist |
| 6,213,965 B1 | 4/2001 | Augustine |
| 6,213,966 B1 | 4/2001 | Augustine |
| 6,217,535 B1 | 4/2001 | Augustine |
| 6,235,009 B1 | 5/2001 | Skow |
| 6,235,047 B1 | 5/2001 | Augustine |
| 6,241,697 B1 | 6/2001 | Augustine |
| 6,241,698 B1 | 6/2001 | Augustine |
| 6,248,084 B1 | 6/2001 | Augustine |
| 6,254,557 B1 | 7/2001 | Augustine |
| 6,254,580 B1 | 7/2001 | Svedman |
| 6,264,622 B1 | 7/2001 | Augustine |
| 6,264,979 B1 | 7/2001 | Svedman |
| 6,267,740 B1 | 7/2001 | Augustine |
| 6,283,931 B1 | 9/2001 | Augustine |
| 6,284,941 B1 | 9/2001 | Cox |
| 6,290,685 B1 | 9/2001 | Insley |
| 6,293,917 B1 | 9/2001 | Augustine |
| 6,323,146 B1 | 11/2001 | Pugh |
| 6,325,788 B1 | 12/2001 | McKay |
| 6,344,061 B1 | 2/2002 | Leitao et al. |
| 6,345,623 B1 | 2/2002 | Heaton et al. |
| 6,355,215 B1 | 3/2002 | Poggie et al. |
| 6,359,189 B1 | 3/2002 | Fleischmann |
| 6,377,653 B1 | 4/2002 | Lee et al. |

(56) References Cited

U.S. PATENT DOCUMENTS

| | | |
|---|---|---|
| 6,394,948 B1 | 5/2002 | Borst et al. |
| 6,398,767 B1 | 6/2002 | Fleischmann |
| 6,430,427 B1 | 8/2002 | Lee et al. |
| 6,458,109 B1 | 10/2002 | Henley |
| 6,484,716 B1 | 11/2002 | Leininger |
| 6,485,503 B2 | 11/2002 | Jacobs et al. |
| 6,488,643 B1 | 12/2002 | Tumey |
| 6,491,693 B1 | 12/2002 | Lytinas |
| 6,520,982 B1 | 2/2003 | Boynton |
| 6,551,317 B2 | 4/2003 | Berish et al. |
| 6,553,998 B2 | 4/2003 | Heaton et al. |
| 6,555,729 B1 | 4/2003 | Fleischmann |
| 6,641,604 B1 | 11/2003 | Adelman |
| 6,648,862 B2 | 11/2003 | Watson |
| 6,663,349 B1 | 12/2003 | Discenzo |
| 6,673,028 B1 | 1/2004 | Argenta et al. |
| 6,682,491 B2 | 1/2004 | Johnson |
| 6,685,681 B2 | 2/2004 | Lockwood |
| 6,695,823 B1 | 2/2004 | Lina |
| 6,712,851 B1 | 3/2004 | Lemperle et al. |
| 6,749,592 B2 | 6/2004 | Lord |
| 6,752,794 B2 | 6/2004 | Lockwood |
| 6,755,807 B2 | 6/2004 | Risk, Jr. |
| 765,746 A1 | 7/2004 | Miner |
| 6,764,462 B2 | 7/2004 | Risk, Jr. |
| 6,767,334 B1 | 7/2004 | Randolph |
| 6,770,794 B2 | 8/2004 | Fleischmann |
| 6,793,633 B2 | 9/2004 | Douglas et al. |
| 6,800,074 B2 | 10/2004 | Henley |
| 6,814,079 B2 | 11/2004 | Heaton et al. |
| 6,824,533 B2 | 11/2004 | Risk, Jr. |
| 6,840,960 B2 | 1/2005 | Bubb |
| 6,855,135 B2 | 2/2005 | Lockwood |
| 6,856,821 B2 | 2/2005 | Johnson |
| 6,878,119 B2 | 4/2005 | Johnson |
| 6,887,246 B2 | 5/2005 | Bhatnagar et al. |
| 6,936,037 B2 | 8/2005 | Bubb |
| 6,951,553 B2 | 10/2005 | Bubb |
| 6,988,423 B2 | 1/2006 | Bolam |
| 6,994,702 B1 | 2/2006 | Johnson |
| 7,004,915 B2 | 2/2006 | Boynton |
| 7,022,113 B2 | 4/2006 | Lockwood |
| 7,066,960 B1 | 6/2006 | Dickman |
| 7,070,584 B2 | 7/2006 | Johnson |
| 7,077,832 B2 | 7/2006 | Fleischmann |
| 7,108,683 B2 | 9/2006 | Zamierowski |
| 7,117,869 B2 | 10/2006 | Heaton |
| 7,128,735 B2 | 10/2006 | Weston |
| 7,144,390 B1 | 12/2006 | Hannigan |
| 7,169,151 B1 | 1/2007 | Lytinas |
| 843,674 A1 | 2/2007 | Funk |
| 7,175,625 B2 | 2/2007 | Culbert |
| 7,198,046 B1 | 4/2007 | Argenta |
| 7,216,651 B2 | 5/2007 | Argenta |
| 7,276,051 B1 | 10/2007 | Henley et al. |
| 7,279,612 B1 | 10/2007 | Heaton et al. |
| 7,722,894 B2 | 5/2010 | Wang et al. |
| 7,931,651 B2 | 4/2011 | Webb et al. |
| 8,267,960 B2 * | 9/2012 | Argenta et al. ............ 606/215 |
| 2001/0029956 A1 | 10/2001 | Argenta et al. |
| 2001/0043943 A1 | 11/2001 | Coffey |
| 2002/0065494 A1 | 5/2002 | Lockwood et al. |
| 2002/0082567 A1 | 6/2002 | Lockwood et al. |
| 2002/0115952 A1 | 8/2002 | Johnson et al. |
| 2002/0120185 A1 | 8/2002 | Johnson |
| 2002/0143286 A1 | 10/2002 | Tumey |
| 2002/0143403 A1 | 10/2002 | Vaidyanathan et al. |
| 2002/0161317 A1 | 10/2002 | Risk et al. |
| 2002/0161346 A1 | 10/2002 | Lockwood et al. |
| 2002/0198503 A1 | 12/2002 | Risk, Jr. et al. |
| 2002/0198504 A1 | 12/2002 | Risk, Jr. et al. |
| 2003/0040687 A1 | 2/2003 | Boynton |
| 2003/0050594 A1 | 3/2003 | Zamierowski |
| 2003/0108587 A1 | 6/2003 | Orgill et al. |
| 2003/0109855 A1 | 6/2003 | Solem et al. |
| 2003/0118692 A1 | 6/2003 | Wang et al. |
| 2003/0130599 A1 | 7/2003 | Restle et al. |
| 2003/0187367 A1 | 10/2003 | Odland |
| 2003/0208149 A1 | 11/2003 | Coffey |
| 2003/0219469 A1 | 11/2003 | Johnson |
| 2003/0225347 A1 | 12/2003 | Argenta |
| 2003/0225441 A1 | 12/2003 | Boynton |
| 2004/0006319 A1 | 1/2004 | Lina |
| 2004/0024351 A1 | 2/2004 | Greter |
| 2004/0030304 A1 | 2/2004 | Hunt |
| 2004/0039391 A1 | 2/2004 | Argenta |
| 2004/0039415 A1 | 2/2004 | Zamierowski |
| 2004/0064111 A1 | 4/2004 | Lockwood et al. |
| 2004/0064132 A1 | 4/2004 | Boehringer |
| 2004/0073151 A1 | 4/2004 | Weston |
| 2004/0122434 A1 | 6/2004 | Argenta |
| 2004/0127845 A1 | 7/2004 | Renz et al. |
| 2004/0167482 A1 | 8/2004 | Watson |
| 2004/0225178 A1 | 11/2004 | Kriewall |
| 2004/0225208 A1 | 11/2004 | Johnson |
| 2004/0249353 A1 | 12/2004 | Risks, Jr. et al. |
| 2004/0260230 A1 | 12/2004 | Randolph |
| 2005/0020955 A1 | 1/2005 | Sanders |
| 2005/0028828 A1 | 2/2005 | Heaton et al. |
| 2005/0043659 A1 | 2/2005 | Challis et al. |
| 2005/0063939 A1 | 3/2005 | Ameer et al. |
| 2005/0065484 A1 | 3/2005 | Watson, Jr. |
| 2005/0090787 A1 | 4/2005 | Risk, Jr. et al. |
| 2005/0101940 A1 | 5/2005 | Radl |
| 2005/0124966 A1 | 6/2005 | Karpowicz |
| 2005/0131327 A1 | 6/2005 | Lockwood et al. |
| 2005/0148913 A1 | 7/2005 | Weston |
| 2005/0165350 A1 | 7/2005 | Greter |
| 2005/0177190 A1 | 8/2005 | Zamierowski |
| 2005/0182445 A1 | 8/2005 | Zamierowski |
| 2005/0197645 A1 | 9/2005 | Karpowicz |
| 2005/0203452 A1 | 9/2005 | Weston |
| 2005/0209574 A1 | 9/2005 | Boehringer |
| 2005/0222527 A1 | 10/2005 | Miller |
| 2005/0222528 A1 | 10/2005 | Weston |
| 2005/0222544 A1 | 10/2005 | Weston |
| 2005/0228329 A1 | 10/2005 | Boehringer |
| 2005/0234510 A1 | 10/2005 | Zamierowski |
| 2005/0240220 A1 | 10/2005 | Zamierowski |
| 2005/0261615 A1 | 11/2005 | Weston |
| 2005/0261642 A1 | 11/2005 | Weston |
| 2005/0283105 A1 | 12/2005 | Heaton et al. |
| 2006/0025727 A1 | 2/2006 | Boehringer |
| 2006/0029650 A1 | 2/2006 | Coffey |
| 2006/0029675 A1 | 2/2006 | Ginther |
| 2006/0079852 A1 | 4/2006 | Bubb |
| 2006/0100586 A1 | 5/2006 | Karpowicz |
| 2006/0149170 A1 | 7/2006 | Boynton |
| 2006/0149171 A1 | 7/2006 | Vogel |
| 2006/0149176 A1 | 7/2006 | Bolam |
| 2006/0173253 A1 | 8/2006 | Ganapathy |
| 2006/0189910 A1 | 8/2006 | Johnson |
| 2006/0193888 A1 | 8/2006 | Lye et al. |
| 2006/0213527 A1 | 9/2006 | Argenta et al. |
| 2006/0263417 A1 | 11/2006 | Lelkes et al. |
| 2006/0286076 A1 | 12/2006 | Fleischmann |
| 2006/0293169 A1 | 12/2006 | Srinivasan et al. |
| 2007/0005028 A1 | 1/2007 | Risk, Jr. et al. |
| 2007/0014837 A1 | 1/2007 | Johnson |
| 2007/0021697 A1 | 1/2007 | Ginther |
| 2007/0021698 A1 | 1/2007 | Fleischmann |
| 2007/0032754 A1 | 2/2007 | Walsh |
| 2007/0071790 A1 | 3/2007 | Ameer et al. |
| 2007/0207179 A1 | 9/2007 | Andersen et al. |
| 2007/0208420 A1 | 9/2007 | Ameer et al. |
| 2007/0219585 A1 | 9/2007 | Cornet et al. |
| 2007/0233022 A1 | 10/2007 | Henley et al. |
| 2007/0260226 A1 | 11/2007 | Jaeb et al. |
| 2008/0112998 A1 | 5/2008 | Wang |
| 2008/0208147 A1 | 8/2008 | Argenta et al. |
| 2008/0208171 A1 | 8/2008 | Argenta et al. |
| 2009/0093565 A1 | 4/2009 | Yang et al. |
| 2009/0148945 A1 | 6/2009 | Ameer et al. |
| 2009/0254120 A1 | 10/2009 | Argenta et al. |

(56) References Cited

U.S. PATENT DOCUMENTS

| | | |
|---|---|---|
| 2009/0325859 A1 | 12/2009 | Ameer et al. |
| 2010/0121229 A1* | 5/2010 | Argenta et al. .......... 601/6 |
| 2012/0215235 A1 | 8/2012 | Fogel |

FOREIGN PATENT DOCUMENTS

| | | |
|---|---|---|
| DE | 561757 | 10/1932 |
| DE | 847475 | 6/1952 |
| DE | 847475 | 8/1952 |
| DE | 1963258 | 6/1971 |
| DE | 2809828 | 9/1978 |
| DE | 3102674 | 9/1982 |
| DE | 3539533 | 5/1987 |
| DE | 4037931 | 5/1992 |
| DE | 4111122 | 4/1993 |
| DE | 29504378 | 9/1995 |
| DE | 19722075 | 10/1998 |
| DK | 64055 | 10/1945 |
| EP | 0117632 | 9/1984 |
| EP | 0274898 | 7/1988 |
| EP | 0424165 | 4/1991 |
| EP | 0485657 | 5/1992 |
| EP | 0547496 | 6/1993 |
| EP | 0 620 720 B1 | 10/1994 |
| EP | 0620720 | 10/1994 |
| EP | 0620720 B2 | 10/1994 |
| EP | 0688189 | 12/1995 |
| EP | 0777504 | 6/1997 |
| EP | 0853950 | 7/1998 |
| EP | 0880953 | 12/1998 |
| EP | 1064958 | 1/2001 |
| EP | 1088569 | 4/2001 |
| EP | 1452191 | 9/2004 |
| FR | 500253 | 3/1920 |
| FR | 1303238 | 9/1962 |
| GB | 190203090 | 0/1902 |
| GB | 114754 | 4/1918 |
| GB | 641061 | 8/1950 |
| GB | 1273342 | 5/1972 |
| GB | 1457164 | 12/1976 |
| GB | 1549756 | 8/1979 |
| GB | 2195255 | 4/1988 |
| GB | 2329127 | 3/1999 |
| GB | 2333965 | 8/1999 |
| GB | 2336546 | 10/1999 |
| GB | 2342584 | 4/2000 |
| GB | 2344531 | 6/2000 |
| GB | 0688189 | 9/2000 |
| GB | 2351025 | 12/2000 |
| JP | 1004629 | 1/1989 |
| JP | 06-048860 | 2/1994 |
| RU | 70627 | 2/2008 |
| SE | 84485 | 10/1935 |
| SU | 587941 | 1/1978 |
| SU | 1416108 | 7/1985 |
| SU | 1251912 | 8/1986 |
| SU | 1268175 | 11/1986 |
| WO | 80/01139 | 6/1980 |
| WO | 87/00439 | 1/1987 |
| WO | 87/04626 | 8/1987 |
| WO | WO 89/04158 | 5/1989 |
| WO | 90/00060 | 1/1990 |
| WO | 90/10424 | 9/1990 |
| WO | 9011795 | 10/1990 |
| WO | 9100718 | 1/1991 |
| WO | 9116030 | 10/1991 |
| WO | 9219313 | 11/1992 |
| WO | 9220299 | 11/1992 |
| WO | 93/09727 | 5/1993 |
| WO | 94/00090 | 1/1994 |
| WO | 94/20041 | 9/1994 |
| WO | 96/05873 | 2/1996 |
| WO | 96/15745 | 5/1996 |
| WO | 99/13793 | 3/1999 |
| WO | 99/51164 | 10/1999 |
| WO | 00/07653 | 2/2000 |
| WO | 00/15277 | 3/2000 |
| WO | 00/21586 | 4/2000 |
| WO | 00/26100 | 5/2000 |
| WO | 00/30567 | 6/2000 |
| WO | 00/32247 | 6/2000 |
| WO | 00/38552 | 7/2000 |
| WO | 00/38755 | 7/2000 |
| WO | 00/42958 | 7/2000 |
| WO | 00/59418 | 10/2000 |
| WO | 00/59424 | 10/2000 |
| WO | 00/61206 | 10/2000 |
| WO | 00/64394 | 11/2000 |
| WO | 01/34223 | 5/2001 |
| WO | 01/37922 | 5/2001 |
| WO | 01/49233 | 7/2001 |
| WO | 01/85248 | 11/2001 |
| WO | WO 01/89431 | 11/2001 |
| WO | WO 02/43634 | 6/2002 |
| WO | 03/005943 | 1/2003 |
| WO | 03028786 | 4/2003 |
| WO | 03/101385 | 12/2003 |
| WO | WO 03/101508 | 12/2003 |
| WO | 2005/028017 | 3/2005 |
| WO | 2005/046762 | 5/2005 |
| WO | 2005/102234 | 11/2005 |
| WO | 2006/046060 | 5/2006 |
| WO | 2007106591 | 9/2007 |
| WO | 2008063281 | 5/2008 |
| WO | 2009/049058 | 4/2009 |
| WO | 2009/089435 | 7/2009 |
| WO | 2010009294 | 1/2010 |

OTHER PUBLICATIONS

Wilson, G., et al., "Plasticised polyvinylchloride as a temporary dressing for burns," Br. Med. J., 294:556-557 (Feb. 1987).

Hunsaker, R.H., Correspondence and Brief Communications—"Polyvinylchloride for increasing take of skin grafts," Plast. Reconstr. Surg. 82:193 (Jul. 1988).

Labler, L., et al., "Wound conditioning by vacuum assisted closure (V.A.C.) in postoperative infections after dorsal spine surgery," Eur. Spine J., 15(9):1388-1396 (Sep. 2006).

Yuan-Innes, M.J. et al., "Vacuum-assisted wound closure: a new approach to spinal wounds with exposed hardware,"Spine, 26(3):E1-E4, (6 sheets) (Feb. 2001).

Ploumis, A., et al., "Therapy of spinal wound infections using vacuum-assisted wound closure: risk factors leading to resistance to treatment," J. Spinal Disord. Tech., 21(5):320-323 (Jul. 2008).

Tauro, L.F., et al., "A comparative study of the efficacy of topical negative pressure moist dressings and conventional moist dressings in chronic wounds," Indian J. Plast. Surg. 40(2):133-140 (Jul.-Dec. 2007).

Kuznetsov, V.A., et al., Report on Practical Application entitled "Method of vacuum-sorption treatment of purulent wounds," Kazan Municipal Hospital No. 8, (1 sheet in English, 1 sheet in Russian and certificate of translation dated Apr. 28, 2009), (allegedly dated May 19, 1986).

3M™ Inzisionsfolien—Produktubersicht, by 3M Medica, 6 annotated sheets.

Application for rationalization proposal, proposal entitled "Variant for vacuum treatment of purulent wounds," (4 sheets in English, 4 sheets in Russian, certificate of translation dated May 8, 2009), proposal allegedly executed Dec. 25, 1985 (Bagautdinov III).

Buschbaum, H.J., ed., et al., Strategies in Gynecologic Surgery, pp. 203, Springer-Verlag, NY, (1986).

Flynn, J-B. McC., et al., Technological Foundations in Nursing, pp. 506-507, Appleton & Lange, Norwalk, CT, (1990).

GOMCO Mobile constant and intermittent model 6030 & 6031, Operation, Maintenance and Service Manual, with annotations, 21 sheets, (Jan. 1987).

Kahlson, G., et al., "Wound healing as dependent on rate of histamine formation," The Lancet, pp. 230-234, (Jul. 30, 1960).

(56) References Cited

OTHER PUBLICATIONS

Karev, I.D., et al., "Foam drainage system for treating purulent wounds," pp. 87-88, (2 sheets English translation, 2 sheets Russian and certifcation of translation dated Apr. 6, 2009) (allegedly dated 1986).
Kozier, B., et al., Techniques in Clinical Nursing, 3d ed., pp. 559-560, pp. 603-605, Addison-Wesley Publishing Company, Inc., Health Sciences, Redwood City, CA, (1989).
McLean, W. C., "The role of closed wound negative pressure suction in radial surgical procedures of the head and neck," The Laryngoscope, 74(1)70-94, (Jan. 1964).
Norton, B.A., et al., Skills for Professional Nursing Practice: communication, physical appraisal, and clinical techniques, pp. 298-302, pp. 328-329, Appleton-Century-Crofts, Norwalk, CT (1986).
Bagautdinov, N.A., Report on Practical Application entitled "Variant of vacuum treatment of purulent wounds," Kazan Municipal Hospital No. 8, (1 sheet in English, 1 sheet in Russian and certificate of translation dated May 8, 2009), (allegedly dated Dec. 24, 1985). (Practical Report I).
Kuznetsov, V.A. et al., Report on Practical Application entitled "Method of vacuum-sorption treatment of purulent wounds," Kazan Municipal Hospital No. 8, (1 sheet in English, 1 sheet in Russian and certificate of translation dated Apr. 28, 2009) (allegedly dated May 19, 1986). (Practical Report II).
Bagautdinov, N.A., Report on Practical Application entitled "Method of vacuum treatment of open purulent wounds," Medical-Sanitary Ward of the Arzamas Instrument Plant, (1 sheet in English, 1 sheet in Russian and certificate of translation dated Apr. 27, 2009) (allegedly dated 1986).(Practical Report III).
Roth, B., et al., "Ubersichtsarbeit: Indication for suction-rinse drainage and hygienic certainty in drainages," GMS Krankenhaushyg. Interdiszip, 1(1):Doc27 (7 sheets in German with English abstract on first sheet) (2006).
Schneider, F.R., Handbook for the Orthopaedic Assistant, 2nd ed., pp. 185, The C.V. Mosby Company, St. Louis, (1976).
Thomas, S., Wound Management and Dressings, Chapter 4: Semipermeable film dressings (continued onto pp. 26-34), Chapter 5: Foam dressings (continued onto pp. 36-42), and pp. 166, The Pharmaceutical Press, London, (1990).
Witkowski, J.A., et al., "Synthetic dressings: wound healing in the 80's," (5 sheets), Hospital Therapy, (Nov. 1986).
Excerpts from Bier's Hyperemic Treatment, pp. 17-25, 44-46, 90-96, 167-170, 210-211 (1909).
Ramnarine, I.R., et al., "Vacuum-assisted closure in the paediatric patient with post-cardiotomy mediastinitis", Eur. J. Cardiothorac. Surg., 22:1029-31 (Dec. 2002).
Rollins, H., "Hypergranulation tissue at gastrostomy sites", J. Wound Care, 9(3):127-129 (Mar. 2000).
Schaum, K.D., "Medicare Part B negative pressure wound therapy pump policy. A partner for Medicare Part A PPS," Home Healthc. Nurse, 20(1):57-8 (Jan. 2002).
Shaer, W.D., "Inexpensive vacuum-assisted closure employing a conventional disposable closed-suction drainage system", Plast. Reconstr. Surg., 107(1):292-3 (Jan. 2001).
Saklani, A.P., et al., "Vacuum assisted closure system in the management of enterocutaneous fistula", Postgrad. Med. J., 78(925):699 (Nov. 2002).
Takei, T., et al., "Molecular basis for tissue expansion: clinical implications for the surgeon", Plast. Reconstr. Surg., 102(1):247-258 (Jul. 1998).
Tang, A.T.M., et al., "Vacuum-assisted closure to treat deep sternal wound infection following cardiac surgery", J. Wound Care, 9(5):229-30 (May 2000).
Nikkhah, C., et al., "Re: use of specialized bone screws for intermaxillary fixation", Ann. Plast. Surg., 47(1): 93, (Jul. 2001).
Voinchet, V., et al., "Vacuum assisted closure. Wound healing by negative pressure", Ann. Chir. Plast. Esthet., (English abstract on first page, and 1 sheet printout from PubMed); 41(5):583-9, (Oct. 1996).

Von Gossler, C.M., et al., "Rapid aggressive soft-tissue necrosis after beetle bite can be treated by radical necrectomy and vacuum suction-assisted closure", J. Cutan. Med. Surg., 4(4):219-222 (Oct. 2000).
Wilhelmi, B.J., et al., "Creep vs. stretch: a review of the viscoelastic properties of skin", Ann. Plast. Surg., 41 (2):215-219, (Aug. 1998).
Wiseman, J., et al., "Aesthetic aspects of neurofibromatosis reconstruction with the vacuum-assisted closure system", Aesth. Plast. Surg., 25:326-31 (Sep.-Oct. 2001).
Young, T., "Common problems in wound care: overgranulation", Br. J. Nursing, 4(3):169-170, (Feb. 9-22, 1995).
Ziegler, U.E., et al., "Skin substitutes in chronic wounds", Zentralbl. Chir., (English abstract on first page; 1 sheet printout from PubMed); 126 Suppl 1:71-4 (2001).
Stannard, J., "Complex orthopaedic wounds: prevention and treatment with negative pressure wound therapy", Orthop. Nurs., 23 Suppl 1:3-10 (10 sheets) (Mar.-Apr. 2004), presented at the 17th Annual Clinical Symposium on Advances in Skin & Wound Care, Dallas, TX (Sep. 23, 2002).
Patel, C.T.C., et al., "Vacuum-assisted wound closure: changing atmospheric pressure assists wound healing," AJN, 100:45-47 (2000).
Masters, J., "Reliable, inexpensive and simple suction dressings", Letters to the Editor, p. 267, labeled 1998.
Hazelbag, S., et al., "Cytokine profile of cervical cancer cells", Gynecol. Oncol., 83(2):235-243, (Nov. 2001).
Beitz, J.M., et al., "Abdominal wound with enterocutaneous fistula: a case study", J. Wound Ostomy Continence Nurs., 25(2):102-6, (Mar. 1998).
Baxandall, T., "Healing cavity wounds with negative pressure", Elderly Care, 9(1):20, 22 (Feb.-Mar. 1997).
McKinney, P.E., "Out-of-hospital and interhospital management of crotaline snakebite", Ann. Emerg. Med., 37 (2):168-174, (Feb. 2001).
Leroy, S.C., et al., "Severe penile erosion after use of a vacuum suction device for management of erectile dysfunction in a spinal cord injured patient. Case report", Paraplegia, 32(2):120-123 (Feb. 1994).
Bagautdinov, N.A., "Variant of external vacuum aspiration in the treatment of purulent diseases of soft tissues," Current Problems in Modern Clinical Surgery, Interdepartmental Collection, Cheboksary, (4 pages of English translation, 6 sheets in Russian, certification dated May 22, 2008, English translation of index card, 1 sheet Russian, certification dated May 7, 2008) (1986).
Chardak, W.M., et al., "Experimental studies on synthetic substitutes for skin and their use in the treatment of burns," Ann. Surg., 155(1):127-139, (Jan. 1962).
Fujimori, R., et al., "Sponge fixation method for treatment of early scars," Plast. & Reconst. Surg., 42(4):322-326, (Oct. 1968).
Kirk-Othmer, Encyclopedia of Chemical Technology, 2nd completely revised edition, vol. 14, pp. 227, John Wiley & Sons, Inc., (1967).
Meyer, W., et al., Excerpts from "Bier's Hyperemic Treatment", W.B. Saunders and Co., (47 sheets) (1908).
Westaby, S., et al., "A wound irrigation device," Lancet, pp. 503-504, (Sep. 2, 1978).
Conquest, A.M., et al., "Hemodynamic effects of the vacuum-assisted closure device on open mediastinal wounds," J. Surg. Res., 115(2):209-13 (Dec. 2003).
Copson, D., "Topical negative pressure and necrotising fasciitis", Nurs. Stand., 18(6):71-2, 74, 76, 78, 80 (Oct. 22, 2003).
Demaria, R.G., et al., "Topical negative pressure therapy. A very useful new method to treat severe infected vascular approaches in the groin," J. Cardiovascular Surg., 44(6):757-61 (Dec. 2003).
DeVooght, A., et al., "Vacuum-assisted closure for abdominal wound dehiscence with prosthesis exposure in hernia surgery," Plast. Recontr. Surg., 112(4):1188-9 (Sep. 15, 2003).
Duxbury, M.S., et al., "Use of a vacuum assisted closure device in pilonidal disease," J. Wound Care, 12(9):355 (Oct. 2003).
Eldad, A., et al., "Vacuum—A novel method for treating chronic wounds", Harefuah, (English abstract on last 2 pp. and 1 sheet printout from PubMed); 142(12):834-6, 878, 877 (Dec. 2003).
Evans, D., et al., "Topical negative pressure for treating chronic wounds", Cochrane Database Syst. Rev., vol. (3), accession No. 00075320-100000000-01309 (2005).

(56) References Cited

OTHER PUBLICATIONS

Fuchs, U., et al., "Clinical outcome of patients with deep sternal wound infection managed by vacuum-assisted closure compared to conventional therapy with open packaging: a retrospective analysis", Ann. Thorac. Surg., 79:526-31 (2005).

Gustafsson, R.I., et al., "Deep sternal wound infection: a sternal-sparing technique with vacuum-assisted closure therapy" Ann. Thorac. Surg., 76(6):2048-53 (Dec. 2003).

Herscovici Jr., D., et al., "Vacuum-assisted wound closure (VAC therapy) for the management of patients with high-energy soft tissue injuries", J. Orthop. Trauma, 17(10):683-8 (Nov.-Dec. 2003).

Huang, J., et al., "Treatment of open fracture by vacuum sealing technique and internal fixation", Zhongguo Xiu Fu Chong Jian Wai Ke Za Zhi, (English abstract on first page and 2 sheets printout from PubMed); 17(6):456-8 (Nov. 2003).

Jones, E.G., et al., "Management of an ileostomy and mucous fistula located in a dehisced wound in a patient with morbid obesity", J. Wound Ostomy Continence Nurs., 30(6):351-356 (Nov. 2003).

Langley-Hawthorne, C., "Economics of negative pressure wound therapy", Ostomy Wound Manage., 50(4A suppl):35, 36, C3 (Apr. 2004).

Neubauer, G., et al., "The cost-effectiveness of topical negative pressure versus other wound-healing therapies", J. Wound Care, 12(10):392-3 (Nov. 2003).

Orgill, D.P., et al., "Functional reconstruction following electrical injury", Ann. N.Y. Acad. Sci., 888:96-104 (Oct. 30, 1999).

Salameh, J.R., et al., "Laparoscopic harvest of omental flaps for reconstruction of complex mediastinal wounds", JSLS, 7(4):317-22 (Oct.-Dec. 2003).

Shoufani, A., et al., "Vacuum assisted closure—a new method for wound control and treatment", Harefuah, (English abstract on last page; 1 sheet printout from PubMed); 142(12):837-40, 877 (Dec. 2003).

Shvartsman, H.S., et al., "Use of vacuum-assisted closure device in the treatment of recurrent Paget's disease of the vulva", Obstet. Gynecol., Supplement, 102(5, part 2):1163-6 (Nov. 2003).

Sibbald, R.G., et al., "A consensus report on the use of vacuum-assisted closure in chronic, difficult-to-heal wounds", Ostomy Wound Manage., 49(11):52-66 (Nov. 2003).

Wagner, S., et al., "Comparison of inflammatory and systemic sources of growth factors in acute and chronic human wounds", Wound Rep. Reg., 11:253-260 (Jul.-Aug. 2003).

Wild, T., "Consensus of the German and Austrian Societies for wound healing and wound management on vacuum closure and the VAC treatment unit", MMW Fortschr. Med., (English abstract on p. 100; 1 sheet printout from PubMed); 145 Suppl. 3:97-101 (Oct. 9, 2003).

Chen, S.Z., et al., "Effect of vacuum-assisted closure on the expression of proto-oncogenes and its significance during wound healing", Zhonghua Zheng Xing Wai Ke Za Zhi, (English abstract on first page, 2 sheets printout from PubMed); 21:197-200 (May 2005).

Immer, F.F., et al., "Deep sternal wound infection after cardiac surgery: modality of treatment and outcome", Ann. Thorac. Surg., 80(3):957-61 (Sep. 2005; available online Aug. 23, 2005).

Saltzman, C.L., "Salvage of diffuse ankle osteomyelitis by single-stage resection and circumferential frame compression arthrodesis", Iowa Orthop. J., 25:47-52 (2005).

Bogart, L., "A summary of posters presented at the symposium on Advanced Wound Care: 2003 and 2004", Ostomy Wound Manage., 51(4):88-91 (Apr. 2005).

Chen, S.Z., et al., "Effects of vacuum-assisted closure on wound microcirculation: an experimental study", Asian J. Surg., 28(3):211-7 (Jul. 2005).

Paul, J.C., "Vacuum assisted closure therapy: A must in plastic surgery", Plastic Surg. Nurs., 25(2):61-5 (Apr.-Jun. 2005).

Winter, D., "Perspectives on vacuum-assisted closure therapy in pilonidal sinus surgery", Dis. Colon Rectum, 48 (9):1829-30, (Sep. 2005).

Arca, M.J., et al., "Use of vacuum-assisted closure system in the management of complex wounds in the neonate", Pediatr. Surg. Int., 21(7):532-5, 8 sheets, (published online Jun. 17, 2005).

Adamkova, M., et al., "First experience with the use of vacuum assisted closure in the treatment of skin defects at the burn center", Acta. Chir. Plast., 47(1):24-7 (2005).

Venturi, M.L., et al., "Mechanisms and clinical applications of the vacuum-assisted closure (VAC) device: a review", Am. J. Clin. Dermatol., 6(3):185-94 (2005).

Noel, B., "Management of venous leg ulcers", Rev. Med. Suisse, (English abstract on first page, 1 sheet printout from PubMed); 1(16):1062-6, 1068 (Apr. 20, 2005).

Riccio M. et al., "Delayed microsurgical reconstruction of the extremities for complex soft-tissue injuries", Microsurgery, 25:272-83 (2005).

Sjogren, J., et al., "Clinical outcome after poststernotomy mediastinitis: vacuum-assisted closure versus conventional treatment", Ann. Thorac. Surg., 79(6):2049-55 (Jun. 2005).

Dainty, L.A., et al., "Novel techniques to improve split-thickness skin graft viability during vulvo-vaginal reconstruction", Gynecol. Oncol., 97(3):949-52 (Jun. 2005).

Clubley, L., et al., "Using negative pressure therapy for healing of a sternal wound", Nurs. Times, 101(16):44-6 (Apr. 19, 2005).

Caniano, D.A., et al., "Wound management with vacuum-assisted closure: experience in 51 pediatric patients", J. Pediatr. Surg., 40(1):128-32 (Jan. 2005).

Steenvoorde, P., et al., "Deep infection after ilioinguinal node dissection: vacuum-assisted closure therapy?" Low. Extrem. Wounds, 3(4):223-226 (Dec. 2004).

Ryan, T.J., "Evans (1966) exchange and the skin in the light of vacuum-assisted closure, yoga, and maggots", Low. Extrem. Wounds, 3(3):121-2 (Sep. 2004).

Armstrong, D.G., et al., "Decreasing foot pressures while implementing topical negative pressure (vacuum-assisted closure) therapy", Low. Extrem. Wounds, 3(1):12-15 (Mar. 2004).

Wackenfors, A., et al., "Blood flow responses in the peristernal thoracic wall during vacuum-assisted closure therapy", Ann. Thorac. Surg., 79(5):1724-31 (May 2005).

Whelan, C., et al., "Mechanics of wound healing and importance of vacuum-assisted closure® in urology", J. Urol., 173:1463-70 (May 2005).

O'Connor, J., et al., "Vacuum-assisted closure for the treatment of complex chest wounds", Ann. Thorac. Surg., 79 (4):1196-200 (Apr. 2005).

Nugent, N., et al., "Vacuum-assisted closure—A management option for the burns patients with exposed bone", Burns, 31(3):390-393 (May 2005) (Epub Jan. 22, 2005).

Lambert, K.V., et al., "Vacuum assisted closure: a review of development and current applications", Eur. J. Vasc. Endovasc. Surg., 29(3):219-226 (Mar. 2005).

Smith, N., "The benefits of VAC Therapy in the management of pressure ulcers", Br. J. Nurs., 13(22):1359-60, 1362, 1364-65 (Dec. 9, 2004-Jan. 12, 2005).

White, R.A., et al., "Vacuum-assisted closure complicated by erosion and hemorrhage of the anterior tibial artery", J. Orthop. Trauma, 19(1):56-59 (Jan. 2005).

De Geus, H.R.H., et al., "Vacuum-assisted closure in the treatment of large skin defects due to necrotizing fasciitis", Intensive Care Med., 31(4): 601 (1 page) (Apr. 2005) (Epub Jan. 22, 2005).

Samson, D., et al., "Wound-healing technologies: low level laser and vacuum-assisted closure", Evid. Rep. Technol. Assess. (Summ.),(111):1-6, (Dec. 2004).

Gibson, K., "Vacuum-assisted closure", Am. J. Nurs., 104(12):16 (1 page) (Dec. 2004).

*Kinetic Concepts, Inc., et al., v. Bluesky Medical Corporation, et al.*, Civil Action No. SA-03-CA-0832-RF, U.S. District Court, W. Dist. of Texas San Antonio Div., Promotional Slide Presentation BlueSky Medical Negative Pressure Wound Care with Versatile 1 Presentation Presented by Penny Campbell and Shelly Burdette-Taylor 27 pages (dated Oct. 14, 2005).

Barillo, D., et al., "Management of Burns to the Hand", Wounds 15,(1):4-9, 2003 Health Management Publications, Inc., Posted Feb. 12, 2003.

(56) References Cited

OTHER PUBLICATIONS

Medical Technology & Innovation, "Medical Technology is Extending Life, Reducing Costs", vol. 1, Issue 46, Dec. 4, 2000.
Wu, Lisa C., et al., "Vacuum-Assisted Closure for the Treatment of Sternal Wounds: The Bridge Between Debridement and Definitive Closure", printout from www.plasticsurgery.org., 3 pages (printout dated Apr. 20, 2005).
Bertone, A., "Management of Exuberant Granulation Tissue", Wound Management, pp. 551-562 (Dec. 1989).
Taber's Cyclopedic Medical Dictionary, Edition 18, pp. 937, 942 and 1375.
Harris, Ann, et al., "Hypergranulation Tissue: a Nontraumatic Method of Management", Ostomy/Would Management, vol. 40, No. 5, Jun. 1994.
Webster's New Universal Unabridged Dictionary Deluxe Second Edition, p. 631.
Chariker-Jeter Technique Tutorial by Penny E. Campbell, Wound Care Solutions, 1 page tutorial chart.
Bluesky Medical, Negative Pressure Wound Therapy, Product Catalog Fall 2005, "Finally a choice . . . " 8 pages.
Chariker-Jeter Status Link from the website www.trademark.com/cbi-bin/tmlist, Oct. 14, 2005, 1 page.
Bluesky Medical Support, printout of webpages www.woundvacuum.com/Standard%20Pages/support.htm, Oct. 11, 2005, pp. 1-3.
Slides and photographs of patient treatment, 19 sheets, (Exhibit D-152) (allegedly dated 1987).
Slides, drawings, photographs of patient treatment and presentation slides, 20 sheets, (Exhibit D-151) (allegedly dated 1987).
Photographs of wound coverings and patient treatment, 16 sheets, (Exhibit D-240) (allegedly dated 1989).
Letter to Mr. Urs Tanner from Michael Baniak regarding: Updated Opinion of Non-infringement and Invalidity of Zamierowski U.S. Patent 4,969,880 and Argenta U.S. Patent 5,636,643, 30 pp., (Exhibit D-140) (dated Aug. 23, 2004).
Alberty, A., et al., "Effects of distraction and compression on proliferation of growth plate chondrocytes. A study in rabbits.", Acta Orthop. Scand., (1 sheet printout from PubMed); 64(4):449-455 (Aug. 1993).
Egnell Minor, Instruction Book, First Edition allegedly dated Feb. 1987, 34 pages of English translation.
Addition to the "Users Manual Concerning Overflow Protection—Concerns all Egnell Pumps", dated Feb. 3, 1983, 2 pages of English translation.
Svedman, P., et al., "Staphylococcal wound infection in the pig: Part I. Course," Ann. Plast. Surg., 23(3):212-218, (Sep. 1989).
Sanden, G., et al., "Staphylococcal wound infection in the pig: Part II. Inoculation, quantification of bacteria, and reproducibility," Ann. Plast. Surg., 23(3):219-223, (Sep. 1989).
Proto, Massachusetts General Hospital Dispaches from the Frontiers of Medicine, 2 sheets, (Winter 2006).
Powell, E.T., "The role of negative pressure wound therapy with reticulated open cell foam in the treatment of war wounds," J. Orthop. Trauma, vol. 22(10) Supp.: S138-S141, (Nov./Dec. 2008).
"Negative pressure wound therapy devices," Technology assessment report; Agency for Healthcare Research and Quality, with annotations, website dated May 26, 2009, printed Jun. 26, 2009 and Jun. 28, 2009.
Thomas, S., "Atraumatic dressings," World Wide Wounds, sponsored by Molnylcke Health Care, 11 sheets, published Jan. 2003, website printout dated Jun. 29, 2009.
Orgill, D.P., et al., "The mechanisms of action of vacuum assisted closure: More to learn," Surgery, 146(1):40-51, (Jul. 2009).
Defranzo, A., et al., "4: Vacuum-assisted closure in extremity trauma," in Soft Tissue Surgery, S.L. Moran et al., p. 49-60 and additional sheet, Lippincott Williams & Wilkins (Pub. Apr. 1, 2008).
Stoeckel, W.T., et al., "30: Vacuum assisted devices for difficult wounds of the face and neck," Essential Tissue Healing of the Face and Neck, p. 399-408, and additional sheet, Hom, et al., (Pub. Jan. 28, 2009).

Alexander, J.W., et al., "Clinical evaluation of epigard, a new synthetic substitute for homograft and heterograft skin," J. of Trauma, 13:374-383, (1973).
Anon., "Standard Test Methods for Water Vapor Transmission of Materials," ASTM, Designation: E 96/E 96M-05, Published Jun. 2005, 11 sheets, (Exhibit D-184).
Byers, R.M., "Clinical effects of closed suction drainage on wound healing in patients with head and neck cancer," Arch. Otolaryngol., vol. 108:723-6, (Nov. 1982).
Cesany, P., "Suction in the Treatment of Torpid Ulcerations," Rozhledy v chirurgii, 48-9, MINC022894-MINC022898, cover sheet and pp. 406-409 English abstract on p. 409 (1 sheet printout from PubMed) (Sep. 1969).
Chinn, S.D., "Closed wound suction drainage," J. Foot Surg., vol. 24: 76-81, (Jan.-Feb. 1985).
Email dated Jan. 14, 2002 with attachments, including "Report of Meeting with DG Consulting" dated Jan. 10, 2002, 5 sheets, (Exhibit D-157).
Westaby, S., "Treatment of purulent wounds and fistulae with an adhesive wound irrigation device," Annals of the Royal College of Surgeons, vol. 63: 353-6 (1981).
Hartz, R.R., et al., "Healing of the Perineal Wound," Arch. Surg., vol. 115, 471-474, (1980), (Exhibit D-395).
Mizuno, K., "Suctioning Sponge," Arch. Opthalmol., vol. 101:294, (Feb. 1983).
Morykwas, Laboratory Notebook pages and charts; 38 pages (Exhibit D-46) dated prior to Mar. 1993.
Morykwas, Laboratory notebook pages and charts, 16 sheets, (Exhibit D-286) dated prior to Mar. 1993.
Morykwas, Laboratory notebook pages and charts, 17 sheets, (Exhibit D-233) dated prior to Nov. 1991.
Morykwas, Laboratory notebook pages of charts, Aug. 29 and Dec. 19, 3 sheets, (Exhibit P-664) dated prior to Nov. 1991.
Nikolov, A., "Method of treatment of postphlebitic and varicose trophic ulcers on the lower extremities by vacuum [Vacuum treatment method in postphlebitic and varicose trophic ulcers of the lower extremities]," Khirurgiia, pp. 368-374, (English abstract on p. 371 and 1 sheet printout from PubMed) (1981).
Smith, S.R.G., "Surgical drainage", Br. J. Hosp. Med., 33(6):308-315 (Jun. 1985).
Svedman, "A dressing system providing fluid supply and suction drainage used for continuous or intermittent irrigation," Ann. Plast. Surg., vol. 17, 9 pages, (Aug. 1986).
Svedman, "Irrigation treatment in split thickness skin grafting of intractable leg ulcers," Scand. J. Plast. Reconstr. Surg., vol. 19:211-213, (1985).
Morykwas, Laboratory Notebook pages and charts; (D-46) dated prior to Nov. 1991.
Morykwas, Laboratory Notebook pages and charts; (D-286) dated prior to Nov. 1991.
Parikh, R.S., et al., "Self-adhesive drape (Opsite) for management of leaking abdominal wounds", Indian J. Gastroenterol., 19(4):178-180 (Oct. / Dec. 2000).
Alexis, A.F., et al., "Reassessment of the suction blister model of wound healing: introduction of a new higher pressure device", Int. J. Dermatol., 38(8):613-617 (Aug. 1999).
Gnanaraj, J., "A simple, sterile, low-cost, closed suction drainage system", Trop. Doct., 27(2):104 (Apr. 1997).
Klemm, K.W., "Antibiotic bead chains", Clin. Orthop. Rel. Res., (295):63-76 (Oct. 1993).
Pignatti, M., et al., "Mobile-VAC for the treatment of lower limb ulcers", Plast. Reconstr. Surg., 108(6):1837-1838 (Nov. 2001).
Schaum, K.D., "Payment strategies: a new medicare part B wound care policy", Adv. Skin & Wound Care, 14 (5):238-240 (Sep. / Oct. 2001).
Chariker, M.E., Presentation entitled, "Vacuum therapy in wound management", (Chariker deposition exhibit No. 1220), dated Oct. 27, 2005.
Chariker, M.E., Presentation entitled, "Closed wound suction", (Chariker deposition exhibit No. 1219), dated Mar. 17, 2005.
Argenta, P.A., et al., "Vacuum-assisted closure in the treatment of complex gynecologic wound failures," Obstet. Gynecol., 99(3):497-501, (9 sheets) (Mar. 2002).

(56) References Cited

OTHER PUBLICATIONS

Azad, S., et al., "Topical negative pressure may help chronic wound healing," B.M.J., 324:1100 (1 sheet) (May 4, 2002).
Ballard, K., et al., "Developments in wound care for difficult to manage wounds," Br. J. Nurs., 9(7):405-8,410,412 (Apr. 13-26, 2000).
Ballard, K., et al., "Vacuum-assisted closure," Nurs. Times, 97(35):51-2 (5 sheets) Aug. 30-Sep. 5, 2001.
Ballard, K., et al., "Use of vacuum-assisted closure therapy following foot amputation," Br. J. Nurs., 10(15 Supplement):S6, 8, 11-12 (Aug. 2001).
Banwell, P.E., "Topical negative pressure therapy in wound care," J. Wound Care, 8(2):79-84 (Feb. 1999).
Bartels, C.G., et al., "The vacuum sealing technique. A new approach to cover soft tissue defects, used after the resection of a leiomyosarcoma", (English abstract on 2nd page and 1 page printout from PubMed); Hautarzt, 52 (7):653-7 (Jul. 2001).
Bauer, P., et al., "Possibilities of preliminary treatment of infected soft tissue defects by vacuum sealing and PVA foam", (English abstract on first page and 1 sheet PubMed abstract), Handchir. Mikrochir. Plast. Chir., 30(1):20-3 (Jan. 1998).
Baynham, S.A., et al., "Treating stage IV pressure ulcers with negative pressure therapy: a case report", Ostomy Wound Manage., 45(4):28-32, 34-35 (Apr. 1999).
Birchall, L., et al., "Developing a trust-wide centralised approach to the use of TNP", J. Wound Care, 11(8):311-4 (Sep. 2002).
Brody, G.S., "Biological creep", Plast. Reconstr. Surg., 92(6):1202-1203 (Nov. 1993).
Campton-Johnston, S., et al., "Infected wound management: advanced technologies, moisture-retentive dressings, and die-hard methods", Grit. Care Nurs. Q, 24(2):64-77 (Aug. 2001).
Chen, K.D., et al., "Mechanotransduction in response to shear stress", J. Biol. Chem., 274(26):18393-18400, (Jun. 25, 1999).
Clare, M.P., et al., "Experience with the vacuum assisted closure negative pressure technique in the treatment of non-healing diabetic and dysvascular wounds", Foot Ankle Int., 23(10):896-901 (Oct. 2002).
Claxton, M.J., et al., "Healing the diabetic wound and keeping it healed: modalities for the early 21st century", Curr. Diab. Rep., 2(6):510-8 (Dec. 2002).
Coggrave, M., et al., "Topical negative pressure for pressure ulcer management", Br. J. Nurs., 11(6 Suppl):S29-31, S33-34, S36 (Mar. 2002).
Collier, M., "Know how: Vacuum assisted closure (VAC)", Nurs. Times, 93(5):32-3 (Jan. 29-Feb. 4 1997).
Cooper, S.M., et al., "Topical negative pressure", Int. J. Dermatol., 39(12):896-8 (Dec. 2000).
Cozart, R.F., et al., "The use of controlled subatmospheric pressure to promote wound healing in preparation for split-thickness skin grafting in a fourth degree burn", Tenn. Med., 92(10):382-4 (Oct. 1999).
Cro, C., et al., "Vacuum assisted closure system in the management of enterocutaneous fistulae," Postgrad. Med. J., 78(925):364-5 (Nov. 2002).
De Filippo, R.E., et al., "Stretch and growth: the molecular and physiologic influences of tissue expansion", Plast. Reconstr. Surg., 109(7):2450-2462 (Jun. 2002).
Deva, A.K., et al., "Vacuum-assisted closure of a sacral pressure sore", J. Wound Care, 6(7):311-312, (Jul. 1997).
Dunford, C., "Hypergranulation tissue", J. Wound Care, 8(10):506-507 (Nov. 1999).
Dunford, C.E., "Treatment of a wound infection in a patient with mantle cell lymphoma", Br. J. Nurs., 10(16):1058, 1060, 1062, 1064-5 (Sep. 13-26, 2001).
Espensen, E.H., et al., "Use of subatmospheric (VAC) therapy to improve bioengineered tissue grafting in diabetic foot wounds", J. Am. Podiatr. Med. Assoc., 92(7):395-7 (Jul.-Aug. 2002).
Fleck, T.M., et al., "The vacuum-assisted closure system for the treatment of deep sternal wound infections after cardiac surgery", Ann. Thorac. Surg., 74(5):1596-600 (Nov. 2002).

Svedman, P., et al., "A dressing system providing fluid supply and suction drainage used for continuous or intermittent irrigation", Ann. Plast. Surg., 17(2):125-33 (Aug. 1986).
"Pressure equivalents," McGraw-Hill Encyclopedia of Science & Technology, 6th ed., New York, pp. 249, (1987).
Bagautdinov, N.A., "Alternative method of external vacuum aspiration in the treatment of purulent soft tissue disease," Curr. Problems Contemporary Clin. Surg.: Interscholastic Collection, pp. 94-96, (6 sheets of English translation and certification dated May 30, 2008; four sheets of English translation, 6 sheets in Russian, and certification dated May 9, 2008; 1 sheet of English translation of alleged library index card, 1 sheet in Russian, and certification dated May, 7, 2008); I.N. Ulianov Chuvash State University, Cheboksary, (1986).
Zivadinovic, G., et al., "Vacuum therapy in the treatment of peripheral blood vessels," Conference Papers of the 5th Timok Medical Days, Majdanpek, No. 3-4, pp. 161-164, (5 sheets English translation; 5 sheets in Serbian, certification dated May 9, 2008) (1986).
Johnson, F.E., "An improved technique for skin graft placement using a suction drain", Surg. Gynecol. Obstet., 159 (6):584-585 (Dec. 1984).
Safronov, A.A., Dissertation Abstract, "Vacuum therapy of trophic ulcers of the lower leg with simultaneous autoplasty of the skin," (Central Scientific Research Institute of Traumotology and Orthopedics, Moscow, U.S.S.R.)(23 sheets English translation; 23 sheets in Russian; certification dated May 8, 2008; alleged index card(English translation; 1 sheet Russian; certification dated May 14, 2008), (1967).
Tribble, D.E., "An improved sump drain-irrigation device of simple construction," Arch. Surg., 105:511-513, (Sep. 1972).
Tennant, C.E., "The use of hyperemia in the postoperative treatment of lesions of the extremities and thorax," Jour. A.M.A., 64(19):1548-1549, (May 8, 1915).
Orgill, D.P., et al., "Microdeformational wound therapy—a new era in wound healing," Business Briefing: Global Surgery—Future Directions, pp. 22, 24-25 (2005).
"V.A.C.® Therapy Clinical Guidelines: A reference source for clinicians," KCI, The Clinical Advantage® (Jul. 2007).
Polly Jr., D.W., et al., "Advanced medical care for soldiers injured in Iraq and Afghanistan", Minn. Med., 87(11):42-4 (Nov. 2004).
Stone, P.A., et al., "Vacuum-assisted fascial closure for patients with abdominal trauma", J. Trauma, 57:1082-6 (Nov. 2004).
Connolly, T.P., "Necrotizing surgical site infection after tension-free vaginal tape", Obstet. Gynecol., 104(6):1275-6 (4 pages) (Dec. 2004).
Wackenfors, A., et al., "Effects of vacuum-assisted closure therapy on inguinal wound edge microvascular blood flow", Wound Rep. Regen., 12(6):600-6 (Nov.-Dec. 2004).
Schaffzin, D.M., et al., "Vacuum-assisted closure of complex perineal wounds", Dis. Colon Rectum, 47:1745-8 (Oct. 2004) (Published online Aug. 24, 2004).
Yousaf, M., et al., "Use of vacuum-assisted closure for healing of a persistent perineal sinus following panproctocolectomy: report of a case", Dis. Colon Rectum, 47(8):1403-8 (Aug. 2004) (Published online Aug. 12, 2004).
Fox, A., et al., "An unusual complication of vacuum assisted closure in the treatment of a pressure ulcer", J. Wound Care, 13(8):344-5 (Sep. 2004).
Saxena, V., et al., "Vacuum-assisted closure: microdeformations of wounds and cell proliferation", Plast. Reconstruct. Surg., 114(5):1086-96 (Oct. 2004).
Scholl, L., et al., "Sternal osteomyelitis: use of vacuum-assisted closure device as an adjunct to definitive closure with sternectomy and muscle flap reconstruction", J. Card. Surg., 19(5):453-61 (Sep.-Oct. 2004).
Ohye, R.G., et al. "Primary closure for postoperative mediastinitis in children", J. Thorac. Cardiovasc. Surg., 128 (3):480-6 (Sep. 2004).
Tang, S.Y., et al., "Influence of vacuum-assisted closure technique on expression of Bcl-2 and NGF/NGFmRNA during wound healing", Zhonghua Zheng Xing Wai Ke Za Zhi, (English abstract on first p. 1 sheet printout from PubMed); 20(2):139-42 (Mar. 2004).
Armstrong, D.G., et al., "Guidelines regarding negative wound therapy (NPWT) in the diabetic foot", Ostomy Wound Manage., 50(4B Suppl.):3S-27S (Apr. 2004).

(56) References Cited

OTHER PUBLICATIONS

Shilt, J.S., et al., "Role of vacuum-assisted closure in the treatment of pediatric lawnmower injuries", J. Pediatr. Orthop., 24(5):482-7 (Sep-Oct. 2004).

Antony, S., et al., "A retrospective study: clinical experience using vacuum-assisted closure in the treatment of wounds", J. Natl. Med. Assoc., 96(8):1073-7 (Aug. 2004).

Steenvoorde, P., et al., "Vacuum-assisted closure therapy and oral anticoagulation therapy", Plast. Reconstruct. Surg., 113(7):2220-1 (Jun. 2004).

Oczenski, W., et al., "Vacuum-assisted closure for the treatment of cervical and mediastinal necrotizing fasciitis", J. Cardiothorac. Vasc. Anesth., 18(3):336-8 (Jun. 2004).

Carson, S.N., et al., "Vacuum-assisted closure used for healing chronic wounds and skin grafts in the lower extremities", Ostomy Wound Manage., 50(3):52-8 (9 sheets) (Mar. 2004).

Marathe, U.S., et al., "Use of the vacuum-assisted closure device in enhancing closure of a massive skull defect", Laryngoscope, 114(6):961-4 (8 sheets) (Jun. 2004).

Schintler, M.V., et al., "The impact of the VAC-treatment for locally advanced malignancy of the scalp", Zentralbl. Chir., (English abstract on first page, 1 sheet printout from PubMed); 129 Suppl: 1:S141-S146 (May 2004).

Querings, K., et al., "Revitalization of a gluteal abscesses with V.A.C. therapy (vacuum assisted closure)", Zentralbl. Chir, (English abstract on first page, 1 sheet printout from PubMed); 129 Suppl 1:S138-S140 (May 2004).

Kall, S., et al., "Influence of foam- and tubing material of the vacuum assisted closure device (V.A.C.) on the concentration of transforming growth factor beta 1 in wound fluid", Zentralbl. Chir., (English abstract on first page, 2 sheets printout from PubMed); 129 Suppl 1: S113-S115 (May 2004).

Mang, R., et al., "Vacuum therapy in a pre- and postsurgical ulcera crurum", Zentralbl. Chir., (English abstract on first page, 1 sheet printout from PubMed); 129 Suppl 1:S101-S103 (May 2004).

Steiert, A.E., et al., "The V.A.C. system (vacuum assisted closure) as bridging between primary osteosynthesis in conjunction with functional reconstructed of soft tissue—open fractures type 2 and type 3", Zentralbl. Chir., (English abstract on first page, 2 sheets printout from PubMed); 129 Suppl 1:S98-100 (May 2004).

Karl, T., et al., "Indications and results of V.A.C. therapy treatments in vascular surgery—state of the art in the treatment of chronic wounds", Zentralbl. Chir., (English abstract on first page, 1 sheet printout from PubMed); 129 Suppl 1:S74-S79 (May 2004).

Ferbert, T., et al., "Treatment of soft tissue defects on hand and forearm with vacuum assisted closure", Zentralbl. Chir., (English abstract on first page, 1 sheet printout from PubMed); 129 Suppl 1:S57-S58 (May 2004).

Halama, D., et al., "Intraoral application of vacuum-assisted closure in the treatment of an extended mandibular keratocyst", Zentralbl. Chir., (English abstract on first page, 1 sheet printout from PubMed); 129 Suppl 1:S53-S56 (May 2004).

Fleck, T., et al., "Early treatment of sternal wound infections with vacuum assisted closure therapy reduces.involvement of the mediastinum and further diminishes the need of plastic reconstructive surgery", Zentralbl. Chir., (1 sheet printout from PubMed); 129 Suppl 1:S35-S37 (May 2004).

Kutschka, I., et al., "Vacuum assisted closure therapy improves early postoperative lung function in patients with large sternal wounds", Zentralbl. Chir., (English abstract on first page, 1 sheet printout from PubMed); 129 Suppl 1: S33-S34 (May 2004).

Labler, L., et al., "New application of V.A.C. (vacuum assisted closure) in the abdominal cavity in case of open abdomen therapy", Zentralbl. Chir., (English abstract on first page, 2 sheets printout from PubMed); 129 Suppl 1:S14-S19 (May 2004).

Wild, T., et al., "Consensus of the German and Austrian Societies for Wound Healing and Wound Management on vacuum closure and the V.A.C. treatment unit", Zentralbl. Chir., (English abstract on first page, 2 sheet printout from PubMed and 1 sheet of erratum); 129 Suppl 1:S7-S11 (May 2004).

Weed, T., et al., "Quantifying bacterial bioburden during negative pressure wound therapy. Does the wound VAC enhance bacterial clearance?" Ann. Plast. Surg., 52(3):276-80 (Mar. 2004).

Mustoe, T., "Understanding chronic wounds: a unifying hypothesis on their pathogenesis and implications for therapy", Am. J. Surg., 187(5A):65S-70S (May 2004).

Tzeng, Y.J., et al., "Using vacuum-assisted closure (VAC) in wound management", Hu Li Za Zhi, (English abstract on last page, 1 sheet printout from PubMed); 51(2):79-83 (Apr. 2004).

Quah, H.M., et al., "Vacuum-assisted closure in the management of the open abdomen: a report of a case and initial experiences", J. Tissue Viability, 14(2):59-62 (Apr. 2004).

Emohare, O., et al., "Vacuum-assisted closure use in calciphylaxis", J. Burn Care Rehabil., 25(2):161-4 (Mar.-Apr. 2004).

Wackenfors, A., et al., "The effect of vacuum-assisted closure therapy on the pig femoral artery vasomotor responses", Wound Repair Regen., 12(2):244-51 (Mar.-Apr. 2004).

Sjogren, J., et al., "Vacuum-assisted closure therapy in mediastinitis after heart transplantation", J. Heart Lung Transplant., 23(4):506-7 (Apr. 2004).

Miller, Q., et al., "Effect of subatmospheric pressure on the acute healing wound", Curr. Surg., 61(2):205-8 (Mar.-Apr. 2004).

Penn, E., et al., "Management of a dehisced abdominal wound with VAC therapy", Br. J. Nurs., 13(4):194, 196, 198-201 (Feb. 26-Mar. 10, 2004).

Moues, C.M., et al., "Bacterial load in relation to vacuum-assisted closure wound therapy: a prospective randomized trial", Wound Repair Regen., 12(1):11-7 (Jan.-Feb. 2004).

Schimp, V.L., et al., "Vacuum-assisted closure in the treatment of gynecologic oncology wound failures", Gynecol. Oncol., 92(2):586-91 (Feb. 2004).

Aru, G.M., et al., "Limitations on the role of vacuum-assisted closure in cardiac surgery", J. Thorac. Cardiovasc. Surg., 127(2):604-5 (Feb. 2004).

Bihariesingh, V.J., et al., "Plastic solutions for orthopaedic problems", Arch. Orthop. Trauma. Surg., 124(2):73-6 (Mar. 2004) (Epub Jan. 17, 2004).

Kaplan, M., "Managing the open abdomen", Ostomy Wound Manage., 50(1A suppl):C2, 1-8, and 1 sheet of quiz (Jan. 2004).

Colwell, A.S., et al., "Management of early groin vascular bypass graft infections with sartorius and rectus femoris flaps", Ann. Plast. Surg., 52(1):49-53 (Jan. 2004).

Evidence Report/Technology Assessment, No. 111, "Wound healing technologies: low-level laser and vacuum-assisted closure", prepared for Agency for Healthcare Research and Quality by the Blue Cross and Blue Shield Association Technology Evaluation Center Evidence-based Practice Center, under Contract No. 290-02-0026, AHRQ Publications Clearinghouse, Available Dec. 2004.

Wolvos, T., "Wound instillation—the next step in negative pressure wound therapy. Lessons learned from initial experiences", Ostomy Wound Manage., 50(11):56-58, 60-66 (Nov. 2004).

Bluman, E.M., et al., "Subatmospheric pressure-induced compartment syndrome of the entire upper extremity. A case report", J. Bone Joint Surg. (Am.), 86-A(9):2041-4 (Sep. 2004).

Kamolz, L.P., et al., "Use of subatmospheric pressure therapy to prevent burn wound progression in human: first experiences", Burns, 30(3):253-8 (May 2004) (Available online Mar. 16, 2004).

Jones, S.M., et al., "Advances in wound healing: topical negative pressure therapy", Postgrad. Med. J., 81 (956):353-7 (Jun. 2005).

Moues, C.M., et al., "An economic evaluation of the use of TNP on full-thickness wounds", J. Wound Care, 14 (5):224-7 (May 2005).

Lee, S.S., et al., "Management of intractable sternal wound infections with topical negative pressure dressing", J. Card. Surg., 20(3):218-22 (May-Jun. 2005).

Jethwa, P., et al., "Using topical negative pressure therapy to resolve wound failure following perineal resection", J. Wound Care, 14(4):166-7 (Apr. 2005).

Banwell, P.E., et al., "Topical negative pressure therapy: mechanisms and indications", Int. Wound J., 1(2):95 (15 pages) (Jun. 2004).

Melano, E., et al., "The effects of Panafil when using topical negative pressure to heal an infected sternal wound," J. Wound Care, 13(10):425-6 (Nov. 2004).

(56) References Cited

OTHER PUBLICATIONS

Morton, N., "Use of topical negative pressure therapy in postoperative dehisced or infected wounds", J. Wound Care, 13(8):346-8 (Sep. 2004).
Moisidis, E., et al., "A prospective, blinded, randomized, controlled clinical trial of topical negative pressure use in skin grafting", Plast. Reconstr. Surg., 114(4):917-22 (7 sheets) (Sep. 15, 2004).
Tachi, M., et al., "Topical negative pressure using a drainage pouch without foam dressing for the treatment of undetermined pressure ulcers", Ann. Plast. Surg., 53(4):338-42 (7 sheets) (Oct. 2004).
Jones, S.M., et al., "Complications of topical negative pressure therapy in small-diameter wounds", Plast. Reconstr. Surg., 114(3):815-817 (5 sheets) (Sep. 1, 2004).
Loree, S., et al., "Is vacuum assisted closure a valid technique for debriding chronic leg ulcers?" J. Wound Care, 13(6):249-52 (Jun. 2004).
Vogt, P.M., et al., "Several aspects of foam materials and their possible interactions with the wound surface in the vacuum therapy", Zentralbl. Chir., (English abstract on first page, 1 sheet printout from PubMed); 129 Suppl 1:S92-S94 (May 2004).
Haslik, W., et al., "The use of subatmospheric pressure to prevent burn wound progression: first experiences in burn wound treatment", Zentralbl. Chir., (English abstract on first page, and 1 sheet printout from PubMed); 129 Suppl. 1:S62-63 (May 2004).
Steenvoorde, P., et al., "Combining topical negative pressure and a Bogota bag for managing a difficult laparostomy", J. Wound Care, 13(4):142-3 (Apr. 2004).
Pullen, R., "Treatment of pressure sores in elderly patients", Z. Genrontol. Geriatr., (English abstract on first page, 1 sheet printout from PubMed); 37(2):92-9 (Apr. 2004).
Gottrup, F., "Optimizing wound treatment through health care structuring and professional education", Wound Repair Regen., 12(2):129-33 (Mar.-Apr. 2004).
(Anon.) "New best practice guidelines for managing pressure ulcers with negative pressure wound therapy published", Home Healthcare Nurse, 23(7):469 (one sheet) (Jul. 2005).
Stechmiller, J.K., et al., "Effect of negative pressure wound therapy on the expression of TNF-alpha, IL-1beta, MMP-2, MMP-3, and TIMP-1 in wound fluids of adults with pressure ulcers", Wound Repair Regen., 13(2):A16 (Mar.-Apr. 2005).
Snyder, R.J., "Negative pressure wound therapy (NPWT)/ vacuum-assisted closure® (VAC®) as an adjunct in the treatment of pyoderma gangrenosum", Wound repair and regeneration, 13:A29 (Mar. 2005).
Armstrong, D.G., et al., "Negative pressure wound therapy in treatment of diabetic foot wounds: a marriage of modalities", Ostomy Wound Manage., 50(4A suppl):9-12 (Apr. 2004).
Armstrong, D.G., et al., "Plantar pressure changes using novel negative pressure wound therapy technique", J. Am. Podiatr. Med. Assoc., 94(5):456-60 (Sep.-Oct. 2004).
Baharestani, M.M., "Negative pressure wound therapy: An examination of cost-effectiveness", Ostomy Wound Manage., 50(11A suppl):29S-33S (Nov. 2004).
Bernstein, B.H., et al., "Combination of subatmospheric pressure dressing and gravity feed antibiotic instillation in the treatment of post-surgical diabetic foot wounds: a case series,"parts 1 and 2, Wounds, 17(2):37-48 (23 sheets) (Feb. 2005).
Datiashvili, R.O., et al., "Negative pressure dressings: An alternative to free tissue transfers?" Wounds, 17(8):206-212 (Aug. 2005).
De Leon, J., "Negative pressure wound therapy in pressure ulcer management", Ostomy Wound Manage., 51(2A suppl):3S-8S (Feb. 2005).
Dobke, M.K., et al., "A novel approach to acute infection of the glenohumeral joint following rotator cuff repair—a case series", Wounds, 17(6):137-40 (6 sheets) (Jun. 2005).
Dunbar, A., et al., "Addressing the pain: Silicone net dressings as an adjunct with negative pressure wound therapy", Ostomy Wound Manage., 51(4):18-20 (4 sheets) (Apr. 2005).
Etoz, A., et al., "The use of negative pressure wound therapy on diabetic foot ulcers: A preliminary controlled trial", Wounds, 16(8):264-9 (Aug. 2004).

Fife, C.E., et al., "Healing dehisced surgical wounds with negative pressure wound therapy", Ostomy Wound Manage., 50(4A suppl):28-31 (Apr. 2004).
Geller, S.M., et al., "Ulceration of pyoderma gangrenosum treated with negative pressure wound therapy", J. Am. Podiatr. Med. Assoc., 95(2):171-4 (Mar.-Apr. 2005).
Gray, M., et al., "Is negative pressure wound therapy effective for the management of chronic wounds?"J. Wound Ostomy Continence Nurs., 31(3):101-5 (May-Jun. 2004).
Gupta, S., et al., "A literature review of negative pressure wound therapy", Ostomy Wound Manage., 50(11A suppl):2S-4S (Nov. 2004).
Gupta, S., et al., "The perioperative use of negative pressure wound therapy in skin grafting", Ostomy Wound Mangage., 50(4A suppl):32-4 (Apr. 2004).
Gupta, S., et al., "Guidelines for managing pressure ulcers with negative pressure wound therapy", Adv. Skin Wound Care, 17(Suppl 2):1-16 (Nov.-Dec. 2004).
Huljev, D., et al., "Necrotizing fasciitis of the abdominal wall as a post-surgical complication: a case report", Wounds, 17(7):169-77 (10 sheets) (2005) (Posted Aug. 11, 2005).
Kaplan, M., "Negative pressure wound therapy in the management of abdominal compartment syndrome", Ostomy Wound Manage., 51(2A suppl):29S-35S (Feb. 2005).
Mendez-Eastman, S., "Determining the appropriateness of negative pressure wound therapy for pressure ulcers", Ostomy Wound Manage., 50(4A suppl):13-16 (Apr. 2004).
Mendez-Eastman, S., "Using negative-pressure for positive results", Nursing, 35(5):48-50 (May 2005).
Miller, M.S., et al., "Negative pressure wound therapy: 'A rose by any other name'", Ostomy Wound Manage., 51(3):44-9 (11 sheets) (Mar. 2005).
Niezgoda, J.A., et al., "The economic value of negative pressure wound therapy", Ostomy Wound Manage., 51 (2A suppl):44S-47S (Feb. 2005).
Niezgoda, J.A., "Combining negative pressure wound therapy with other wound management modalities", Ostomy Wound Manage., 51(2A suppl):S36-8 (Feb. 2005).
Orgill, D.P., et al., "Guidelines for treatment of complex chest wounds with negative pressure wound therapy", Supplement B to Wounds: A Compendium of Clinical Research and Practice, (24 sheets) (Dec. 2004).
Orgill, D.P., "Utilizing negative pressure wound therapy on open chest/sternotomy wounds", Ostomy Wound Manage., 50(11A suppl):15S-17S (Nov. 2004).
Orgill, D.P., "Advancing the treatment options of chest wounds with negative pressure wound therapy", Ostomy Wound Manage., 51(2A suppl):39S-43S (Feb. 2005).
Page, J.C., et al., "Retrospective analysis of negative pressure wound therapy in open foot wounds with significant soft tissue defects", Adv. Skin Wound Care, 17(7):354, 356, 358-60, 362-64 (Sep. 2004).
Page, J.C., et al., "Negative pressure wound therapy in open foot wounds with significant soft tissue defects", Ostomy Wound Manage., 51(2A suppl):9S-14S (Feb. 2005); excerpted from Page, J.C., et al. "Retrospective analysis of negative pressure wound therapy in open foot wounds with significant soft tissue defects", Adv. Skin & Wound Care, 17(7):354-364, (2004).
Pattison, P.S., et al., "Case report: Using dual therapies—Negative pressure wound therapy and modified silicone gel liner—to treat a limb postamputation and dehiscence", Wounds, 17(8):233-40 (11 sheets) (Aug. 2005).
Ratliff, C.R., "Negative-pressure wound therapy. Adjunct relief for chronic wounds", Adv. Nurs. Pract., 12(7):47-9 (3 sheets) (Jul. 2004) (Issue date: Jul. 1, 2004).
Sarsam, S.E., et al., "Management of wound complications from cesarean delivery,"Obstet. Gynecol. Surv., 60(7):462-73 (Jul. 2005).
Schaum, K.D., "Payment perspective: Negative pressure wound therapy pumps and ostomy supplies", Ostomy Wound Manage., 51(3):20-22 (2 sheets) (Mar. 2005).
Simman, R., et al., "A comparative histological study of skin graft take with tie-over bolster dressing versus negative pressure wound therapy in a pig model: a preliminary study [brief communication]", Wounds, 16(2):76-80 (7 sheets) (Feb. 2004).

(56) References Cited

OTHER PUBLICATIONS

Stone, P., et al., "Bolster versus negative pressure wound therapy for securing split-thickness skin grafts in trauma patients", Wounds, 16(7):219-23 (5 sheets) (2004) (Posted Aug. 4, 2004).

Wolvos, T., "Wound instillation with negative pressure wound therapy", Ostomy Wound Manage., 51(2A suppl):21S-26S (Feb. 2005).

Jeter, K., "Closed suction wound drainage system", JWOCN, 31(2):51 (1 sheet) (Mar.-Apr. 2004).

Agarwal, J.P., et al., "Vacuum-assisted closure for sternal wounds: a first-line therapeutic management approach", Plast. Reconstr. Surg., 116(4):1035-1040 (Sep. 15, 2005).

Sjogren, J., et al., "The impact of vacuum-assisted closure on long-term survival after post-sternotomy mediastinitis", Ann. Thorac. Surg., 80(4):1270-5, (Oct. 2005).

Mendez-Eastman, S., "New advances in wound therapy", printout from Wounds1.com; 7 sheets (Apr. 15, 2005).

"Promoting wound healing", Nurses-Digest, 2(3), 6 sheets, Mar. 2005.

Roylance, L., "Nancy Sujeta, Amanda Clark,"DOME, vol. 55, Mar. 2004, 2 sheets of website printout www.hopkinsmedicine.org/dome/0405/feature4.cfm.

Agarwal, J.P., et al., "Vacuum assisted closure™ for sternal wounds: a first line therapeutic management", ASPS, Plastic Surgery 2004, Philadelphia, PA, abstract (2 sheets) (Wednesday Oct. 13, 2004).

Gomoll, A.H., et al., "Incisional vacuum-assisted closure therapy", J. Orthop. Trauma, 20(10):705-709, (Nov.-Dec. 2006).

Leininger, B.E., et al., "Experience with wound VAC and delayed primary closure of contaminated soft tissue injuries in Iraq", J. Trauma, 61(5):1207-1211 (Nov. 2006).

Gupta, S., ed., "Differentiating negative pressure wound therapy devices: an illustrative case series", Wounds, 19(1 suppl):1-9, (Jan. 2007).

Korasiewicz, L.M., "Abdominal Wound With a Fistula and Large Amount of Drainage Status After Incarcerated Hernia Repair", Journal of Wound, Ostomy & Continence Nursing. 31(3):150-153, (May-Jun. 2004).

Guntinas-Lichius, O., et al., "The role of growth factors for disease and therapy in diseases of the head and neck", DNA and Cell Biol., 22(9):593-606, (Sep. 2003).

Goldman, R., "Growth factors and chronic wound healing: past, present, and future", Adv. Skin Wound Care, 17 (1):24-35, (Jan.-Feb. 2004).

Malli, S., "Keep a close eye on vacuum-assisted wound closure", Nursing, 35(7):25 (Jul. 2005).

Lynch, J.B., et al., "Vacuum-assisted closure therapy: a new treatment option for recurrent pilonidal sinus disease. Report of three cases", Dis. Colon Rectum, 47(6):929-32 (Jun. 2004) (Published online May 4, 2004).

MX: Business Strategies for Medical Technology Executives, (Mar. / Apr. 2005).

Niezgoda, J.A., "Incorporting negative pressure therapy into the management strategy for pressure ulcers", Ostomy Wound Manage., 50(11A suppl.):5S-8S, (Nov. 2004).

Banwell, P.E., "Topical negative pressure therapy: advances in burn wound management", Ostomy Wound Manage., 50(11A suppl.):9S-14S, (Nov. 2004).

Kaplan, M., "Negative pressure wound therapy in the management of abdominal compartment syndrome", Ostomy Wound Manage., 50(11A suppl):20S-25S, (Nov. 2004).

Gupta, S., et al., "The perioperative use of negative pressure wound therapy in skin grafting", Ostomy Wound Manage., 50(11A suppl. ):26S-28S, (Nov. 2004).

Schoemann, M.B., et al., "Treating surgical wound dehiscence with negative pressure dressings", Ostomy Wound Manage., 51(2A suppl. ):15S-20S, (Feb. 2005).

Bookout, K., et al., "Case studies of an infant, a toddler, and an adolescent treated with a negative rpessure wound treatment system", J. Wound OstomyContinence Nurs., 31(4):184-192, (8 pp.) (Jul. / Aug. 2004).

Borkowski, S., "G tube care: managing hypergranulation tissue", Nursing, 35(8):24 (Aug. 2005).

Machen, M. S., "Management of traumatic war wounds using vacuum-assisted closure dressings in an austere environment," Army Medical Department J., pp. 17-23, (Jan.-Mar. 2007).

Peck, M.A., et al., "The complete management of extremity vascular injury in a local population: a wartime report from the 332nd Expeditionary Medical Group/Air Force Theater Hospital, Balad Air Base, Iraq," J. Vasc. Surg., pp. 1-9, (2007), (Presented at the Plenary Session of the Eastern Vascular Society's Twentieth Annual Meeting, Washington D.C., Sep. 30, 2006).

Giovannini, U.M., et al., "Topical negative therapy and vacuum assisted closure. New strategies and devices in surgical reconstruction", Minerva Chir., 60(3):191-4 (Jun. 2005).

Avery, C., et al., "Negative pressure wound dressing of the radial forearm donor site", International Journal of Oral Maxillofacial Surgery, 2000; 29, pp. 198-200.

Armstrong, David G., et al., "Outcomes of Subatmospheric Pressure Dressing Therapy on Wounds of the Diabetic Foot", Ostomy/Wound Management 2002; 4(4): 64-68.

Brown, Karen M., et al., "Vacuum-Assisted Closure in the Treatment of a 9-Year-Old Child with Severe and Multiple Dog Bite Injuries of the Thorax", Society of Thoracic Surgeons, 2001; 72:1409-1410.

Catarino, Pedro A., et al., "High-Pressure Suction Drainage via a Polyurethane Foam in the Management of Poststernotomy Mediastinitis", Ann Thorac Surg 2000; 70:1891-5.

Mendez-Eastman, Susan, RN, CPSN, CWCN, Clinical Management Extra, Guidelines for Using Negative Pressure Wound Therapy, Advances in Skin & Wound Care, Nov./Dec. 2001, vol. 14, No. 6, p. 314-323.

Cooper, Susan Mary, "Topical negative pressure in the treatment of pressure ulcers", Letters posted in the Journal of the American Acad of Dermatology, August, Part 1, 1999, p. 280.

Davydov, I.A., et al., "Concept of clinico-biological control of the wound", Vestnik khirurgii imeni I.I. Grekova, v. 146, issue 2, 1991, 132-6 (with English translation).

de la Torre, Jorge I., MD, et al., "Healing a Wound with an Exposed Herrington Road: A Case Study", Ostomy Wound Management, pp. 18-19, May 2002, vol. 48, Issue 5.

de Lange, M.Y., et al., "Vacuum-assisted closure: indications and clinical experience", Eur J Plast Surg (2000) 23:178-182.

Deva, Anand, K., et al., "Topical negative pressure in wound management", MJA, Vo. 173, pp. 128-131, Aug. 7, 2000.

Elwood, Eric T., et al., "Negative-Pressure Dressings in the Treatment of Hidradenitis Suppurativa", Ann Plast Surgery Jan. 2001; 46:49-51.

Evans, D. and Land, L., "Topical negative pressure for treating chronic wounds: a systematic review", British Journal of Plastic Surgery (2001), 54, 238-242.

Fabian, Thaddeus S., MD, "The Evaluation of Subatmospheric Pressure and Hyperbaric Oxygen in Ischemic Full-Thickness Wound Healing", The American Surgeon, Dec. 2000, vol. 66, 1136-1143.

Fenn, C.H. and Butler, P.E.M., "Abdominoplasty wound-healing complications: assisted closure using foam suction dressing", British Journal of Plastic Surgery (2001), 54, 348-351.

Giovannini, Uberto M., MD, "Negative Pressure for the Management of an Exposed Vascular Dacron Polyester Patch", Annals of Plastic Surgery, 47(5): 577-578, 2001.

Gustafsson, Ronny, MD, "Vacuum-assisted closure therapy guided by C-reactive protein level in patients with deep sternal wound infection", The Journal of Thoracic and Cardiovascular Surgery, vol. 123, No. 5, pp. 895-900, May 2002.

Gwan-Nulla, Daniel N., MD and Casal, Rolando S., MD, "Toxic Shock Syndrome Associated with the Use of the Vacuum-Assisted Closure Device", Ann Plastic Surgery 2001;47:552-554.

Hersh, Robert E., MD, et al., "The Vacuum-Assisted Closure Device as a Bridge to Sternal Wound Closure", Ann Plast Surg. 2001; 46: 250-254.

Heugel, Judson R., et al., "Treatment of the Exposed Achilles Tendon Using Negative Pressure Wound Therapy: A Case Report", Journal of Burn Care and Rehabilitation, May/Jun. 2002, vol. 23, No. 3, pp. 167-171.

(56) References Cited

OTHER PUBLICATIONS

Joseph, Emmanuella, MD, et al., "A Prospective Randomized Trial of Vacuum-Assisted Closure Versus Standard Therapy of Chronic Nonhealing Wounds", WOUNDS 2000: 12(3): 60-67.
Josty, I.C., et al., "Vacuum-assisted closure: an alternative strategy in the management of degloving injuries of the foot", British Journal of Plastic Surgery (2001), 54, pp. 363-365.
Kostiuchenok, B.M., et al., "Vacuum Treatment in the Surgical Management of Suppurative Wounds", Izdatelstvo Meditsina, St. Petersburg, Sep. 1986; 137(9): 18-21 (with English Translation).
Kovacs, Laszlo H., MD, "Necrotizing Fasciitis", Annals of Plastic Surgery, vol. 47, No. 6, Dec. 2001, pp. 680-682.
Kranser, Diane L., "Managing Wound Pain in Patients with Vacuum-Assisted Closure Devices", Ostomy Wound Management 2002; 48(5): 38-43.
Mendez-Eastman, Susan, RN, CPSN, CWCN, "wound therapy", Nursing2002, vol. 32, No. 5, May, pp. 59-63 and 1 sheet of quiz.
Mooney, James F., III., "Treatment of Soft Tissue Defects in Pediatric Patients Using the V.A.C. TM System", Clinical Orthopedics and Related Research, No. 376, pp. 26-31, Jul. 2000.
Scheufler, O., et al., "Problem-adapted application of vacuum occlusion dressings: case report and clinical experience", Eur J. Plast Surg (2000) 23: 386-390.
Sposato, G., et al., "Ambulant vacuum-assisted closure of skin-graft dressing in the lower limbs using a portable mini-VAC device", British Journal of Plastic Surgery (2001), 54, 235-237.
Tang, Augustine T.M., et al., "Novel application of vacuum assisted closure technique to the treatment of sternotomy wound infection", European Journal of Cardio-Thoracic Surgery 17 (2000) 482-484.
Wu, S.H., et al., "Vacuum therapy as an intermediate phase in wound closure: a clinical experience", Eur J Surg (2000) 23:174-177.
Zhivotaev VM. Vacuum therapy of postoperative infected wounds of the urinary bladder, Klinicheskaia Khiurgiia. 1970;5:36-39. (in Russian) (and 1 sheet printout from PubMed).
The Kremlin Papers . . . perspectives in wound care, "A collection of published studies complementing the research and innovation of wound care", Russian Medical Journal "Vestnik Khirurgii", 5 Russian Articles from 1986-1991, translated by BlueSky Medical Group Inc. © 2004.
Davies, J.W.L, "Synthetic materials for covering burn wounds: Progress towards perfection. Part I. Short term dressing materials", Burns, Nov. 1983;10(2), 94-103.
Lamke, L.O., et al., "The evaporative water loss from burns and the water-vapour permeability of grafts and artificial membranes used in the treatment of burns", Burns, 3, 159-165, 1977.
Barnett, A., et al., "Comparison of Synthetic Adhesive Moisture Vapor Permeable and Fine Mesh Gauze Dressings for Split-Thickness Skin Graft Donor Sites", The American Journal of Surgery, vol. 145, Mar. 1983, pp. 379-381.
Alper, J., et. al., "Moist wound healing under a vapor permeable membrane", Journal of the American Academy of Dermatology, vol. 8, No. 3, Mar. 1983, pp. 347-353.
James, J.H., et. al., "The use of Opsite, A Vapour Permeable Dressing, on Skin Donor Sites", British Journal of Plastic Surgery (1975), 28, 107-110.
Nahas, L.F., et al., "Use of Semipermeable Polyurethane Membrane for Skin Graft Dressings", Plastic and Reconstructive Surgery, Jun. 1981, pp. 791-792.
Edlich, R.F., et al., "Surgical Devices in Wound Healing Management", Wound Healing Biochemical & Clinical Aspects, W.B. Saunders Company, © 1992, pp. 581-599.
Orr, RK, et al., "Early Discharge After Mastectomy. A Safe Way of Diminishing Hospital Cost", Am Surg. Mar. 1987; 53(3) Abstract.
Otolaryngology, Head and Neck Surgery, The C.V. Mosby Company, © 1986, pp. 1716, 1724 and 2521.
Otolaryngology, vol. III, Head and Neck, W.B. Saunders Company, © 1980, pp. 2963.
Lore, Jr., J.M., "An Atlas of Head and Neck Surgery", Second Edition, vol. II, W.B. Saunders Company, Ó 1973.

Johnson, Frank E., "An Improved Technique for Skin Graft Placement Using a Suction Drain", pp. 585-586 (Dec. 1984).
Dewan, P.A., et al., "An Alternative Approach to Skin Graft Donor Site Dressing", Aust. N.Z. J. Surg. 1986, 56, 509-510.
Kohlman, P., et al., "Pouching Procedure to Collect Drainage From Around a Biliary Drainage Catheter", Ostomy/Wound Management, Nov./Dec. 1991, pp. 47-50, V. 37.
Alper, J., "Recent Advances in Moist Wound Healing", Southern Medical Journal, Nov. 1986, pp. 1398-1404, V. 79, N.11.
Reid, D., "Information on Cupping or Using Suction Cups on Wounds and for Healing Purposes", from Chines Herbal Medicine (2 pages).
Sheppard, M.D., "Sealed drainage of wounds," The Lancet, Jun. 14, 1952, pp. 1174-1176.
Putney, F., "The Use of Continuous Negative Pressure After Laryngectomy and Radical Neck Dissection", Surgery, Gynecology & Obstetrics, Aug. 1956, pp. 244-246.
Pleupump MK II, printouts from websites, www.xenamedical.se and www.landstinget.sormland.se, Aug. 14, 2001 (12 pages).
"Wound Suction; Better Drainage With Fewer Problems", Nursing75, October, pp. 52-55 (1975).
Grams Aspirator, et al., Grams Medical, catalog pages (3 pages) (prices as of Aug. 1991 and Sep. 1992).
Medela Dominant promotional literature (2 pages of photos) (labeled circa 1984-1985).
Engdahl, O., et al., "Quantification of Aspirated Air Volume Reduces Treatment Time in Pneumothorax", Eur Respir J., 1990, 3, pp. 649-652.
Usage Manual Pleurasug TDR (2 pages of diagrams with descriptions).
Spengler, M., et al., "Performance of Filtered Sump Wound Drainage Tubes", Surgery, Gynecology & Obstetricsq, Mar. 1982, pp. 333-336, vol. 154.
Hallstrom, B., et al., "Postoperative Course After Total Hip Arthroplasty: Wound Drainage Versus No Drainage", Orthopaedic Review, Jul. 1992, pp. 847-851.
Miles, W., et al., "A Method of Performing Abdominoperineal Excision for Carcinoma of the Rectum and of the Terminal Portion of the Pelvic Colon", The Lancet, Dec. 19, 1908, pp. 1812-1813.
Benjamin, P., "Faeculent Peritonitis: A Complication of Vacuum Drainage", Br. J. Surg., 1980, pp. 453-454, vol. 67.
Sagi, A., et al., "Burn Hazard From Cupping—An Ancient Universal Medication Still in Practice", Burns, 1988, pp. 323-325, vol. 14, No. 4.
Agrama, H., et al., "Functional Longevity of Intraperitoneal Drains", The American Journal of Surgery, Sep. 1976, pp. 418-421, vol. 132.
Magee, C., et al., "Potentiation of Wound Infection by Surgical Drains", The American Journal of Surgery, May 1976, pp. 547-549, vol. 131.
Birdsell, D., et al., "The Theoretically Ideal Donor Site Dressing",Annals of Plastic Surgery, Jun. 1979, pp. 535-537, vol. 2, No. 6.
Cruse, P., et al., "A Five-Year Prospective Study of 23,649 Surgical Wounds", Surgical Wounds/Cruse and Foord, Aug. 1973, pp. 206-210, vol. 107.
Aubrey, D., et al., "Treatment of the Perineal Wound After Proctectomy by Intermittent Irrigation", Arch. Surg., Oct. 1984, pp. 1141-1144, vol. 119.
Mayo, C., "The One-Stage Combined Abdominoperineal Resection for Carcinoma of the Rectum, Rectosigmoid and Sigmoid", Surgical Clinics of North America, Aug. 1939, pp. 1011-1019.
Draper, J., "Make the dressing fit the wound", Nursing Times, Oct. 9, 1985, pp. 32-35.
Schumann, D., et al., "Preoperative Measures to Promote Wound Healing", Nursing Clinics of North America, Dec. 1979, pp. 683-699, vol. 14, No. 4.
Besst, J., et al., "Wound Healing—Intraoperative Factors", Nursing Clinics of North America, Dec. 1979, pp. 701-712, vol. 14, No. 4.
Cooper, D., et al., "Postsurgical Nursing Intervention as an Adjunct to Wound Healing", Nursing Clinics of North America, Dec. 1979, pp. 713-726, Nursing Clinics of North America, vol. 14, No. 4.

(56) References Cited

OTHER PUBLICATIONS

O'Byrne, C., "Clinical Detection and Management of Postoperative Wound Sepsis", Nursing Clinics of North America, Dec. 1979, pp. 727-741, vol. 14, No. 4.
Keith, C., "Would Management Following Head and Neck Surgery", Nursing Clinics of North America, Dec. 1979, pp. 761-778, vol. 14, No. 4.
Tenta, L., et al., "Suction Drainage of Wounds of the Head and Neck", Surgery, Gynecology. & Obstetrics, Dec. 1989, p. 558, vol. 169.
Firlit, C., et al., "Surgical Wound Drainage: A Simple Device for Collection", journal of Urology, Aug. 1972, pp. 327, vol. 108.
Moloney, G., "Apposition and Drainage of Large Skin Flaps", Oxford, England, pp. 173-179 (Feb. 1957).
Worth, M., et al., "The Effectiveness of Bacterial Filtration in Vented Wound Drains", Journal of Surgical Research, 1979, pp. 405-407, 27.
Flynn, M., et al., "Promoting Wound Healing: Wound Healing Mechanisms", American Journal of Nursing, Oct. 1982, pp. 1544-1558.
Miles, W., "Technique of the Radical Operation for Cancer of the Rectum", The British Journal of Surgery, 1914-1915, pp. 292-305.
Hilton, P., "Surgical Wound Drainage: A Survey of Practices Among Gynaecologists in the British Isles", British Journal of Obstetrics and Gynaecology, Oct. 1988, pp. 1063-1069, vol. 95.
Milsom, I., et al., "An Evaluation of a Post-Operative Vacuum Drainage System", Current Medical Research and Opinion, 1979, pp. 160-164, vol. 6, No. 2.
Fox, J., et al., "The Use of Drains in Subcutaneous Surgical Procedures", The American Journal of Surgery, Nov. 1976, pp. 673-674, vol. 132.
Hilsabeck, J., "The Presacral Space as a Collector of Fluid Accumulations Following Rectal Anastomosis", American Society of Colon and Rectal Surgeons, (Oct. 1982), pp. 680-684, vol. 25, No. 7.
Hulten, L., et al., "Primary Closure of Perineal Wound After Protocolectomy or Rectal Excision", Acta Chir Scand 137, 1971, pp. 467-469.
Landes, R., "An Improved Suction Device for Draining Wounds", Arch. Surg., May 1972, pp. 707, vol. 104.
Hugh, T., "Abdominal Wound Drainage", The Medical Journal of Australia, May 4, 1987, pp. 505.
Eisenbud, D., "Modern Wound Management", Adadem Publishing, pp. 109-116 (Jan. 1999).
Eaglstein, W., et al., "Wound Dressings: Current and Future", Clinical and Experimental Approaches to Dermal and Epidermal Repair; Normal and Chronic Wounds, Progress in Clinical and Biological Research, vol. 365, © 1991 Wiley-Liss, Inc., pp. 257-265.
Bruno, P., "The Nature of Wound Healing", Nursing Clinics of North America, Dec. 1979, pp. 667-682, vol. 14, No. 4.
Bar-El, Y., et al., "Potentially Dangerous Negative Intrapleural Pressures Generated by Ordinary Pleural Drainage Systems", Chest, Feb. 2001, pp. 511-514, vol. 119, No. 2.
Agarwala, S., et al., "Use of Mini-Vacuum Drains in Small Surgical Wounds", Plastic and Reconstructive Surgery, Apr. 1998, pp. 1421-1422, vol. 101, n. 5.
Nasser, A., "The Use of the Mini-Flap Wound Suction Drain in Maxillofacial Surgery", Annals of the Royal College of Surgeons of England, 1986, pp. 151-153, vol. 68.
Hunt, T.K., et al. eds., "Dead Space" and "Drainage", Fundamentals of Wound Management, pp. 416-447 (1979).
Lumley, J., et al., "The Physical and bacteriological Properties of Disposable and Non-Disposable Suction Drainage Units in the Laboratory", Br. J. Surg., 1974, pp. 832-837, vol. 61.
Britton, B., et al., "A Comparison Between Disposable and Non-disposable Suction Drainage Units: A Report of a Controlled Trial", Br. J. Surg., 1979, pp. 279-280, vol. 66.
McFarlane, R., "The use of Continuous Suction Under Skin Flaps", British Journal of Plastic Surgery, pp. 77-86 (1958-1959).
Fay, M., "Drainage Systems: Their Role in Wound Healing", AORN Journal, Sep. 1987, pp. 442-455, vol. 46, No. 3.
Taylor, V., "Meeting the Challenge of Fistulas & Draining Wounds", Nursing80, June, pp. 45-51.
Orgill, D., "Curent Concepts and Approaches to Would Healing", Critical Care Medicine, Sep. 1988, pp. 899-908, vol. 16, No. 9.
Part III. Resolving Selected Clinical Dilemmas, pp. 17-20.
"Making Sense of Wound Drainage", Nursing Times, Jul. 5, 1989, pp. 40-42, vol. 85, No. 27.
Manualectric Breastpump, Catalog pages (4 pages), diagrams and descriptions.
Harkiss, K., "Leg Ulcers Cheaper in the Long Run", Community Outlook, Aug. 1985, pp. 19, 21, 22, 24 & 26.
Westaby, S. (Editor), "Wound Care No. 43; Which Dressing and Why", Nursing Times Jul. 21, 1982, pp. 41-44.
OpSite Wound Dressings, "Do Your Pressure Sore Dressings Shape Up to the OpSite Standard", 2 pages of advertisements.
Dow Corning Silastic® Foam Dressing: A New Concept in the Management of Open Granulating Wounds, 2 pages of advertisements.
Cobb, J., "Why Use Drains", The Journal of Bone and Joint Surgery, Nov. 1990, pp. 993-995, vol. 72-B, No. 6.
PLEUR$_x$ Pleural Catheter, Denver Biomedical, 4 pages of brochure.
Silvis, R., et al., "The Use of Continuous Suction Negative Pressure Instead of Pressure Dressing", Annals of Surgery, Aug. 1955, pp. 252-256, vol. 142, No. 2.
Van Way, C., "Prevention of Suction-Induced Gastric Mucosal Damage in Dogs", Gastric Suction, 1987, pp. 774-777, vol. 15, No. 8.
Moserova, J., "The Healing and Treatment of Skin Defects", pp. 103-151 (1989).
Rabkin, J., et al., "Infection and Oxygen", Problem Wounds: The Role of Oxygen, pp. 1-15 (1987).
Paradise Valley Hospital, The Center for Wound Healing and Hyperbaric Medicine, 3 pages of brochure.
DuoDERM Hydroactive™ Dressing, "In wound management—Now, a proven environment for fast healing", 1 page advertisement.
Howmedica porto-vac®, "Gentle, Steady Wound Drainage", 1 page advertisement.
Silicone from CUI (Cox-Uphoff International), "Flexability", 1 page advertisement.
Curtin, L., "Wound Management: Care and Cost—An Overview", Nursing Management, Feb. 1984, pp. 22-25, vol. 15.
Grabowski, S., "Leczenie ran z zastosowaniem podcisnienia", article, pp. 19-21, English abstract on p. 21 and 1 sheet printout from PubMed, (Jan. 1, 1964).
Royle, G., et al., "Disposable Drains", Annals of the Royal College of Surgery of England, 1984, 1 page, vol. 66.
Meehan, P., "Open Abdominal Wounds: A Creative Approach to a Challenging Problem", Pregressions, 1992, pp. 3-8, 11, vol. 4, No. 2.
Stansby, G., et al., "Vacuum Drainage of Groin Wounds After Vascular Surgery", Br. J. Surg., Oct. 1990, pp. 1194-1195, vol. 77, No. 10.
Edlich, R., et al., "Evaluation of a New, Improved Surgical Drainage System", The American Journal of Surgery, Feb. 1985, pp. 295-298, vol. 149.
Broader, J., et al., "Management of the Pelvic Space After Proctectomy", Br. J. Surg., 1974, pp. 94-97, vol. 61.
Ayoub, M., et al., "A study of cutaneous and intracompartmental limb pressures associated with the combined use of tourniquets and plaster casts", May 1986, pp. 497, vol. 68-B, No. 3.
Cooper, D., "Optimizing Wound Healing: A Practice Within Nursing's Domain", Nursing Clinics of North America, Mar. 1990, pp. 165-180, vol. 25, No. 1.
Cooper, D., "Wound Healing", Nursing Clinics of North America, pp. 163-164 (Mar. 1990).
Hollis, H., et al., "A Practical Approach to Wound Care in Patients With Complex Enterocutaneous Fistulas", Surgery, Gynecology & Obstetrics, Aug. 1985, pp. 178-180, vol. 161.
Fingerhut, A., "Passive vs. Closed Suction Drainage After Perineal Would Closure Following Abdominoperineal Rectal Excision for Carcinoma", Dis Colon Rectum, Sep. 1995, pp. 926-932, vol. 38, No. 9.
Cook Pneumothorax Catheter Set, Wayne Pneumothorax Catheter Set, Emergency Medicine, Videotape advertisement.
Schaffer, D., "Closed Suction", Nursing97, 64. Nov., http://www.springnet.com, pp. 62-64.
Carroll, P., "The Principles of Vacuum and Its Use in the Hospital Environment", Ohmeda, pp. 1-30 and cover sheet.

(56) References Cited

OTHER PUBLICATIONS

Murray, J., et al., "On the Local and General Influence on the Body if Increased and Diminished Atmospheric Pressure", The Lancet, V. 1, 1834-1835, pp. 909-917.

Herrmann, L., et al., "The Conservative Treatment of Arteriosclerotic Peripheral Vascular Diseases", pp. 750-760 (Oct. 1934).

Versatile 1 Wound Vacuum System™ for The Promotion of Wound Healing, Wound Application instructions, 1 page advertisement.

Bluesky Medical "The Versatile One!™", Wound Drainage and More, 1 page advertisement. (Labeled Spring 2003).

Chariker-Jeter® Wound Sealing Kit, Would Application Instructions, 1 page advertisement.

Thomas, S., et al., "Comparative Review of the Properties of Six Semipermeable Film Dressings", The Pharmaceutical Journal, Jun. 18, 1988, pp. 785-789.

Baker, B., "Abundance of Web Sites on Wound Care Management", Family Practice News, Mar. 1, 2000, pp. 52.

Cosker, T., et al., "Choice of Dressing Has a Major Impact on Blistering and Healing Outcomes in Orthopaedic Patients", Journal of Wound Care, Vo. 14, No. 1, Jan. 2005, pp. 27-29.

Townsend, P.L.G., "The Quest for a Cheap and Painless Donor-Site Dressing", Burns, 2, pp. 82-85 (Jan. 1976).

Langworthy, M., et al., "Treatment of the Mangled Lower Extremity After a Terrorist Blast Injury", Clinical Orthopaedics and Related Research, No. 422, pp. 88-96 (May 2004).

Park, G.B., et al., "The Design and Evaluation of a Burn Wound Covering", Supplied by the British Library—"The Word's Knowledge", pp. 11-15 (1978).

ACU-derm® Transparent Moisture Vapor Permeable Polyurethane Dressing, pp. 1-13 and cover sheet.

3M Ioban 2, Breathability, Conformability and Strength, Breathability—Moisture Vapor Transmission Rate and Conformability and Strength—Tensile Strength, Elongation and Fn Modulus Test (1 page).

smith&nephew website printout, Would Management, FAQs.

"Moist Wound Dressings" from Physicians Instruction Book for Moist Wound Healing.

PCT/US08/79364—Written Opinion and International Search Report P04263WO0—ISR (Dec. 16, 2008).

PCT/US08/79364—International Report on Patentability P04263WO0—IPRP (Apr. 13, 2010).

PCT/US03/16763—Written Opinion, International Preliminary Examination Report, and International Search Report, P02915WO0—ISR (Dec. 18, 2003, Apr. 19, 2004, and Sep. 2, 2004).

PCT/US08/30581—International Report on Patentability P04486WO0—IPRP (Jul. 22, 2010).

PCT/US09/50806—Written Opinion and International Search Report P04165WO0—ISR_WO (Sep. 15, 2009).

PCT/US09/50806—International Report on Patentability P04165WO0—IPRP (Jan. 27, 2011).

Wilson, J.L., et al., "Loss of blood volume in spinal surgery with use of closed wound suction: an experimental study", Southern Med. J., 61:761-763, (Jul. 1968), read before the Section on Orthopaedic and Traumatic Surgery, Southern Medical Association, 61st Annual Meeting, Miami Beach, FL., (Nov. 13-16, 1967).

Erdmann, D., et al., "Abdominal wall defect and enterocutaneous fistula treatment with the vacuum-assisted closure (VAC) system", Plast. Reconstruct. Surg., 108(7):2066-8 (Dec. 2001).

Van Susante, J.L.C., et al., "Linkage of chondroitin-sulfate to type I collagen scaffolds stimulates the bioactivity of seeded chondrocytes in vitro," Biomaterials, 22:2359-2369 (2001).

Wang, Y., et al., "A tough biodegradable elastomer," Nature Biotechnology, 20:602-606 (Jun. 2002).

Sasaki, N., et al., "Stress-strain curve and Young's Modulus of a collagen molecule as determined by the x-ray diffraction technique," J. Biomechanics, 29(5):655-658 (1996).

Nagata, M., et al., "Synthesis, characterization, and enzymatic degradation of network aliphatic copolyesters," Journal of Polymer Science: Part A: Polymer Chemistry, 37:2005-2011 (1999).

Causa, F., et al., "A multi-functional scaffold for tissue regeneration: The need to engineer a tissue analogue," Biomaterials, 28(34):5093-5099 (Dec. 2007; available online Aug. 6, 2007).

Nair, L.S., et al., "Development of novel tissue engineering scaffolds via electrospinning," Expert Opin. Biol. Ther. 4 (5):659-668 (May 2004), (2 sheets), abstract.

Webb, A.R., et al., "Biodegradable polyester elastomers in tissue engineering," Expert Opin. Biol. Ther. 4(6):801-812 (2004).

Zhong, S.P., et al., "Development of a novel collagen-GAG nanofibrous scaffold via electrospinning," Materials Science and Engineering: C, 27(2):262-266 (Mar. 2007) (available online Jun. 8, 2006).

Li, C., et al., "Electrospun silk-BMP-2 scaffolds for bone tissue engineering," Biomaterials, 27(16):3115-3124 (Jun. 2006) (available online Feb. 3, 2006).

Teo, W.E, et al., "Electrospun scaffold tailored for tissue-specific extracellular matrix," Biotechnology Journal, 1 (9):918-929 (Sep. 2006) (published online Aug. 28, 2006).

Yi, F., et al., "Poly(glycerol sebacate) nanofiber scaffolds by core/shell electrospinning," Macromol. Biosci. 8:803-806 (2008).

Wang, Y., et al., "In vivo degradation characteristics of poly(glycerol sebacate)," J. Biomed Mater Res A, 66 (1):192-197 (Jul. 1 2003) (published online Jun. 10, 2003).

Ifkovits, J.L., et al., "Biodegradable and radically polymerized elastomers with enhanced processing capabilities," Biomed Mater. 3(3):034104 (Sep. 2008) (published Aug. 8, 2008).

Venugopal, J.R., et al., "Nanobioengineered electrospun composite nanofibers and osteoblasts for bone regeneration," Artif. Organs 32(5):388-397 (2008).

Heydarkhan-Hagvall, S., et al., "Three-dimensional electrospun ECM-based hybrid scaffolds for cardiovascular tissue engineering," Biomaterials 29(19):2907-2914 (Jul. 2008; available online Apr. 9, 2008).

Chen, D., et al., "Application of electrostatic spinning technology in nano-structured polymer scaffold," Zhongguo Xiu Fu Chong Jian Wai Ke Za Zhi, 21(4):411-415 (Apr. 2007), 1 sheet abstract.

Qiu, H., et al., "A citric acid-based hydroxyapatite composite for orthopedic implants," Biomaterials 27:5845-5854 (2006) (available online Aug. 21, 2006).

Nair, L.S., et al., "Nanofibers and nanoparticles for orthopaedic surgery applications," J. Bone Joint Surg. Am. 90 (Supp. 1):128-131 (2008).

Abdel-Fattah, W.I., et al., "Synthesis, characterization of chitosans and fabrication of sintered chitosan microsphere matrices for bone tissue engineering," Acta Biomaterialia 3:503-514 (2007).

Li, M., et al., "Co-electrospun poly(lactide-co-glycolide), gelatin, and elastin blends for tissue engineering scaffolds," J. Biomed. Mater. Res. A. 79(4):963-973 (Dec. 15, 2006) (published online Aug. 31, 2006).

Li, M., et al., "Electrospun blends of natural and synthetic polymers as scaffolds for tissue engineering," Conf. Proc. IEEE Eng. Med. Biol. Soc. 6:5858-5861 (2005), 1 sheet abstract.

Yang, X., et al., "Multifunctional nanofibrous scaffold for tissue engineering," Journal of Experimental Nanoscience 3 (4):329-345 (2008).

Yang, J., et al., "Synthesis and evaluation of poly(diol citrate) biodegradable elastomers," Biomaterials 27:1889-1898 (2006; available online Nov. 15, 2005).

Yoshimoto, H., et al., "A biodegradable nanofiber scaffold by electrospinning and its potential for bone tissue engineering," Biomaterials 24(12):2077-2082 (May 2003).

Ndreu, A., et al., "Electrospun biodegradable nanofibrous mats for tissue engineering," Nanomedicine (Lond.) 3 (1):45-60 (Feb. 2008), 1 sheet abstract.

Kim, S.S., et al., "Accelerated bonelike apatite growth on porous polymer/ceramic composite scaffolds in vitro," Tissue Eng. 12(10):2997-3006 (Oct. 2006).

Li, M., et al., "Electrospun protein fibers as matrices for tissue engineering," Biomaterials 26(30):5999-6008 (Oct. 2005) (available online May 13, 2005).

Kidoaki, S., et al., "Mesoscopic spatial designs of nano- and microfiber meshes for tissue-engineering matrix and scaffold based

(56) References Cited

OTHER PUBLICATIONS on newly devised multilayering and mixing electrospinning techniques," Biomaterials 26(1):37-46 (Jan. 2005) (available online Mar. 2, 2004).
Ma, Z., et al., "Potential of nanofiber matrix as tissue-engineering scaffolds," Tissue Engineering 11(1/2):101-109 (2005).
Faria, M.L.E., et al., "Recombinant human bone morphogenetic protein-2 in absorbable collagen sponge enhances bone healing of tibial osteotomies in dogs," Veterinary Surgery 36(2):122-131 (Feb. 2007; first published online Mar. 2, 2007).
Li, W.J., et al., "Fabrication and characterization of six electrospun poly(alpha-hydroxy ester)-based fibrous scaffolds for tissue engineering applications," Acta Biomater 2(4):377-385 (Jul. 2006; published online May 6, 2006).
Smith, L.A., et al., "Nano-fibrous scaffolds for tissue engineering," Colloids and Surfaces B: Biointerfaces 39 (3):125-131 (Dec. 10, 2004; available online Feb. 4, 2004).
Wang, W., et al., "Biodegradable polyurethane based on random copolymer of L-lactide and ε-caprolactone and its shape-memory property," J. Appl. Polym. Sci. 104:4182-4187 (2007).
Chronakis, I.S., "Novel nanocomposites and nanoceramics based on polymer nanofibers using electrospinning process—A review," Journal of Materials Processing Technology 167:283-293 (2005).
Guan, J., et al., "Preparation and characterization of highly porous, biodegradable polyurethane scaffolds for soft tissue applications," Biomaterials 26:3961-3971 (2005; available online Dec. 8, 2004).
Kim, H.W., et al., "Bioactive glass nanofiber-collagen nanocomposite as a novel bone regeneration matrix," J. Biomed. Mater. Res. A 79:698-705 (2006; published online Jul. 18, 2006).
Nair, L.S., et al., "Biodegradable polymers as biomaterials," Prog. Polym. Sci. 32:762-798 (2007; available online Jun. 11, 2007).
Zhang, Y., et al., "Electrospun biomimetic nanocomposite nanofibers of hydroxyapatite/chitosan for bone tissue engineering," Biomaterials 29:4314-4322 (2008; available online Aug. 20, 2008).
Wan, Y., et al., "Biphasic scaffold for annulus fibrosus tissue regeneration," Biomaterials 29:643-652 (2008; available online Nov. 13, 2007).
Um, I.C., et al., "Electro-spinning and electro-blowing of hyaluronic acid," Biomacromolecules 5:1428-1436 (2004; published online May 7, 2004).
Boland, E.D., et al., "Electrospinning polydioxanone for biomedical applications," Acta Biomaterialia 1:115-123 (2005).
U.S. Appl. No. 12/351,331 (Mar. 26, 2011).
Harkiss, K., "Leg ulcers cheaper in the long run", Community Outlook, pp. 19, 21, 22 (Aug. 14, 1985).
Argenta, L.C., et al., "Vacuum-assisted closure: state of clinic art", Plast. Reconstr. Surg., 117 (7 Suppl.): 127S-142S (Jun. 2006).
Chung, C.J., et al., "Case review: management of life-threatening sepsis and wound healing in a Klippel-Trenaunay patient using serial surgical debridements and vacuum-assisted closure", Eur. J. Plast. Surg., 26:214-216 (2003).
Dedmond, B.T., et al., "Subatmospheric pressure dressings in the temporary treatment of soft tissue injuries associated with type III open tibial shaft fractures in children", J. Pediatr. Orthop., 26(6):728-732, (Nov.-Dec. 2006).
Dedmond, B.T., et al., "The use of negative-pressure wound therapy (NPWT) in the temporary treatment of soft tissue injuries associated with high-energy open tibial shaft fractures", J. Orthop. Trauma, 21(1):11-17, (Jan. 2007).
Gemeinhardt, K.D., et al., "Vacuum-assisted closure for management of a traumatic neck wound in a horse", Equine Veterinary Education, 17(1):27-33, (2005).
Laverty, D., et al., "Negative pressure wound therapy in the management of orthopedic wounds", Ostomy Wound Manage., 50(11A suppl):18S-9S (Nov. 2004).
Molnar, J.A., "Applications of negative pressure wound therapy to thermal injury", Ostomy Wound Manage., 50(4A suppl):17-9 (Apr. 2004).
Molnar, J.A., "The science behind negative pressure wound therapy", Ostomy Wound Manage., 50 (4A suppl):2-5 (Apr. 2004).
Molnar, J.A., et al., "Management of an acute thermal injury with subatmospheric pressure", J. Burns Wounds, 4:83-92, 4:e5 (published online Mar. 24, 2005).
Morykwas, M.J., et al., "Effects of varying levels of subatmospheric pressure on the rate of granulation tissue formation in experimental wounds in swine", Ann. Plast. Surg., 47(5):547-551 (Nov. 2001).
Plikaitis, C.M., et al., "Subatmospheric pressure wound therapy and the vacuum-assisted closure device: basic science and current clinical successes", Expert Rev. Med. Devices, 3(2):175-184, (Mar. 2006).
Schlatterer, D., et al., "Orthopedic indications for negative pressure wound therapy", Ostomy Wound Manage., 51 (2A suppl):27S-8S (Feb. 2005).
Schneider, A.M., et al., "Re: use of specialized bone screws for intermaxillary fixation: reply", Ann. Plast. Surg., 47 (1): 93, (Jul. 2001).
Webb, L.X., et al., "The contaminated high-energy open-fracture: a protocol to prevent and treat inflammatory mediator storm-induced soft-tissue compartment syndrome (IMSICS)", J. Am. Acad. Orthop. Surg., 14(10):SA82-S86 (Oct. 2006).
Yang, C.C., et al., "Vacuum-assisted closure for fasciotomy wounds following compartment syndrome of the leg", J. Surg. Orthop. Adv., 15(1):19-23 (Spring 2006).
Argenta, A., et al., "Deformation of superficial and deep abdominal tissues with application of a controlled vacuum", European Tissue Repair Society, Focus group meeting Topical Negative Pressure (TNP) Therapy, London UK ( Dec. 4-6, 2003).
Argenta, L.C., et al., "The V.A.C. as an adjunct for treatment for abdominal wounds", 66th Annual Meeting of the American Society of Plastic and Reconstructive Surgeons, San Francisco, CA, pp. 330-331; 1 sheet of abstract (Sep. 21-24, 1997).
Argenta, L.C., et al., "Vacuum assisted closure of chronic wounds", 65th Annual Scientific Meeting, American Society of Plastic and Reconstructive Surgeons, Dallas, TX, pp. 226-227; 1 sheet of abstract (Nov. 9-13, 1996).
Defranzo, A.J., et al., "The use of V.A.C. therapy for treatment of lower extremity wounds with exposed bone", 68th Annual Meeting of the American Society of Plastic and Reconstructive Surgeons, New Orleans, LA, pp. 37-38; 2 sheets of abstract (Oct. 24-27, 1999).
Kortesis, B., et al., "Vacuum-assisted closure for the treatment of open tibia fractures", 72nd Annual Meeting of the American Society of Plastic Surgeons, San Diego, CA, pp. 172-173; 1 sheet of abstract (Oct. 25-29, 2003).
Kremers, L., et al., "Effect of topical sub-atmospheric pressure treatment on angiotensin I and II levels post burn", 35th Annual Meeting, Abstract printed in J. Burn Care Rehabilitation, p. S44, Abstract No. 3 American Burn Association, Miami, Florida (Apr. 1-4, 2003).
Kremers, L., et al., "Serum interleukin levels post burn with and without application of sub-atmospheric pressure", 35th Annual Meeting, Abstract printed in Burn Care Rehabilitation, p. S43, Abstract No. 2, American Burn Association, Miami, Florida, (Apr. 1-4, 2003).
Molnar, J.A., et al., "Improved skin graft adherence and vascularization of integra(R) using subatmospheric pressure—a laboratory study", Abstract printed in Burn Care & Rehabilitation, p. S111, Abstract No. 141; American Burn Meeting, 34th Annual Meeting, Chicago, IL, (Apr. 24-27, 2002).
Morykwas, M.J., et al., "Negative pressure treatment of burned extremities", 65th Annual Scientific Meeting, American Society of Plastic and Reconstructive Surgeons, Dallas, TX, pp. 86-87; 1 sheet of abstract (Nov. 9-13, 1996).
Morykwas, M.J., et al., "The effect of V.A.C.(TM) therapy on the length of stay, total charges and average daily charge for patients assigned to DRG 263: analysis of 13 consecutive quarters", presented in part at the 28th Annual Conference of the Wound, Ostomy, and Continence Nurses Society, Seattle, WA, (15 sheets) (Jun. 15-19, 1996).
Park, C.A., et al., "Outpatient use of Integra® and subatmospheric pressure in the management of wound and burn reconstruction", J. Burn Care Rehabil., 26(2 suppl.):S113, Chicago, IL, (May 10-13, 2005).
Schneider, A.M., et al., "Muscle flap survival after complete venous occlusion by application of a negative pressure device", 66th Annual

(56) References Cited

OTHER PUBLICATIONS

Meeting of the American Society of Plastic and Reconstructive Surgeons, San Francisco, CA, pp. 300-302; 2 sheets of abstract (Sep. 21-24, 1997).
Schneider, A.M., et al., "Treatment of brown recluse spider bite wounds by external application of sub-atmospheric pressure", 68th Annual Meeting of the American Society of Plastic and Reconstructive Surgeons, New Orleans, LA, p. 35; 1 sheet of abstract (Oct. 24-27, 1999).
Webb, L.X., "Use of negative pressure devices in highly contaminated, high energy wounds", Extremity War Injuries: State of the Art and Future Directions, AAOS/OTA Extremity War Injures Symposium, Jan. 24-27, 2006, [Abstract].
Morykwas, M.J., "Basic Research and Animal Studies," Presentation at the European Topical Negative Pressure Meeting in Salsbury, England, (Jun. 2005).
Defranzo, A.J., et al., "Vacuum assisted closure of the abdominal wall", 73rd Annual Meeting, American Association of Plastic Surgeons, Philadelphia, PA (2004), 1 sheet of abstract.
Fleischmann, W., et al., "Vacuum assisted closure of wounds following dermatofasciotomy of the leg", Unfallchirurg., (English abstract on p. 284, and 1 sheet printout from PubMed); 99(4):283-7, (Apr. 1996).
Ford, C.N., et al., "Interim analysis of a prospective, randomized trial of vacuum-assisted closure versus the healthpoint system in the management of pressure ulcers", Ann. Plast. Surg., (11 sheets); 49(1):55-61 (Jul. 2002).
Gouttefangeas, C., et al., "Functional T lymphocytes infiltrate implanted polyvinyl alcohol foams during surgical wound closure therapy," Clin. Exp. Immunol., 124(3):398-405 (Jun. 2001).
Greer, S.E., et al., "Subatmospheric pressure dressing for saphenous vein donor-site complications," Ann. Thorac. Surg., (6 sheets); 71(3):1038-40 (Mar. 2001).
Hawkins-Bradley, B., et al., "Treatment of a nonhealing wound with hypergranulation tissue and rolled edges", J. Wound Ostomy Continence Nurs., 29(6):320-324 (Nov. 2002).
Harlan, J.W., "Treatment of open sternal wounds with the vacuum-assisted closure system: a safe, reliable method", Plast. Reconstruct. Surg., 109(2):710-12 (Feb. 2002).
Hartnett, S., "Heparin-induced thrombocytopenia as the cause of gluteus muscle necrosis: a case study describing the benefits of multidisiplinary physical and psychosocial interventions", Ostomy Wound Manage., 47(5):18-26 (May 2001).
Hersh, R.E., et al., "A technique for the treatment of sternal infections using the vacuum assisted closure™ device", Heart Surg. Forum, 4(3):211-15 (2001).
Ingber, D.E., "Mechanical signaling and the cellular response to extracellular matrix in angiogenesis and cardiovascular physiology", Circ. Res., 91:877-887 (Nov. 15, 2002).
Kalailieff, D., "Vacuum-assisted closure: wound care technology for the new millennium", Perspectives, 22(3):28-9 (Fall 1998).
Kercher, K.W., et al., "Successful salvage of infected PTFE mesh after ventral hernia repair", Ostomy Wound Manage., 48(10):40-5 (Oct. 2002).
Kiernan, M., "The process of granulation and its role in wound healing", Community Nurse, 5(5):47-48 (Jun. 1999).
Kloth, L.C., "5 questions- and answers- about negative pressure wound therapy", Adv. Skin Wound Care, 15(5):226, 228-9 (Sep.-Oct. 2002).
Kusel, C., "Use of V.A.C. (vacuum-assisted closure) therapy in general surgery: problem wounds deprived of air", Pflege Z., (and 1 sheet printout from PubMed); 55(6):408-412 (Jun. 2002).
Labler, L., et al., "Vacuum sealing of problem wounds", Swiss Surg., (English abstract on first page, 1 sheet printout from PubMed); 8(6):266-7 (2002).
Marston, W.A., et al., "The efficacy and safety of Dermagraft in improving the healing of chronic diabetic foot ulcers: results of a prospective randomized trial", Diabetes Care, 26(6) 10 pp., (Exhibit 271) (Jun. 1, 2003).

Mendez-Eastman, S., "New treatment for an old problem: negative-pressure wound therapy", Nurs., 32(5):58-64. (12 sheets) (May 2002).
Muller, G., "Vacuum dressing in septic wound treatment", Langenbecks Arch. Chir. Suppl. Kongressbd., (English abstract on p. 537, and 1 sheet printout from PubMed); 114:537-41 (1997).
Banwell, P.E., et al., "Topical negative pressure (TNP): the evolution of a novel wound therapy," J. Wound Care, 12 (1):22-8 (Jan. 2003).
Cardozo, M., "A case study of holistic wound management in intensive care", Br. J. Nurs., 12(11 Suppl):S35-37, S40-42 (Jun. 2003).
Collier, M., "Topical negative pressure therapy", Nurs. Times, 99(5):54-5 (Feb. 4-10, 2003).
Domkowski, P.W., et al., "Evaluation of vacuum-assisted closure in the treatment of poststerotomy mediastinitis," J. Thorac. Cardiovasc. Surg., 126(2):386-90 (Aug. 2003).
Eginton, M.T., et al., "A prospective randomized evaluation of negative-pressure wound dressings for diabetic foot wounds", Ann. Vasc. Surg., 17(6):645-9 (2003).
Ferreira, M.C., et al., "The vacuum assisted closure of complex wounds: report of three cases", Rev. Hosp. Clin. Fac. Med. S. Paulo, 58(4):227-30 (2003).
Fisher, A., et al., "Vacuum assisted wound closure therapy", Issues Emerg. Health Technol., Issue 44, 6 pp. (Mar. 2003).
Hallberg, H., et al., "Vaginal construction with skin grafts and vacuum-assisted closure", Scand. J. Plast. Reconstr. Surg. Hand Surg., 37(2):97-101 (2003).
Hess, C.L., et al., "A review of mechanical adjuncts in wound healing: hydrotherapy, ultrasound, negative pressure therapy, hyperbaric oxygen, and electrostimulation", Ann. Plast. Surg., 51(2):210-8 (Aug. 2003).
Hodzic, J., et al., "Vacuum sealing of extensive wound healing disorders after kidney transplantation," Urologe A., (6 sheets in German, English abstract on p. 2 and 1 sheet printout from PubMed); 42(8):1097-100 (Aug. 2003) (Epub Apr. 3, 2003).
Kaufman, M.W., et al., "Vacuum-assisted closure therapy: wound care and nursing implications", Dermatol. Nurs., 15 (4):317-20, 323-236 (Aug. 2003).
Luckraz, H., et al., "Vacuum-assisted closure as a treatment modality for infections after cardiac surgery", J. Thorac. Cardiovasc. Surg., 125(2):301-5 (Feb. 2003).
McGuinness, J.G., et al., "Vacuum-assisted closure of a complex pilonidal sinus", Dis. Colon Rectum, 46(2):274-6 (Feb. 2003).
Moran, S.G., et al., "Vacuum-assisted complex wound closure with elastic vessel loop augmentation: a novel technique", J. Wound Care, 12(6):212-3 (Jun. 2003).
Schipper, J., et al., "The preconditioning and prelamination of pedicled and free microvascular anastomised flaps with the technique of vacuum assisted closure", Laryngorhinootologie, (English abstract on first page, and 2 sheets printout from PubMed); 82(6):421-7, (Jun. 2003).
Shi, B., et al., "Effects of vacuum-assisted closure (VAC) on the expressions of MMP- 1, 2, 13 in human granulation wound", Zhonghua Zheng Xing Wai Ke Za Zhi, (English abstract on first page and 1 sheet printout from PubMed); 19 (4):279-81 (Jul. 2003).
Silver, F.H., et al., "Mechanobiology of force transduction in dermal tissue", Skin Res. Technol., 9(1):3-23 (Feb. 2003).
Silver, F.H., et al., "Mechanosensing and mechanochemical transduction: how is mechanical energy sensed and converted into chemical energy in an extracellular matrix?" Crit. Rev. Biomed. Eng., 31(4):255-331 (2003).
Skillman, J., et al., "Vacuum assisted closure (VAC) dressing for skin graft application following exenteration of the orbit", Orbit, 22(1):63-5 (Mar. 2003).
Song, D.H., et al., "Vacuum assisted closure for the treatment of sternal wounds: the bridge between debridement and definitive closure", Plast. Recontr. Surg., 111(1):92-7 (Jan. 2003).
Wanner, M.B., et al., "Vacuum-assisted wound closure for cheaper and more comfortable healing of pressure sores: a prospective study", Scand. J. Plast. Reconstruct. Surg. Hand Surg., 37(1):28-33 (2003).
Weaver, B. "The nursing needs of a patient with a complicated abdominal wound", Prof. Nurse, 18(5):269-73 (Jan. 2003).

(56) References Cited

OTHER PUBLICATIONS

Wongworawat, M.D., et al., "Negative pressure dressings as an alternative technique for the treatment of infected wounds", Clin. Orthop. Relat. Res., (414):45-8 (Sep. 2003).
Baker, E.A., et al., "Growth factor profiles in intraperitoneal drainage fluid following colorectal surgery: relationship to wound healing and surgery", Wound Rep. Reg., 11(4):261-267, (Jul.-Aug. 2003).
Morykwas, M.J., "Use of sub-atmospheric pressure to prevent adriamycin extravasation ulcers in a pig model", first presented at The 44th Annual Meeting of Plastic Surgery Research Council, Pittsburg, PA, (May 22-26, 1999).
"The Remington Report: Business and clinical strategies for home care executives", containing articles by J.A. Molnar, D.G. Armstrong, et al., and S. Mendez-Eastman; (Nov. / Dec. 2004).
Thomas, S., "Wound management and dressings," cover sheet, preface, sheet labeled "Chapter 5" and pp. 36-39 (1990). MolnlyckeDEWH1-003.
Morykwas, M.J., et al., "Use of Negative Pressure to Increase the Rate of Granulation Tissue Formation in Chronic Open Wounds", The FASEB Journal, (799-800), Feb. 19, 1993.
Orringer, J.S., et al., "Management of Wounds in Patients with Complex Enterocutaneous Fistulas", Surgery, Gynecology & Obstetrics, Jul. 1987, vol. 165.
Swearingen, P.L., "The Addison-Wesley Photo-Atlas of Nursing Procedures", 9 pages, © 1984.
Mulder, G.D, et al., Clinicians' Pocket Guide to Chronic Wound Repair, Wound Healing Publications Second Edition, 1992, pp. 1-107.
Peacock, E.E., Jr., Wound Repair:, Repair of Skin Wounds, 1984, pp. 172-175.
Healing of Full Thickness Defects in Swine.
Webster, J.G., "Prevention of Pressure Sores", © IOP Publishing Ltd 1991, The Adam Hilger Series on Biomedical Engineering, pp. 199-223.
Garcia-Velasco, M., et al., "Compression Treatment of Hypertrophic Scars in Burned Children", The Canadian Journal of Surgery, V.21, No. 5, Sep. 1978, pp. 450-452.
Rose, M.P., et al., "The Clinical Use of a Tubular Compression Bandage, Tubigrip, for Burn-Scar Therapy: A Critical Anaylis", Burns (1985) 12, 58-64.
Murray, Y., "Tradition Rather Than Cure", Wound Care, Nursing Times, Sep. 21, vol. 84, No. 38, 1988.
Spurlock, Gareth, "The Management of Open Joint Injuries", Wound Management, Veterinary Clinics of North American Equina Practice, vol. 5, No. 3, Dec. 1989.
Tittel, K., et al., "VariDyne—new standards in postoperative wound drainge", Jahrgang 14 (1988), Nr. 2, April, vol. 14 (1988), No. 2, April, pp. 104-107.
Queen, D., et al., "The preclinical evaluation of the Water Vapour Transmission Rate Through Burn Wound Dressings", Biomaterials 1987 vol. 8, September, pp. 367-371.
Wood, R.A.B., et al., "Foam Elastomer Dressing in the Management of Open Granulating Wounds: Experience with 250 Patients", Br. J. Surg., vol. 64 (1977), pp. 554-557.
Waymack, J.P., et al., "An Evaulation of Aquaphor Gauze Dressing in Burned Children", Burns (1986) 12, 443-448.
Winter, George D., "Epidermal Wound Healing Under a New Polyurethane Foam Dressing (Lyofoam)", Plastic & Reconstructive Surgery, Nov. 1975, Vo. 56, No. 5, pp. 531-537.
Banwell, P, et al., "Topical Negative Pressure TNP Focus Group Meeting", Proceedings, London, UK 2003, pp. 1-111.
Proceedings from the 2003 National V.A.C.® Education Conference, supplement to the Apr. 2004 WOUNDS, 40 pages.
Dieu, T., et al., "Too Much Vacuum-Assisted Closure", ANZ J. Surg. 2003; 73: 1057-1060.
Chester, D., et al., "Adverse Alteration of Wound Flora with Topical Negative-Pressure Therapy: A Case Report", British Journal of Plastic Surgery, 2002, pp. 510-511.
Alvarez, A., et al., "Vacuum-Assisted Closure for Cutaneous Gastrointestinal Fistula Management", Gynecologic Oncology, 80, 413-416 (2001).
Nienhuijs, S.W., et al., "Can Topical Negative Pressure Be Used to Control Complex Enterocutaneous Fistulae?", Journal of Wound Care, V. 12, No. 9, Oct. 2003, pp. 343-345.
Erdmann, D., et al., "Abdominal Wall Defect and Enterocutaneous Fistula Treatment with the Vacuum-Assisted Closure (V.A.C.) System", Plastic and Reconstructive Surgery, vol. 108, No. 7, pp. 2066-2068 (Dec. 2001).
Lohman, R., et al., "DISCUSSION: Vacuum Assisted Closure: Microdeformations of Wounds and Cell Proliferation", Plastic and Reconstructive Surgery, Oct. 2004, pp. 1097-1098.
Defranzo, A.J., et al., "109: Use of Sub-Atmospheric Pressure for Treatment of Gunshot Injuries", Plastic Surgical Forum, V. XXIII, Los Angeles, CA, Oct. 14-18, 2000, pp. 180-181.
Marks, M., et al., "Management of Complex Soft Tissue Defects in Pediatric Patients Using the V.A.C. Wound Closure", Plastic Surgical Forum, V. XXI, Boston, MA, Oct. 3-7, 1998, pp. 215-216.
Morykwas, M. and Argenta, L., "Use of Negative Pressure to Prevent Progression of Partial Thickness Burns", American Burn Association, V. 26, $26^{th}$ Annual Meeting, Apr. 20-23, 1994, Orlando, Florida, pp. 157.
Morykwas, M. and Argenta, L., "Vacuum Assisted Closure (VAC Therapy) for Secondary Closure of Dehisced and Infected Wounds", Wound Repair and Regeneration, Jul.-Sep. 1995, pp. 361.
Morykwas, M. and Argenta, L., "Treatment of Burned Extremities Using Vacuum Therapy (The V.A.C.)", Wound Repair and Regeneration, V. 3, N. 3, Jul.-Sep. 1995, pp. 367.
Webb, L. and Morykwas, M., et al., "The Use of Vacuum-Assisted Closure in Composite Wound Management", The Third Riva Congress, Current Perspectives in Fracture Management and Orthopaedic Reconstruction, May 10-14, 2000, Italy, pp. 137.
Morykwas, M. and Webb, L., "Sub-Atmospheric Pressure for the Treatment of Lower Extremity Wounds", The Third Riva Congress, Current Perspectives in Fracture Management and Orthopaedic Reconstruction, May 10-14, 2000, Italy, pp. 135-136.
Argenta, L., et al., "Use of V.A.C. for Treatment of Dehisced Sternal Incisions", Plastic Surgical Forum, V. XXIII, Los Angeles, CA, Oct. 14-18, 2000, pp. 172-174.
Morykwas, M., et al., "Isolated Muscle Flap Survival with Complete Venous Occlusion: Varying Delay in External Application of Sub-atmospheric Pressure", Plastic Surgical Forum, V. XXI, Boston, MA, Oct. 3-7, 1998, pp. 237.
Morykwas, M. and Argenta, L., "V.A.C. Experience and Difficult Wounds", des Journees Regionales des Plaies et Cicatrisations, Sep. 22-23, 1997, pp. 76-90.
Morykwas, M. and Argenta, L., "Use of the V.A.C.™ for Treatment of a Traumatic Left Hip Disarticulation",ACA-Acta Chir. Austriaca, Supplement Nr. 150, 1998, pp. 24-25 and cover sheet.
Banwell, P., et al., "Application of Topical Sub-Atmospheric Pressure Modulates Inflammatory Cell Extravasation in Experimental Partial Thickness Burns", Wound Repair and Regeneration, Jul./Aug. 1999, V. 7, N. 4, pp. A286-A287.
Banwell, P., et al., "Dermal Perfusion in Experimental Partial Thickness Burns: The Effect of Topical Subatmospheric Pressure", Jan./Feb. 2000, V. 21, N. 1, Part 2, Burn Care & Rehabilitation.
Morykwas, M., et al., "The Effect of Externally Applied Subatmospheric Pressure on Serum Myoglobin Levels After a Prolonged Crused/Ischemia Injury", The Journal of TRAUMA Injury, Infection and Critical Care, Sep. 2002, V. 53, N.3, pp. 537-540.
Molnar, J., et al., "Acceleration of Integra Incorporation in Complex Tissue Defects with Subatmospheric Pressure", Plastic and Reconstructive Surgery, Apr. 15, 2004, pp. 1339-1346.
Defranzo, A.J., et al., "The Use of Vacuum-Assisted Closure Therapy for the Treatment of Lower-Extremity Wounds with Exposed Bone", Plastic and Reconstructive Surgery, Oct. 2001, V. 108, N. 5, pp. 1184-1191.
Morykwas, M., "The Use of the V.A.C. Wound Treatment System for Acute and Subacute Wounds", Plaies & Cicatrices, Would Closure Healing, Apr. 21, 22 and 23, 1999.

(56) References Cited

OTHER PUBLICATIONS

Webb, L., et al., "Negative Pressure Wound Therapy in the Management of Orthopedic Wounds", Ostomy Wound Management, Apr. 2004, V. 50, Issue 4A (Suppl), pp. 26-27 and cover sheet.
Webb, L., et al., "Wound Management With Vacuum Therapy", English abstract from website printout and German article, http://www.ncbi.nlm.nih.gov/entrez/query.fcgi?cmd=Retrieve & db=pubmed&dot=Abstra . . . , Dec. 2, 2004, 2 pages website printout, German article, Oct. 2001, pp. 918-926.
Webb, "New Techniques in Wound Management: Vacuum-Assisted Wound Closure", Journal of the American Academy of Orthopaedic Surgeons, V. 10, N. 5, Sep./Oct. 2002, pp. 303-311.
Morykwas, M. and Argenta, L., "Sub-Atmospheric Pressure Wound Treatment and Cultured Keratinocyte Allografts", Cultured Human Keratinocytes and Tissue Engineered Skin Substitutes, © 2001 Georg Thieme Verlag, pp. 343-346.
Molnar, J., et al., "Single-Stage Approach to Skin Grafting the Exposed Skull", Plastic and Reconstructive Surgery, Jan. 2000, V. 105, N. 1, 174-177.
Scherer, L, et al., "The Vacuum Assisted Closure Device: A Method of Securing Skin Grafts and Improving Graft Surival", Arch. Surg., V. 137, Aug. 2002, pp. 930-934.
Miller, P., et al., "Late Fascial Closure in Lieu of Ventral Hernia: The Next Step in Open Abdomen Management", the Journal of TRAUMA Injury, Infection and Critical Care, Nov. 2002, V. 53, N. 5, pp. 843-849.
Betancourt, S., "A Method of Collecting the Effluent From Complicated Fistula of the Small Intestine", 1986, p. 375.
Dorland's Illustrated Medical Dictionary, Twenty-Fifth Edition, 1974, pp. 1112.
Hopf, H., et al., "Adjuncts to preparing wounds for closure Hyperbaric oxygen, growth factors, skin substitutes, negative pressure wound therapy (vacuum-assisted closure)", Foot Ankle Clin N Am 6, 2001, pp. 661-682.
Chariker-Jeter® Wound Drainage Kit, BlueSky Medical, 2 page advertisement with business card from Quality Medical Supply.
Chariker-Jeter® Wound Drainage Kit Instructions, Item #500.7777, BlueSky Medical, 2 pages.
Wooding-Scott® Wound Drainage Kit Contents, Item #500.8888, 1 page.
Montgomery, B., "Easy Dressing of Large, Draining Abdominal Wounds Using Moisture Vapor-Permeable Film", pp. 417-418, Techniques for Surgeons, Wiley Medical Publication, © 1985.
Herrmann, L., et al., "The Pavaex (Passive Vascular Exercise) Treatment of Obliterative Arterial Diseases of the Extremeties", The Journal of Medicine, Dec. 1933, pp. 524-529.
Herrmann, L., et al., "Passive Vascular Exercises: Treatment of Peripheral Obliterative Arterial Diseases by Rhythmic Alternation of Environmental Pressure", Archives of Surgery, v. 29, n. 5, Nov. 1934, pp. 697-704.
Sturr, R., Evaluation of Treatment of Peripheral Vascular Disease by Alternating Positive and Negative Pressure, Philadelphia, Archives of Physical Therapy, Sep. 1938, pp. 539-543.
Balin, A., et al., "Oxygen Modulates Growth of Human Cells at Physiologic Partial Pressures", Laboratory for Investigative Dermatology, J. Exp. Med. ©, the Rockefeller University Press, v. 160, Jul. 1984, pp. 152-166.
Saran Resins and Films, "Fresh Thinking". website printout, 6 pages, Jan. 20, 2004.
Bluesky Medical, "A Leader in Suction Technology—Wound Drainage Experts", printout of website, 55 pages, Apr. 8, 2003, www.blueskymedical.com.
Davydov, et al., "Would Healing Under the Conditions of Vacuum Draining", Khirurgiia (Mosk). 1992, (7-8): 21-6 (with English translation by Scientific Translation Services).
Coyle, M., et al., "A Case Study: Positive Outcomes to Negative Pressure Wound Therapy—A collaborative assessment", Hospital of Saint Raphael, 1 page chart.

Nemoto, H., et al., "Stories From the Bedside: Purple Urine Bage Syndrome Development in Ileal Conduit", WCET, Journal 23(2), pp. 31-34.
Baker, B., "Negative-Pressure Therapy Looks Promising", Skin & Allergy News, Feb. 2000, p. 14.
McCallon, S., et al., "Vacuum-Assisted Closure versus Saline-Moistened Gauze in the Healing of Postoperative Diabetic Foot Wounds", Ostomy Wound Management, Aug. 2000, v.46, Issue 8.pp. 28-29, 31-32, 34.
M. Gosta Arturson, *The Pathophysiology of Severe Thermal Injury*, JBCR, 6(2):129-146 Mar.-Apr. 1985.
R. A.F. Clark et al., The Molecular and Cellular Biology of Wound Repair, Chapter 1 (1988).
Jeter, K.F. et al. (eds.), "Managing Draining Wounds and Fistulae: New and Established Methods," Chronic Wound Care: Health Management Publications, 1990, pp. 240-246.
Aeros, "Moblvac II."
Aeros, Aeros Instruments, Inc. 1111 Lakeside Drive, Gurnee, IL 60031. Aug. 1993. "Care-E-Vac."
Emerson, Series 55. J. H. Emerson Co., 22 Cottage Park Ave., Cambridge, MA 02140. "Emerson Post-Operative Suction Pumps."
Emerson, J. H. Emerson Co., (address: same as above). "Emerson Transport Suction Unit."
Aeros, Aeros Instruments, Inc. 3411 Commercial Ave., Northbrook, IL 60062. Oct. 1988. Part No. 1504-02 7M. "Instavac Aspirator."
"Pleur-evac. Adult-Pediatric, Non-Metered." Code No. A-4000. Control No. F7961J.
Instruction Manual, Creative Medical Laboratories, Inc. P.O. Box 6347, Rochester, Minn. 55903. "TUGS" (Transportable Universal Gradient Suction).
Deknatel, Div. of Howmedica, Inc. Quenns Village, NY 11429. "Pleur-evac."
Sparta Instrument Corp. 26602 Corporate Ave., Hayward, CA 94545. "Power Source Multi-Purpose Surgical Aspirator."
Wells Johnson Company, 2045 N. Forbes Blvd., Suite 106, Tucson, AZ. "Point 5 Aspirator."
Microtek Heritage, Inc. P.O. Box 2487, Columbus, MS 39704. "Wound-Evac ET."
Fleischmann, W. *Wund Forum Spezial*. IHW '94. "Vakuumversiegelung zur Behandlung von Probelmwunden" (with English translation: "Vacuum sealing for Treatment of Problematical Wounds."
Fleischmann, W. *Acta Orthopaedica Belgica*. vol. 58, Suppl. I-1992 "Treatment of Bone and Soft Tissue Defects in Infected Nonunion."
Fleischmann, W. Strecker W, Bombelli M, Kinzl L. *Unfall Chirurg*. Springer-Variag 1993. 96:488-92 "Vakuumversiegelung zur Behandlung des Weightteilschadens bei offenen Frakturen." with English translation [Vacuum sealing as treatment of soft tissue damage in open fractures]. [German].
Valenta, A.L. *American Journal of Nursing*. Apr. 1994. "Using the Vacuum Dressing Alternative for Difficult Wounds." 94:44-5.
Bier, A., "Hyperemia by Suction Apparatus" Chapter VIII, Hyperemia as a Therapeutic Agent, Chicago, IL, Roberts Publishing, 74-85, (1905).
Saunders, J. W., The Lancet, pp. 1286-1287, Jun. 28, 1952, "Negative-Pressure Device for Controlled Hypotension during Surgical Operations".
Landis, et al., Robinette Foundation of the Hospital of the University of Pennsylvania, "The Effects of Alternate Suction and Pressure on Blood Flow to the Lower Extremities" (Sep. 1933).
Hargens et al., Space Physiology Laboratory, Life Science Division, NASA Ames Research Center, "Control of Circulatory Function in Altered Gravitational Fields" (Feb. 1992).
Wolthuis et al, Physiological Reviews, 54: 566-595, Jul. 1974, "Physiological Effects of Locally Applied Reduced Pressure in Man".
Viljanto et al., Br. J. Surg., 63: 427-430, 1976, "Local Hyperalimentation of Open Wounds".
Dillon, R. Angiology—The Journal of Vascular Diseases, pp. 47-56, Jan. 1986, "Treatment of Resistant Venous Stasis Ulcers and Dermatitis with the End-Diastolic Pneumatic Compression Boot".

(56) References Cited

OTHER PUBLICATIONS

Lundvall et al., Acta Physiol Scand, 136: 403-309, accepted Jan. 28, 1989, "Transmission of externally applied negative pressure to the underlying tissue. A study on the upper arm of man".
Klemp et al., The Journal of Investigative Dermatology, pp. 725-726 (1989), "Subcutaneous Blood Flow in Early Male Pattern Baldness".
A. Harle, Z. Orthop., 127: 513-517 (1989), "Schwachstellen herkommlicher Drainagen" with English Translation.
Dunlop et al., Br. J. Surg., 77: 562-563 (1990), "Vacuum drainage of groin wounds after vascular surgery: a controlled trail".
Maddin et al., International Journal of Dermatology, 29: 446-450 (1990), "The Biological Effects of a Pulsed Electrostatic Field with Specific Reference to Hair: Electrotrichogenesis".
Nakayama et al., Ann. Plast. Surg., 26:499-502 (1991), "A New Dressing Method for Free Skin Grafting in Hands".
Hargens et al., Aviation, Space and Environmental Medicine, pp. 934-937, Oct. 1991, "Lower Body Negative Pressure to Provide Load Bearing in Space".
Author unknown, Science, Sep. 1992, p. 42, "The Not-So-Bald-Truth".
Techno Takatsuki Co., Ltd., 8-16 Hatchonishimachi, Takatsuki City, Osaka, Japan, "HiBlow Air Pump".
Wells Johnson Company, 2045 N. Forbe Blvd., Suite 106, Tucson, AZ, "Suction Tips".
Industrial Equipment News, P.O. Box 1158, Skokie, IL 60076-9786, "Miscellaneous Equipment".
Letsou et al. "Stimulation of Adenylate Cyclase Activity in Cultured Endothelial Cells Subjected to Cyclic Stretch." Cardiovascular Surgery 3. Toronto. Sep. 1989. 634-639.
Bucalo et al. "Inhibition of Cell Proliferation by Chronic wound Fluid." Wound Repair and Regeneration. 181-186 Jul. 1993,
Falanga, Vincent. "Growth Factors and Chronic Wounds: The need to Understand the Microenvironment." Journal of Dermatology, Bol. 19: 667-672. 1992.
Urschel et al. "The Effect of Mechanical Stress on Soft and Hard Tissue Repair; a Review." British Journal of Plastic Surgery. 41, 182-186. 1988.
Gogia, Prem P. "The Biology of Wound Healing." Ostomy/Wound Management. Nov.-Dec. 1992. pp. 12, 14-16, 18-20, 22.
Wysocki et al. "Wound Fluid from Chronic Leg Ulcers Contains Elevated Levels of Metalloproteinases MMP-2 and MMP-9." The Society for Investigative Dermatology, Inc. Jul. 1993. 64-68.
Olenius et al. "Mitotic Activity in Expanded Human Skin." Plastic and Reconstructive Surgery. Feb. 1993. 213-216.
Mulder, G. D. et al. (eds.), Clinicians' Pocket Guide to Chronic Wound Repair, (Spartanburg, SC: Wound Healing Publications), 1991, pp. 54-55.
Chariker, M. E. et al. (eds), "Effective Management of Incisional and Cutaneous Fistulae with Closed Suction Wound Drainage," Contemporary Surgery, vol. 34, Jun. 1989, pp. 59-63.
Rastgeldi, S.: I. Pressure Treatment of Peripheral Vascular Diseases. II. Intermittent Pressure Treatment of Peripheral Vascular Diseases. Opuscula Medica, Suppl. XXVII, 1972.
OP—Journal Nr. 3, Jahr. 6, Dec. 1990, pp. 31-35 W. Fleischmann, M. Mentzel, L. Kinzl "BWS, Gefahren und Komplikationen der Therapie" with English Trans.
Zumtobel et al., (1991) "Wunddrainage in der Elektiveund Notfallchirurgie" Wolfgang Pabst Verlag, relevant p. 12, left column. English Translation attached.
Saechtling, Kunststoff-Taschenbuch, 24. Ausgabe 1989, S. 439, 477. English Translation attached.
Mutschler, W. Bakker D. J., "Temporarer Hautersatz", ZFA 1989, Heft 24, S. 714-720 als Sonderdruck. English Translation attached.
W. Fleischmann, U. Becker, M. Bischoff, H. Hoekstra, "Vacuum sealing: indication, technique, and results", Eur. J. Orthop & Traumato (1995) 5:37-40.
Argenta LC, Morykwas MJ. Vacuum-assisted closure: a new method for wound control and treatment: clinical experience. Ann Plast Surg 1997;38: 563-577.

Morykwas MJ, Argenta LC, Shelton-Brown EI, McGuirt W. Vacuum-assisted closure: a new method for wound control and treatment: animal studies and basic foundation. Ann Plast Surg 1997; 38:553-62.
Davydov IA, Larichev AB, Smirnov AP, Flegontov VB. Vakuumterapiia v lechenii ostrykh gnoinykh zabolevanii miagkikh tkanei I gnoinykh ran. [Vacuum therapy of acute suppurative diseases of soft tissues and suppurative wounds]. Russian Vestnik Khirurgii Imeni I—I—Grekova 1988; 141: 43-6 with Eng.Trans.
Davydov IA, Abramov AI, Larichev AB. Vakuum-terapiia v preduprezhdenii posleoperatsionnoi ranevoi infektsii. [Vacuum therapy in the prevention of postoperative wound infection]. Russian Vestnik Khirurgii Imen I—I—Grekova 1991; 147:91-5, with English Translation.
Iankov NI. Simuliatsiia konsolidatsii perelomov nizhnei cheliusti vaktuumnoi terapiei. [Stimulation of consolidation of mandibular fractures by means of vacuum therapy] Russian. Stomatologiia 1971; 50: 86, with Eng. Trans.
Inoiatov IM, Aleksandrov VB. Lechenie promezhnostnoi rany posle amputatsii priamoi kishki vakuum-aspiratsiei. [Vacuum aspiration in the treatment of the perineal wound following extirpation of the rectum]. Russian. Khirurgiia 1971; 47:74-8, with English Translation.
Kochnev VA. Primenenie vakuum-drenazhnoi sistemy dlia profilaktiki posleoperatsionnykh ranevykh oslozhnenii u bol'nykh opukholiami. [The use of a vacuum drainage system in the prevention of postoperative wound complications in tumor patients]. Russian. Voprosy Onkologii 1967; 13:102-5, w/Eng. Trans.
Mirazimov BM. Svobodnaia Kozhnaie plastika stopy s podgotovkoi ranevoi poverkhnosti vakumiravaniem [Free skin graft of the foot with vacuum preparation of the wound surface]. Russian. Orthopediia Travmatologiia I Protezirovanie 1966;27:19-22, with English Translation.
Mirazimov BM, Vasina Ta, Mezhericher MI. Mikroflora dlitel'no nekazhivaiushchikh ran i effektivnost' metoda vakuumirovaniia. [Microflora of prolonged non-healing wounds and the effectiveness of the vacuum evaporative method]. Russian. Khirurgiia 1967; 43: 40-3, with English Translation.
Mirazimov BM. Vorbereitung von Wunden und Geschwuren zur Hautplastik unter Anwendung der Vakuumierung [Preparation of wounds and abcesses for dermatoplasty by means of a vacuum device]. German. Beitrage zur Orthopadie und Traumatologie 1967; 14:224-30, with Eng. Translation.
Netudykhatka O. Vliianie nizkogo dozirovannogo vakuuma na techenie reparativnogo protsessa v kostnoi tkani [Effect of low vacuum on the course of the reparative process in bone tissue]. Russian. Voprosy Kurortologii, Fizioterapii i Lechebnoi Fizicheskoi Kultury 1972; 37:411-5, w/Eng. Trans.
Volkov LA. Isporzovanie vakuum-drenazhnoi sistemy v khirurgicheskoi praktike. [Use of vacuum-drainage system in surgical practice]. Russian. Klinicheskaia Khirurgiia. 1973;7:54-5, with English Translation.
Teder H, Sanden G, Svedman P. Continuous Wound Irrigation in the Pig. J Invest Surg 1990;3:399-407.
Nakayama Y, Tomotari I, Soeda S. A New Method for the Dressing of Free Skin Grafts. Plast Reconstr Surg 1990;86:1216-1219.
Brock WB, Barker DE, Burns RP. Temporary Closure of open abdominal wounds: the vacuum pack. Amer Surg 1995;61:30-5.
Shein M, Saadia R, Jameson JR, Decker GAG. The "sandwich technique" in the Management of the Open Abdomen. Br J Surg 1986;73:369-70.
Broome A. Hansson L, Lundgren F, Smedberg S. Open Treatment of Abdominal Septic Catastrophies. World J. Surg 1983;7:792-6.
Vatanasapt V, Areemit S, Jeeravipoolvarn P, et al. Red rubber bulb, cheap and effective vacuum drainage. Journal of the Medical Association of Thailand 1989;72:193-7,
Brummelkamp WH, Taat CW, Slors JF. High-vacuum drainage and primary perineal wound closure in abdominoperineal excision of the rectum. Netherlands Journal of Surgery 1991;43:236-9.
Morykwas J, Argenta LC. Nonsurgical modalities to enhance healing and care of soft tissue wounds. Journal of the Southern Orthopaedic Association 1997;6:279-88.

(56) References Cited

OTHER PUBLICATIONS

Sames CP. Sealing of wounds with vacuum drainage [letter] Br Med J 1977;2:1123.
Greer SE, Longaker MT, Margiotta M. Preliminary Results from a Multicenter, Randomized, Controlled, Study of the Use of Subatmospheric Pressure Dressing for Pressure Ulcer Healing. Wound Repair and Regeneration 1999;7:255.
Greer SE, Longaker MT, Margiotta M, Matthews AJ, Kasabian A. The Use of Subatmospheric Pressure Dressing for the Coverage of Radial Forearm Free Flap Donor-Site Exposed Tendon Complications. Ann Plast Surg 1999;43:551-554.
Greer SE, Duthie E, Cartolano B, Koehler KM, Maydick-Youngberg D, Longaker MT. Techniques for Applying Subatmospheric Pressure Dressing to Wounds in Difficult Regions of Anatomy. JWOCN 1999;26:250-3.
Greer SE, Kasabian A, Thorne C, Borud L, Sims CD, Hsu M. The Use of Subatmospheric Pressure Dressing to Salvage a Gustilo Grade IIIB Open Tibia Fracture with Concomitant Osteomyelitis and Avert a Free Flap. Ann Plast Surg 1998;41:687.
Genecov DG, Schneider AM, Morykwas MJ, et al. A Controlled subatmospheric pressure dressing increases the rate of skin graft donor site reepithelialization. Ann Plast Surg 1998;40:219-25.
Mendez-Eastman S. Negative pressure wound therapy. Plastic Surgical Nursing 1998;18:27-9, 33-37.
Banwell P. Withey S, Holten I. The use of negative pressure to promote healing [letter; comment]. Brit J Plast Surg 1998;51:79.
Blackburn J H Boemi L, Hall WW. et al. Negative-pressure dressings as a bolster for skin grafts. Ann Plast Surg 1998;40:453-7.
Smith LA, Barker DE, Chase CW, et al. Vacuum Pack Technique of Temporary Abdominal Closure: A Four-Year Experience. Amer Surg 1997;63:1102-8.
McCulloch JM, Kemper CC. Vacuum-Compression Therapy for the Treatment of an Ischemic Ulcer. Physical Therapy 1993;73:165-9.
Mullner T, Mrkonjic L, Kwasny O, Vecsei V. The use of negative pressure to promote the healing of tissue defects: a clinical trial using the vacuum sealing technique [see comments]. Brit J Plast Surg 1997;50:194-9.
Mirazimov, B.M.: Free Skin Grafting of Wounds and Ulcers using the "Vacuum Treatment" Method. [Orthop. Travmatol. Protez., 28(1):54-58.] with English Trans. 1967.
Greer, Steven E., "Whither Subatmospheric Pressure Dressing?" The Institute of Reconstructive Plastic Surgery, The New York University Medical Center, New York, NY April Issue of Annals of Plastic Surgery 2000.
Registration No. 1982349. Owner, KCI Inc., 3440 E. Houston Street San Antonio Texas 78219. Source: United States Patent and Trademark Office official website. Filing date May 1, 1995 Registration Date Jun. 25, 1996.
Hidden Interest—A Special Report.; When Physicians Double as Entrepreneurs. The New York Times. 11pp. Nov. 30, 1999.
Defranzo, Anthony J., et al., "Vacuum-Assisted Closure for the Treatment of Degloving Injuries." Plastic and Reconstructive Surgery 104 (7) 2145-48: (1999).
Morykwas, Michael J., et al., "Use of Subatmospheric Pressure to Prevent Progression of Partial-Thickness Burns in a Swine Model". Journal of Burn Care & Rehabilitation 20 (1 Part 1): 15-21 (1999).
Morykwas, Michael J., et al., "Use of Subatmospheric Pressure to Prevent Doxorubicin Extravasation Ulcers in a Swine Model". Journal of Surgical Oncology 72:14-17 (1999).
Schneider, Andrew M., et al., "A New and Reliable Method of Securing Skin Grafts to the Difficult Recipient Bed". Plastic and Reconstructive Surgery 102(4) 1195-98 (1998).
Rosser, Charles J., et al., "A New Technique to Manage Perineal Wounds". Infections in Urology 13(2) 45-47, 56 (2000).
Philbeck, Thomas E., et al., "The Clinical and Cost Effectiveness of Externally Applied Negative Pressure Wound Therapy in the Treatment of Wounds in Home Healthcare Medicare Patients". Ostomy/Wound Management 45(11) 41-44, 46-50 (1999).
Meara, John G., et al., "Vacuum-Assisted Closure in the Treatment of Degloving Injuries". Annals of Plastic Surgery 42(6) 589-594 (1999).
Obdeijn, Miryam C., et al., "Vacuum-Assisted Closure in the Treatment of Poststernotomy Mediastinitis". Ann Thorac Surgery 68 2358-60 (1999).
Mendez-Eastman, Susan., "When wounds won't heal". RN 20-24 (1998).
Hartnett, Jacqueline M., "Use of Vacuum-Assisted Wound Closure in Three Chronic Wounds". JWOCN 25 (6) 281-290 (1998).
Mendez-Eastman, Susan., "Use of Hyperbaric Oxygen and Negative Pressure Therapy in the Multidisciplinary Care of a Patient with Nonhealing Wounds". JWOCN 26(2) 67-76 (1999).
Wooding-Scott, Margaret et al., "No-Wound is Too Big for Resourceful Nurses". RN, Dec. 1988, 22-25.
Davydov, et al., "Pathenogenic mechanism of the effect of vacuum therapy on the course of the wound process". Khirurgiia, Jun. 1990 (with English translation).
Davydov, et al., "Vacuum therapy in the treatment of suppurative lactation mastitis". Vestn. Khir., Nov. 1986 (with English translation).
Davydov, et al., "Bacteriological and cytological evaluation of the vacuum therapy of suppurative wounds". Vestn. Khir., Oct. 1988 (with English translation).
Davydov, et al., "Basis of the use of forced early secondary suture in the treatment of suppurative wounds by the vacuum therapy method". Vestn. Khir., Mar. 1990 (with English translation).
Borzov, et al., "Vacuum therapy of some skin diseases". Vestn. Dermatol. Venerol., Aug. 1965 (with English translation).
M.J. Morykwas and L.C. Argenta, "Techniques in Use of V.A.C. Treatment (in English)", Acta Chir. Austriaca Supplement Nr. 150, 1998, p. 3-4 of 2-28.
Garcia-Rinaldi, et al., "Improving the Efficiency of Wound Drainage Catheters", J. Surg., 1975, pp. 372-373.
Raffl, et al. "The Five Year Survival Rate for Gastric Cancer: Statistical Study from Syracuse Medical Center", Cancer, 6:756-759, Jul. 1953.
Raffl, et al., The Use of Negative Pressure Under Skin Flaps After Radical Mastectomy, Ann. Surg. 136: 1048, Dec. 1952.
Marie Knight, "A Second Skin for Patients with Large Drainage Wounds," Nursing 6(1) p. 37, 1976.
Oscar Ramirez, "Optimal Wound Healing under Op-Site Dressing" Plas. & Recon. Surg., 73(3): 474-475; 1984.
Helen Bibleheiner, "Dealing with a Wound that Drains 1.5 Liters per Day," RN Aug. 1986.
Peter Schwab, "Primary Closure of the Perineal Wound After Proctectomy" Mayo Clin. Proc., Mar. 1974, vol. 49.
3M™, Tegaderm Family of Transparent Dressings for Chronic Wounds, pp. 1-8 (2002).
Alper, Joseph C., et al., "The In Vitro Response of Fibroblasts to the Fluid that Accumulates Under a Vapor-Permeable Membrane". Journal of Investigative Dermatology, 84:513-515, 1985.
Alper, Joseph C., et al., "Use of the Vapor Permeable Membrane for Cutaneous Ulcers: Details of application and side effects", Journal of the American Academy of Dermatology, vol. 11, No. 5, Part I, Nov. 1984, pp. 858-866.
Angermeier, Marla C., et al., "Vapor-Permeable Membrane Therapy for Ulcers of Osteomyelitis", J. Dermatol. Surg. Oncol 10:5, May 1984, pp. 384-388.
Bourke, et al., "Comparison Between Suction and Corrugated Drainage After Simple Mastectomy: A Report on Controlled Trial", Br. J. Surg., vol. 63, 1976, pp. 67-69.
ConstaVac™ Closed Wound Drainage System, Stryker Instruments, 2 pages.
Eaglstein, William H., "Experiences with Biosynthetic Dressings", Journal of the American Academy of Dermatology, vol. 12, No. 2, Part 2, Feb. 1985, pp. 434-440.
Falanga, Vincent, et al., "A Therapeutic Approach to Venous Ulcers", Journal of the American Academy of Dermatology, vol. 14, No. 5, Part 1, May 1986, pp. 777-784.
Friedman, S., et al., "Treatment of Dermabrasion Wounds with a Hydrocolloid Occlusive Dressing", Arch Dermatol, vol. 121, Dec. 1985, pp. 1486-1487.
Friedman, Stephen J., et al., "Management of Leg Ulcers with Hydrocolloid Occlusive Dressing", Arch. Dermatol., vol. 120, Oct. 1984, pp. 1329-1336.

(56) References Cited

OTHER PUBLICATIONS

Holland, K.T., et al., "A Comparison of the In Vivo Antibacterial Effects of OpSite, Tegaderm and Ensure dressings", Journal of Hospital Infection, 1985, 6, pp. 299-303.
Jeter, Katherine F., et al., "Wound Dressings of the Nineties: Indications and Contraindications", Clinics in Podiatric Medicine and Surgery, vol. 8, No. 4, Oct. 1991, pp. 799-816.
Katz, Stuart, et al., "Semipermeable Occlusive Dressings", Arch Dermatol., vol. 122, Jan. 1986, pp. 58-62.
Lewis, R.T., "Knitted Polypropylene (Marlex) Mesh in the Repair of Incisional Hernias", The Canadian Journal of Surgery, vol. 27, No. 2, Mar. 1984, pp. 155-157.
Lower Extremity Ulcers, Chapter 9, pp. 47-57.
Microtek Medica, Inc. "The Microtek Complete Closed Wound Drainage System", 6 pages.
Rovee, David T., et al., "Effect of Local Wound Environment on Epidermal Healing", Dept. of Skin Biology, Johnson & Johnson Research, New Brunswick, NJ, pp. 159-181 (1972).
Satas, Donatas, "Handbook of Pressure-Sensitive Adhesive Technology", Silicone Release Coatings, Van Nostand Reinhold Company, 1982, pp. 384-403.
Turner, T.D., "A Look at Wound Dressings", Health and Social Service Journal, May 4, 1979, pp. 529-531.
Turner, T.D., "Recent Advances in Wound Management Products", pp. 3-6.
Turner, T.D., "Semipermeable Films as Wound Dressings", Welsh School of Pharmacy, University of Wales, Great Britain (Jul. 31, 1984).
Turner, T.D., "The Development of Wound Management Products", Chronic Wound Care, pp. 31-46.
Turner, T.D., et al., "Wound Management Product Selection", Journal of Sterile Services Management, Apr. 1985, pp. 3-6.
Varghese, Mathew C., et al., "Local Environment of Chronic Wounds Under Synthetic Dressings", Arch. Dermatol, vol. 122, Jan. 1986, pp. 52-57.
Viljanto, J., "Cellstic: A Device for Wound Healing Studies in Man. Description of the Method", Journal of Surgical Research, 20, 1976, pp. 115-119.
Wagner, S.A., et al., "An individualized Plastic Intraoral Device for the Collection of Human Parotid Saliva", International Journal of Clinical Pharmacology, Therapy and Toxilogy, Vo. 22, No. 5, 1984, pp. 236-239.
Wilson, John L., et al., "Loss of Blood Volume in Spinal Surgery with Use of Closed Wound Suction: An Experimental Study", Southern Medical Journal, Jul. 1968, pp. 761-763, read before the Section on Orthopaedic and Traumatic Surgery, Southern Medical Association, 61st Annual Meeting, Miami Beach, FL, (Nov. 13-16, 1967).
Winter, G.D., "Healing of Skin Wounds and the Influence of Dressings on the Repair Process", pp. 46-60 of "Surgical dressings and wound healing: proceedings of a symposium held on Jul. 7-8, 1970 at the University of Bradford," Crosby Lockwood for Bradford University Press, (1971).
Ji, Y., et al., "Electrospun three-dimensional hyaluronic acid nanofibrous scaffolds," Biomaterials 27:3782-3792 (2006; available online Mar. 23, 2006).
Fujihara, K., et al., "Guided bone regeneration membrane made of polycaprolactonelcalcium carbonate composite nano-fibers," Biomaterials 26:4139-4147 (2005; available online Dec. 24, 2004).
Sethuraman, S., et al., "Novel low temperature setting nanocrystalline calcium phosphate cements for bone repair: Osteoblast cellular response and gene expression studies," J. Biomed. Mater. Res. A 82:884-891 (2007; published online Mar. 2, 2007).
Deng, M., et al., "Miscibility and in vitro osteocompatibility of biodegradable blends of poly[(ethyl alanato) (p-phenyl phenoxy) phosphazene] and poly(lacitic acid-glycolic acid)," Biomaterials 29:337-349 (2008; available online Oct. 17, 2007).
Lu, XL., et al., "Shape memory property of poly(L-lactide-co-ε-caprolactone) copolymers," Materials Science and Engineering A 438-440:857-861 (2006).

Leonelli, C., et al., "Synthesis and characterization of cerium-doped glasses and in vitro evaluation of bioactivity," Journal of Non-Crystalline Solids 316:198-216 (2003).
PCT/US08/30581—International Report on Patentability (Jul. 22, 2010).
Svedman, P., "A dressing allowing continuous treatment of a biosurface,"IRCS Medical Science: Biomedical Technology; Clinical Medicine; Surgery and Transplantation, 7:221 (1979), with annotations.
Viljanto, J., "A new method for treatment of open wounds", Ann. Chir. Gynaecol. Fenn., (English abstract on first page, and 1 sheet printout from PubMed); 60:94-100 (1972).
Yusupov, Y.N., et al., "Active drainage of wounds", Vestn. Khir. Im. I.I. Grek., (with English abstract on last page, 5 sheets of English translation, 3 pp. of English translation by BlueSky publishing and 1 sheet printout from PubMed); 138(4):42-46 (Apr. 1987).
Ulaschik, V.S., "Barotherapy", in Physical Therapy, Universal Medical Encyclopedia; pp. 85-86 and cover sheet (3 sheets in English, 3 sheets in Russian), (2008, allegedly gone to print Oct. 1, 2007).
Molnar, J.A., "V.A.C. and burn care", presentation slides.
Slides regarding use of V.A.C.
Photographs showing patient treatment, "sheet 2", (Jeter deposition Exhibit 741) (allegedly dated 1985).
Demorest, R.L., "New standards in water vapour permeability testing," British Plastics & Rubber, 3 sheets, (handwritten label on first sheet shows "Exhibit TT"), (May 1995).
Kirk-Othmer, Encyclopedia of Chemical Technology, 2nd completely revised edition, vol. 9, pp. 220-232, John Wiley & Sons, Inc., (1966).
Stedman's Medical Dictionary, 25th ed., pp. 1739, Williams & Wilkins, (1990).
Standard Operating Procedure, The determination of moisture vapour permeability (MVP) and water transmission rate (WTR), implementation date: Sep. 11, 2006 and QA Operational Laboratories Analytical Report dated Nov. 13, 2008.
British Pharmacopoeia Selections: (1988) vol. II, p. 1126-1127, A223-A224; Addendum 1992, p. 1494; (1993) vol. II, p. 1266, A218-A219.
Solovev, V.A., "Treatment and prevention of suture failures after gastric resection," Dissertation abstract, with alleged index card, S.M. Kirov Gorky State Medical Institute, Gorky, U.S.S.R., (Exhibit I of Third party comments) (1988).
Solovev, V.A., "The method of treatment of immature external fistulas in the upper gastrointestinal tract," S.M. Kirov Gorky State Medical Institute, Gorky, U.S.S.R., (Exhibit J of Third party comments) (1987).
Thomas, S., "Wound Management and Dressings," The Pharmaceutical Press, London, 223 sheets, (1990).
Wood, R.A.B., et al., "A new method for treatment of open granulating wounds," Surgical Dressings in the Hospital Environment, T.D. Turner, ed., et al., Surgical Dressings Research Unit, Welsh School of Pharmacy, Uwist, Cardiff, 8 sheets, (1975).
Turner, T.D., ed., et al., Advances in Wound Management, including "The role of foam dressings in wound management" by S. Thomas, "Clinical aspects of Synthaderm®" by T. Martin, et al., "Lyofoam®—Used in the treatment of leg ulcers" by J. Creevy, and "Clinical experience of Silastic® foam dressing," by K.G. Harding; John Wiley & Sons, 17 sheets, (Proceedings dated Mar. 20-21, 1985) (1986).
Bagautdinov, N.A., "Variant of external vacuum aspiration in the treatment of purulent diseases of soft tissues," Current Problems in Modern Clinical Surgery, Interdepartmental Collection, Cheboksary, pp. 94-96, and library card, in English and Russian, (KCI_Con00220647-59) (1986).
Kuznetsov, V.A., et al., "Vacuum and vacuum-sorption treatment of open purulent wounds," II All-Union Conference "Wounds and Wound Infections" Moscow, pp. 91-92, with library card and table of contents, in English and Russian, (KCI_Con00220660-89) (1986).
Williams, R.S., "A simple technique for successful primary closure after excision of pilonidal sinus disease," Ann. R. Coll. Surg. England, 72:313-315, (only 2 sheets provided), (1990).

(56) References Cited

OTHER PUBLICATIONS

Gray, A.J., et al., "Small bowel perforation following vacuum suction drainage," J. R. Coll. Surg. Edinb. 30(5):324-5 and additional sheet, (Oct. 1985).
Kumar, A.R., "Standard wound coverage techniques for extremity war injury," J. Am. Acad. Orthop. Surg., 14:S62-S65, (2006).
Helgeson, M.D., et al., "Bioartificial dermal substitute: A preliminary report on its use for the management of complex combat-related soft tissue wounds," J. Orthop. Trauma, 21(6):394-399, (Jul. 2007).
Ingari, J.V., et al., "Civilian and detainee orthopaedic surgical care at an air force theater hosptial," Tech. Hand Upper Extr. Surg., 11(2):130-134, (2007).
Covey, D.C., "Combat orthopaedics: A view from the trenches," J. Am. Acad. Orthop. Surg., 14:S10-S17, (2006).
Andersen, R.C., et al., "Definitive treatment of combat casulties at military medical centers," J. Am. Acad. Orthop. Surg., 14:S24-S31, (2006).
Wagner, D. R., et al., "Bioelectrical impedance as a discriminator of pressure ulcer risk," Adv. Wound Care, 9 (2):30-37, (1996).
Mulder, G.D., et al., "Prospective randomized study of the efficacy of hydrogel, hydrocolloid, and saline solution-moistened dressings on the management of pressure ulcers," Wound Rep. Reg., 1:213-218, (1993).
Tintle, T.E., et al., "Early experience with a calcium alginate dressing," Ostomy/Wound Management, pp. 74-81, (May/Jun. 1990).
Jeter, K.F., et al., "Comprehensive wound management with a starch-based copolymer dressing," J. Enterostom. Ther., 13(6):217-225, (Nov.-Dec. 1986).
Winter, G.D., "Formation of the scab and the rate of epithelization of superficial wounds in the skin of the young domestic pig," Nature, No. 4812, p. 293-294 (Jan. 20, 1962).
Robson, M.C., et al., "Bacterial quantification of open wounds," Military Medicine, pp. 19-24, (Jan. 1969).
Jackson, D.M., "The diagnosis of the depth of burning," Br. J. Surgery, 40(164):588-596 and 7 additional sheets, (May 1953).
Morykwas, M.J., "38: Vacuum-assisted closure of wounds" in "Wound Healing," A. Falabella et al., eds., Taylor & Francis, NY, pp. 503-515, (2005).
DeFranzo, A.J., et al., "Vacuum assisted closure for the treatment of abdominal wounds," Clin. Plast. Surg. 33(2): 213-224 (Apr. 2006).
Defranzo, A.J., et al., "Vacuum-assisted closure for defects of the abdominal wall," Plast. Reconstr. Surg., 121 (3):832-839, (Mar. 2008).
Park, C.A., et al., "Breast asymmetry: presentation of a giant fibroadenoma," Breast J., 12(5):451-461, (2006).
Zannis, J., et al., "Comparison of fasciotomy wound closures using traditional dressing changes and the Vacuum-Assisted Closure device," Ann. Plast. Surg., 62(4):407-409, (Apr. 2009).
Thompson, J.T., et al., "Outcome analysis of helmet therapy for positional plagiocephaly using a three-dimensional surface scanning laser," J. Craniofasc. Surg., 20(2):362-365, (Mar. 2009).
Argenta, L.C., et al., "Advances in hemangioma evaluation and treatment," J. Craniofac. Surg., 17(4):748-755 (Jul. 2006).
Plikaitis, C.M., et al, "Neurocutaneous melanosis: clinical presentations," J. Craniofac. Surg., 16(5):921-925 (Sep. 2005).
David, L.R., et al., "Proboscis lateralis: a rare craniofacial anomaly, reconstruction, and long-term evaluation," J. Craniofac. Surg., 19(4):1107-1113, (Jul. 2008).
Sanger, C., et al., "Dynamic spring mediated cranioplasty in an experimental model with resorbable foot plates," J. Craniofac. Surg., 18(1):54-59, (Jan. 2007).
Morykwas, M.J., et al., "Vacuum-assisted closure: state of basic research and physiologic foundation," Plast. Reconstr. Surg., 117(7) (Suppl): 121S-126S, (Jun. 2006).
Hill, C.A., et al., "Superior sternal cleft repair using autologous rib grafts in an infant with complex congenital heart disease," Ann. Thorac. Surg., 84:673-4, (2007).
McGee, M.P., et al., "Swelling and pressure-volume relationships in the dermis measured by osmotic-stress technique," Am. J. Physiol. Regul. Integr. Comp. Physiol., 296:R1907-R1913, (Mar. 25, 2009).

Morykwas, M., "Vacuum assisted closure," 91 sheets of slides.
Morykwas, M., et al., "El use de la plantilla de regeneracion integra en la cirugia reconstructiva," 121 sheets of slides.
Morykwas, M., et al., "Aplicaciones de tratamientos con presion sub-atmosferica en el cuidado de quemaduras," 140 sheets of slides.
Argenta, A., et al., "Deformation of superficial and deep abdominal tissues with application of a controlled vacuum", 1 sheet.
Taber's Cyclopedic Medical Dictionary, 16th edition, pp. 613-614, 643, 679, 1444, and 1686-1688, (1989).
Parker, S.P., ed., McGraw-Hill Dictionary of Scientific and Technical Terms, 4th ed., pp. 1462, (1989).
Gove, P.B., ed., Webster's Third New International Dictionary Unabridged, pp. 869 and 2627 (1986).
Peacock, Jr., E.E., Wound Repair, 3d edition, W.B. Saunders Company pp. 12-14, pp. 38-51, Chapter 6 Repair of skin wounds, (1984).
Spartanburg Regional Medical Center Operative reports, 35 sheets, dated 1989.
Johnson, F.E., "Expanded use of suction drains," pp. 469 and 1 sheet of drawings (allegedly dated 1985).
Brossy, J.-J., "Foam elastomer dressings in surgery," SA Medical Journal, 59:559-560, (Apr. 1981).
Groves, A.R., et al., "Silastic foam dressing: an appraisal," Annals of the Royal College of Surgeons of England, vol. 67, pp. 117-118 and additional page, (1985).
Harding, KG., et al., "Silastic foam dressing for skin graft donor sites—a preliminary report," Br. J. Plast. Surg., 33:418-421, (1980).
Malone, W.D., "Wound dressing adherence: a clinical comparitive study," Archives of Emergency Medicine, 4:101-105, (1987).
Moblvac II advertising materials, 4 sheets, allegedly dated 1984.
Bucknall, T.E. ed., et al., "Wound healing for surgeons," Introduction, Chapter 1 The healing wound, Chapter 2 Wound strength, Chapter 3 Factors affecting healing, Chapter 4 Sutures and dressings, Chapter 5 Clinical trials, Chapter 6 Skin healing and burns, and Chapter 7 The abdominal wall, (1984).
Brubacher, L.L., "To heal a draining wound," RN, 45(3):30-36 (Mar. 1982).
Dahlin, P.A., et al., "Cerebrospinal fluid leak because of pressure sore fistula in a quadriplegic," Spine, 12(1):72-75, (1987).
Downie, P.A., ed., Cash's textbook of medical conditions for physiotherapists, Chapter 1 Inflammation and healing, Chapter 2 Oedema, Chapter 19 Skin conditions, Chapter 20 Burns, B. Lippincott Co., (1979).
Ersh, Z. Ya., "Use of polyurethane foam for cleaning of purulent cavities and wounds,"I.I. Grekov J. of Surg., 133 (9):134-135 and additional sheets (10 sheets in English and 5 sheets in Russian) (1984).
Fasol, R, et al., "The foil vacuum dressing for the treatment of infected skin defects," Acta Chir. Austriaca 116-118, (2 sheets English and 3 sheets German) (1976).
Gruendemann, B.J., et al., Alexander's Care of the patient in surgery, 8th ed., C.V. Mosby Co., pp. 138-139 (1987).
Kirk-Othmer Encyclopedia of chemical technology, 3d ed., vol. 8, pp. 201-203 (1979).
Kostyuchenok, B.M., et al., "Vacuum treatment of purulent wounds," Soviet Medicine, pp. 18-21, (4 sheets English, 4 sheets Russian, with English abstract on last page), (1984).
Kuzin, M.I., et al., "Method of vacuum treatment of wounds," Wounds and Wound Infection, pp. 348-350, (2 sheets) (1981).
Kuzin, M.I., ed., et al., "Vacuum treatment of a purulent wound," Wounds and Wound Infection, Handbook for Physicians, 2nd revised and supplemented ed., pp. 243-246, (3 sheets) (1990).
Tranchell, H.G., et al., Circulatory Ulcers A Physical Approach, John Wright & Sons Ltd., Bristol, Foreword, I. Ulcers: a comparison, II. The ulcer, pp. 44-47, and 54-55, (1960).
Parish, L.C., et al., "The infected decubitus ulcer," Int. J. Dermatol., 28:643-647 (Dec. 1989).
Davydov, Y.A., et al., "Device and method for vacuum therapy of purulent lactation mastites," Khirurgiya, (4):131-132, (Apr. 1988).
Davidov, Y.A., et al., "Justifying the usage of forced early secondary sutures in treatment of purulent wounds by the vacuum therapy," Vestnik Chirugia 126-129, (2 sheets in English aDAVIDOV, Y.A., et al., "Justifying the usage of forced early secondary sutures in treatment of purulent wounds by the vacuum therapy," Vestnik Chirugia

(56) References Cited

OTHER PUBLICATIONS 126-129, (2 sheets in English and 3 sheets in Russian) (Mar. 1990). DV16nd 3 sheets in Russian) (Mar. 1990).
Davydov, Y.A., et al., "Pathogenic mechanisms of the effect of vacuum therapy on the course of the wound process," Khirurgiya, 6:42-47 (7 sheets English and 8 sheets Russian, with English abstract on pp. 46-47) (1990).
Davydov, Y.A., et al., "Bacteriological and cytological evaluation of vacuum therapy of purulent wounds", Vestnik khirurgii, 10:48-52, (5 sheets English, 5 sheets Russian, English abstract on pp. 52) (Received 1987).
Davydov, Y.A., et al., "Vacuum therapy in the treatment of purulent lactation mastitis," pp. 66-70 (5 sheets English, 5 sheets Russian, English abstract on pp. 70) (Received 1986).
Davydov, Y.A., et al., "Vacuum therapy in the treatment of acute purulent diseases of soft tissues and purulent wounds", Vest. Khir. 141(9):43-46 (6 sheets English, 6 sheets Russian, English abstract on pp. 46) (1988).
Svedman, P., "A dressing allowing continuous treatment of a biosurface," IRCS Medical Science: Biomedical Technology; Clinical Medicine; Surgery and Transplantation, 7:221 (1979). (Exhibit D-407).
Davydov, Y., et al., "Bacteriological and Cytological Assessment of Vacuum Therapy of Purulent Wounds," Vestn. Khir., 48-52, English translation by IRC, (Oct. 1988). (Exhibit D-290).
Davydov, Y., et al., "Vacuum Therapy in the Treatment of Purulent Lactation Mastitis," Vestn. Khir. p. 66-70, English translation by IRC, (Sep. 1986), (Exhibit D-292).
Meyer, W., et al., "Bier's Hyperemic Treatment," W.B. Saunders & Co., 1908 (Exhibit D246).
Chariker/Jeter/Tintle Slides "Closed Wound Suction" by Dr. Mark Chariker et al., 41 sheets, pp. 1-10, 19, 55-84 (D-041) (allegedly dated 1985 and 1986).
Jeter, K., list of publications, 4 sheets, (D-161).
Spahn, J.G., "Soft tissue challenges in the head and neck region,"Clinical Seminar Handout, EHOB, (46 pages).
Mendez-Eastman, S., "Guidelines for using negative pressure wound therapy", Adv. Skin Wound Care, 14 (6):314-323. (16 pp.) (Nov.-Dec. 2001).
Addition to the "Users Manual Concerning Overflow Protection—Concerns all Egnell Pumps", dated Feb. 3, 1983, 1 page Swedish, [1 page English].
Aeros, "Moblvac,""introducing the 'off the wall' vacuum system," Aeros Instruments, Life Support Nursing, 3(1):34-37, Barlin Publishing Ltd. (Jan.-Feb. 1980).
Article in Russian, pp. 84-85.
Austad, E.D., et al., "Tissue expansion: dividend or loan?" Plast. Reconstr. Surg.,78(1):63-67 (Jul. 1986).
BlueSky Medical, 2 sheets of advertisement, "Introducing the Chariker-Jeter wound drainage kit" and "Introducing the Kremlin® wound drainage kit".
Egnell Minor, Instruction Book, First Addition [Edition], allegedly dated Feb. 1987, 21 pages Swedish, 3 pages English.
Feierabend, T.C., et al., "Injuries causing major loss of scalp", Plast. Reconstr. Surg., [Abstract only—1 pp. printout from PubMed], 76(2):189-194 (Aug. 1985).
Geronemus, R.G., et al., "The effect of two new dressings on epidermal wound healing", J. Dermatol. Surg. Oncol., 8(10):850-852 (Oct. 1982).
Miller, S.H., et al., "An inexpensive wound suction device", Surg. Gyencol. Obstet., 141(5):768 (Nov. 1975).
Miller, S.J., "Surgical wound drainage system using silicone tubing", J. Am. Podiatry Assn., 71(6): pp. 287-296, (Jun. 1981).
Nelson, R.P., et al., "Use of negative pressure suction in urology", Urology, 4(5):574-576, (Nov. 1974).
Svedman, "Irrigation Treatment of Leg Ulcers", The Lancet, Sep. 3, 1983, pp. 532-534.
Stewart, A., et al., "Cleaning v. healing," Community Outlook, pp. 22, 24 & 26 (Aug. 14, 1985).

Trammell, T.R., et al., "Closed-wound drainage systems: the Solcotrans Plus versus the Stryker-CBC ConstaVAC", Orthopaedic Review, 20(6):536-542 (Jun. 1991).
Woodley, D.T., et al., "A double-blind comparison of adhesive bandages with the use of uniform suction blister wounds", Arch. Dermatol., 128(10):1354, 1357 (Oct. 1992).
Zelko, J.R., et al., "Primary closure of the contaminated wound; closed suction wound catheter", Am. J. Surgery, 142:704-706, (Dec. 1981).
PCT/US08/79364—Written Opinion and International Search Report (Dec. 16, 2008).
Bagautdinov, N.A., "Variant of external vacuum aspiration in the treatment of purulent disease of soft tissue," pp. 94-96 and Introduction by V.E. Volkov and an opinion by V. V. Shutova dated Feb. 4, 2009, in Russian with English translation, with alleged card catalogue card with English translation, and certification of translation dated Feb. 19, 2009, Current Problems in Modern Clinical Surgery, (1986).
Kuznetsov, V.A., "Vacuum and vacuum-sorption treatment of open septic wounds," in II All-union conference "Wounds and wound infection" "(Abstracts of presentations)" in Russian with English translation, and card with English translation, Moscow, Oct. 28-29, 1986. (BAGAUTDINOV II).
Robson, M.C., et al., Chapter 10 "Wounds and wound healing," p. 107-114 in Essentials of General Surgery, P.F. Lawrence ed., Williams & Wilkins, (1988).
Robson, M.C., et al., Chapter 11 "Wounds and wound healing," p. 119-126 in Essentials of General Surgery, 2nd edition, P.F. Lawrence ed., Williams & Wilkins, (1992).
Smith, D.J. Jr., et al., Chapter 7 "Wounds and wound healing," p. 113-122 in Essentials of General Surgery, 3d edition, P.F. Lawrence ed., Lippincott Williams & Wilkins, (2000).
Talboy, G.E., et al., "Chapter 8: Wounds and wound healing," p. 147-161 in Essentials of General Surgery, B. Sun ed., Lippincott Williams & Wilkins, (2006).
Garrison, R.N., et al., "Chapter 9: Surgical infections," p. 163-179 in Essentials of General Surgery, B. Sun ed., Lippincott Williams & Wilkins, (2006).
Sumpio, B.E., et al., "Role of negative pressure wound therapy in treating peripheral vascular graft infections," Vascular, 16(4):194-200, (2008).
Taber's Cyclopedic Medical Dictionary, Edition 20, pp. 306-309, 728-729, 765, 1726, and 2006-2009. (2005).
Mills, N., Polymer Foams Handbook: engineering and biomechanics applications and design guide, pp. 2-3, (2007).
Bucknall, T.E., et al.. eds., "Sutures and dressings," p. 88-93 in Wound Healing for Surgeons, (1984).
Parker, S.P., ed., McGraw-Hill Dictionary of Scientific and Technical Terms, 5th ed., pp. 139, 533, 772, and 1672 (1994).
Alger, M.S.M., Polymer Science Dictionary, (4 sheets), Elsevier Science Publishers Ltd. (1989).
Stedman's Medical Dictionary, 25th ed., pp. 554, 667-668, and 1603-1604, Williams & Wilkins, (1990).
Webster's New World Dictionary of the American Language, pp. 1105, Simon & Schuster, Inc., (1984).
Transeal transparent wound dressing, DeRoyal, 4 sheets (2003).
Kuznetsov, V.A., "Vacuum and vacuum-sorption treatment of open septic wounds," in II All-union conference "Wounds and wound infections" "(Presentation abstracts)" in Russian with English translation dated Apr. 2, 2009, with table of contents, Moscow, Oct. 28-29, 1986.
British Pharmacopoeia 19, vol. II, p. 927 and p. 548 of 1986 addendum, (vol. II—1980, addendum—1986).
KCI, "The V.A.C. operations summary," 7 sheets, (1999).
Kanshin, N.N., "Closed treatment of suppurative processes by the method of active lavage drainage," Third Surgical Clinic of the N.V. Sklifosovkiy Moscow Scientific Research Institute of Emergency Care, pp. 18-23, (6 sheets in English, 6 sheets in Russian and English abstract on pp. 22-23), allegedly submitted 1979.
Lokhvitskii, S.V., et al., "External vacuum aspiration in the treatment of purulent disorders of the soft tissues," Inpatient Surgery Clinic of the Therapeutic Department at Karagandy Medical Institute, Munici-

(56) References Cited

OTHER PUBLICATIONS pal Hospital No. 1, Temirtau, pp. 130-134 (5 sheets English, 5 sheets Russian), allegedly submitted Sep. 22, 1982.

Ersh, Z. Ya., "Use of polyurethane foam for treating purulent cavities and wounds," Purulent Septic Unit of Hospital No. 35, (2 sheets English and 2 sheets Russian), allegedly submitted for publication Mar. 21, 1984.

3M™ Tegaderm™ Transparent film dressings—wound, Commonly asked questions, 4 sheets, (Jan. 2007).

Greene, A.K., et al., "Microdeformational wound therapy," Ann. Plast. Surg., 56(4):418-422, (2006).

Bui, T.D., et al., "Negative pressure wound therapy with off-the-shelf components," Am. J. Surg., 192:235-237, (2006).

Larichev, A.B., et al., "Vacuum-therapy in the complex of treatment of festering wounds," Khirurgiia (Mosk.), 6:22-26, (13 sheets English translation, 5 sheets in Russian, English abstract on pp. 22), (2008).

Scherer, S.S., et al., "The mechanism of action of the vacuum-assisted closure device," Plast. Reconstr. Surg., 122: 786-797, (presented at the Wound Healing Society Meeting 2007 in Tampa, Florida, Apr. 28-May 1, 2008.

Marks, M.W., et al., "Principles & Applications of Vacuum Assisted Closure (VAC)" Plastic Surgery Secrets, 2nd ed., Mosby Elsevier, (2010).

Bonnamy, C., et al., "Use of the vacuum-assisted closure system for the treatment of perineal gangrene involving the abdominal wall", Ann. Chir., (English abstract on first page and 1 sheet PubMed abstract) 125(10):982-4 (Dec. 2000).

Meyer, W., et al., excerpts from "Bier's Hyperemic Treatment", W.B. Saunders and Co., (48 sheets) (1908).

Wong, S.L., et al., "Loxoscelism and negative pressure wound therapy (Vacuum-assisted closure): a clinical case series," Am. Surg., 75:1128-1131, (Nov. 2009).

Covey, D.C. et al., "Orthopaedic war injuries: From combat casulty care to definitive treatment: A current review of clinical advances, basic science, and research opportunities," Instr. Course Lect. 57:65-86 (2008).

Pirela-Cruz, M.A., et al., "Management of large soft-tissue wounds with negative pressure therapy—lessons learned from the war zone," J. Hand Ther. 21:196-203, (2008).

Vertrees, A., et al., "Modern management of complex open abdominal wounds of war: A 5-year experience," J. Am. Coll. Surg., 207:801-809, (2008).

Geiger, S., et al., "War wounds: Lessons learned from Operation Iraqi Freedom," Plast. Reconstr. Surg., 122:146-153, (2008).

Hospenthal, D.R., et al., "Guidelines for the prevention of infection after combat-related injuries," J. Trauma, 64(3): S211-S220, (2008).

Murray, C.K., et al., "Prevention and management of infections associated with combat-related extremity injuries," J. Trauma, 64(3):S239-S251, (2008).

Campbell, P.E., et al., "Retrospective clinical evaluation of gauze-based negative pressure wound therapy," Int. Wound J., 5(2):280-286, (2008).

PCT/US08/30581—Written Opinion and International Search Report (Feb. 20, 2009).

U.S. Appl. No. 11/678,403—Official action (Nov. 24, 2008).

PCT/US08/50584—Written Opinion and International Search Report (Jul. 25, 2008).

Vacuum Assisted Closure (V.A.C.(R)) Therapy: an overview of scientific, clinical, and cost effectiveness evidence, (19 sheets) KCI Licensing, Inc., 2009.

Merriam-Webster Online, "reepithelialization," printout of webpage dated Apr. 17, 2009.

Oxford English Dictionary Online, "deformable," "deform," and "flexible," printout of webpages dated Apr. 17, 2009.

Murphey, G.C., et al., "Depth of penetration of negative pressure wound therapy into underlying tissues," Wound Repair and Regeneration, 17:113-117 (2009).

Jargin, S.V., "Limited access to foreign medical literature in Russia," Chartered Institute of Library and Information Professionals Health Libraries Group Newsletter, 25(4):7-10, (Dec. 2008).

Website printout "Chemical of the week" polymers, 5 sheets, printout dated Apr. 17, 2009.

Chariker, M.E., et al., "An algorithmic approach to the use of gauze-based negative-pressure wound therapy as a bridge to closure in pediatric extremity trauma," Plast. Reconstr. Surg., 123:1510-1520, (2009).

Cornelius, M., "Care in the air: Bringing the wounded closer to home," Plast. Surg. Nurs., 29(3):165-168, (Jul.-Sep. 2009).

Kumar, A.R., et al., "Lessons from Operation Iraqi Freedom: Successful subacute reconstruction of complex lower extremity battle injuries," Plast. Reconstr. Surg., 123:218-229, (2009).

U.S. Appl. No. 12/351,331—Official Action (Dec. 21, 2011).

Zivadinovic, G., et al., "Vacuum therapy in the treatment of peripheral blood vessels," Timok Medical Journal, Abstract book of the 5th Timok Medical Days, Majdanpek, 6 sheets of English translation, (1986).

Safronov, A.A., "Vacuum therapy for trophic ulcers of the tibia with concurrent skin autoplasty," Dissertation abstract, additional abstract, Moscow, 20 sheets of English translation, (1967).

Safronov, A.A., Abstract of Invention No. 240188, "Device for wound or ulcer treatment," (2 sheets English translation and 2 sheets in Russian) (1969).

Davydov, Y.A., et al., "The bacteriological and cytological assessment of vacuum therapy of purulent wounds", Vestnik Khirurgii imeni I.I. Grekova, (1 sheet of title page and pp. 48-52, 5 sheets of Russian text and English abstract on p. 52); 141(10):48-52, (Oct. 1988).

Davydov, Y.A., et al., "Bacteriological and cytological assessment of vacuum therapy of purulent wounds," (7 sheets of translation, pp. 48-52 of Russian text and English abstract on p. 52); 141(10):48-52 (Oct. 1988).

Davydov, Y.A., et al., "Vacuum therapy in the treatment of purulent lactation mastitis", Vestnik Khirurgii Imeni I.I. Grekova, ( 1 Sheet of Title page and pp. 66-70, 6 sheets of Russian text and English abstract on p. 70); 137 (11):66-70, (Nov. 1986).

Davydov, Y.A., et al., "Vacuum therapy in the treatment of purulent lactation mastitis", (8 sheets of English translation, pp. 66-70 of Russian text, and English abstract on p. 70); 137(11):66-70, (Nov. 1986).

Davydov, Y.A., et al., "Vacuum therapy in the treatment of acute purulent diseases of soft tissues and purulent wounds", (4 sheets of Translation, 4 sheets of Russian text and English abstract on p. 46); 141(9):43-46 (Sep. 1988).

Davydov, Y.A., et al., "Vacuum therapy in treatment of acute purulent diseases of soft tissues and purulent wounds," Vestnik Khirurgii (Surgeon's Herald), No. 9 Medicine Publishers, (5 sheets of translation), (1986).

Thomas, S., "Pain and wound management," Community Outlook, pp. 11-13, 15 and one extra sheet, (Jul. 1989).

Livshits, V.S., "Polymer dressings for wounds and burns (review)," All-Union Scientific-Research Institute for Medical Polymers, Moscow, pp. 515-522, (allegedly published in Pharmaceutical Chemical Journal, 22(7):790-798, translated from Russian (allegedly dated Jul. 1988)), Plenum Publishing Corp., (1989).

Calne, S., ed., Position Document: Pain at wound dressings changes, pp. 1-17 and 3 additional sheets, supported by Molnlycke Health Care, (allegedly dated 2002).

Skover, G., et al., "45: New Technologies: An Overview," Chronic Wound Care, pp. 425-430 (allegedly dated 1990).

2 sheets of documents, the citation is alleged to be: David JA, Wound Management: A Comprehensive Guide to Dressing and Healing, pp. 51-51 (allegedly dated 1986).

Thomas, S., "Selecting dresssings," Community Outlook, vol. 6, 4 sheets, (Jun. 1991).

1 sheet document, the citation is alleged to be: David J., Extract from Practical Nursing Handbook: Wound Management: A Comprehensive Guide to Dressing and Healing, pp. 166-167, (allegedly dated 1986).

(56) References Cited

OTHER PUBLICATIONS

Dunphy, J.E., ed., et al., "Current Surgical Diagnosis & Treatment" 5th ed., pp. 946-951, with 5 additional sheets, Lange Medical Publications, Los Altos, CA (1981).
British Pharmacopoeia, vol. II, pp. 903-940, London (1980).
British Pharmacopoeia 1980, pp. A81, 542, 546-549, with annotations, London—Addendum (1986).
Wagner, D.R., et al., "Combined parenteral and enteral nutrition in severe trauma," Nutrition in Clinical Practice, 7:113-116 with additional sheet, (1992).
Krizek, T.J., et al., "The use of prophylactic antibacterials in plastic surgery: A 1980s update," Plast. Reconstr. Surg., 76(6): 953-962, (Dec. 1985).
Juchli, L., "Krankenpflege [Nursing] Practice and Theory of Promoting Health and Patient Care," Georg Thieme Verlag Stuttgart, labeled as "Anlage 6.1" 1991 (allegedly dated Feb. 1991), and email dated May 30, 2007 labeled as "Anlage 6.2," both in German with English translations.
Fleischmann, W., et al., "Combination osteosynthesis in the treatment of pylon fractures with soft tissue damage," labeled "Anlage NK10," pp. 178-181 and showing "6. German-Austrian-Swiss Trauma Conference in Vienna May 21-25, 1991," published in "Der Unfallchirurg" [The Traumatologist] in 1993, in German with English translation.
"Coldex," labeled as "Anlage NK12" in German with English translation.
Turner, T.D., et al., eds., Excerpts from "Advances in wound management," including "Recent advances in wound management products" by T.D. Turner and "The role of foam dressings in wound management" by S. Thomas, Proceedings of a symposium held at the Welsh School of Pharmacy, University of Wales Institute of Science and Technology, Cardiff, Mar. 20-21, 1985, labeled as "Anlage NK13," 1986.
Fleischmann, W., et al., "Combination osteosynthesis in treating pilon fractures involving soft tissue injuries," in "Translation of an excerpt from the brochure regarding the Sixth German-Austrian-Swiss Accident Congress" allegedly dated 1991, in German with English translation.
ISO 10079-1, "International Standard," "Medical suction equipment—Part 1: electrically powered suction equipment—Safety requirements," dated May 15, 1991.
Leaper, D.J., "The Wound Healing Process," Advances in Wound Management, T.D. Turner, et al., eds., pp. 7-16, New York: John Wiley and Sons, (1986).
Opposition to EP 2 392 302—Communication of Opponent Hartmann dated Nov. 12, 2013 and European Patent Office's Communication of a notice of opposition (and translation) dated Nov. 19, 2013. EPOP2915HARTMANN-001.
Opposition to EP 2 392 302—Communication of Opponent KSNH dated Nov. 12, 2013 and European Patent Office's Communication of a notice of opposition dated Nov. 18, 2013. EPOP2915KSNH-001.
Lindstedt, S., et al., "A compare between myocardial topical negative pressure levels of −25 mmHg and −50 mmHg in a porcine model", BMC Cardiovascular Disorders 2008 8:14, BioMed Central, pp. 1-7. NPL-968.
Lindstedt, S., et al., "Blood Flow Changes in Normal and Ischemic Myocardium During Topically Applied Negative Pressure", Ann Thorac Surgery 2007;84:568-73. NPL-969.

\* cited by examiner

DEVICES AND METHODS FOR TREATING SPINAL CORD TISSUE

RELATED APPLICATIONS

This application claims the benefit of priority of U.S. Provisional Application No. 60/978,884, filed on Oct. 10, 2007, U.S. Provisional Application No. 61/081,997, filed on Jul. 18, 2008, and U.S. Provisional Application No. 61/088,558, filed on Aug. 13, 2008, the entire contents of which applications are incorporated herein by reference.

FIELD OF THE INVENTION

The present invention relates generally to devices and methods for treating damaged or compromised spinal cord tissue using sub-atmospheric pressure and more particularly, but not exclusively, to devices and methods for treating spinal cord tissue that have experienced a recoverable or non-recoverable injury.

BACKGROUND OF THE INVENTION

The anatomy, physiology, and pathologic processes that involve the spinal cord pose special concerns for the treatment of damaged or compromised spinal cord tissue. The preservation of both the three-dimensional structural anatomy and the microanatomical relationships of neurons (whose function depends on specific spacial relationships with other neurons and other supporting cells), as well as the maintenance of properly oxygenated blood flow and the homogeneous ground substance matrix in which the neurons survive, are vital to the survival and function of spinal cord tissues. Moreover, the inability of spinal cord cells to regenerate emphasizes the need to maximize survival of every possible neuron. For reasons such as these, treatment of both open and closed space pathology in the spinal cord poses special concerns.

Among the clinical problems that threaten survival of spinal cord tissue, the control of spinal cord edema, infection, and blood supply are central. The spinal cord responds to trauma and injury by collecting a significant amount of interstitial edema. Because the spinal cord is enclosed in a closed space (dura and the spinal canal), edema results in compression and compromise of the blood flow and nutritional performance of the spinal cord, which greatly impairs physiological recovery of the spinal cord and often of itself results in progression of compromise and death of the spinal cord. Currently available treatments for reducing edema include pharmacologic agents, such as glucocorticoids (Dexamethasone, Prednisone, Methyl Prednisolone), diuretics, and extensive surgical decompression. However, disadvantages to these treatments include irregular and unpredictable results, complications of the drugs, infection, and surgical complications.

The need for rapid and effective treatment is also vital due to the disastrous consequences and high likelihood of rapid propagation of infection and edema in the spinal cord. At present there are few successful methods available to treat pathologies affecting the intraspinal space, spinal cord parenchyma, and the surrounding structures. Where tissues elsewhere in the body can be treated with dressing changes, the spinal cord is not amenable to this type of treatment because of its precarious structure, propensity for infection, and potential for progression of injury. There is evidence that inflammation and immunological response to spinal cord trauma and other pathology are of equal or greater long term consequences than the initial trauma or insult. The response of the spinal cord to decreased blood flow secondary to edema results in hypoxia and ischemia/reperfusion-mediated injury. These injuries contribute to the neuropathological sequella, which greatly contribute to the adverse outcome of spinal injury.

In addition, the spinal cord requires a continuous supply of oxygenated blood to function and survive. Within a few minutes of complete interruption of blood flow to the spinal cord, irreversible spinal cord damage results. The spinal cord can, however, remain viable and recover from reduced blood flow for more prolonged periods. There is evidence that focal areas of the spinal cord can remain ischemic and relatively functionless for days and still recover. This finding has led to the concept of an ischemic zone, termed the penumbra or halo zone, that surrounds an area of irreversible injury. A secondary phenomena in the ischemic zone is the release of excitotoxins that are released locally by injured neurons, alterations in focal blood flow, and edema.

Vascular pathology of the spine may be a result of: inadequate blood flow to the spinal cord cells from decreased perfusion pressure, rupture of a blood vessel resulting in direct injury to the local spinal cord area, or by compression of adjacent tissue; intrinsic disease of the spinal cord blood vessels such as atherosclerosis, aneurysm, inflammation, etc.; or a remote thrombus that lodges in the spinal cord blood vessels from elsewhere such as the heart.

In cases of intraspinal hemorrhage, the hemorrhage usually begins as a small mass that grows in volume by pressure dissection and results in displacement and compression of adjacent spinal cord tissue. Edema in the adjacent compressed tissue around the hemorrhage may lead to a mass effect and a worsening of the clinical condition by compromising a larger area of spinal cord tissue. Edema in the adjacent spinal cord may cause progressive deterioration usually seen over 12 to 72 hours. The occurrence of edema in the week following the intraspinal hemorrhage often worsens the prognosis, particularly in the elderly. The tissue surrounding the hematoma is displaced and compressed but is not necessarily fatally compromised. Improvement can result as the hematoma is resorbed, adjacent edema decreased, and the involved tissue regains function.

Treatment of these conditions has been disappointing. Surgical decompression of the spinal cord can be helpful in some cases to prevent irreversible compression. Agents such as mannitol and some other osmotic agents can reduce intraspinal pressure caused by edema. Steroids are of uncertain value in these cases, and recently hyperbaric oxygen has been proposed.

Thus, though the application of negative (or sub-atmospheric) pressure therapy to wounded cutaneous and subcutaneous tissue demonstrates an increased rate of healing compared to traditional methods (as set forth in U.S. Pat. Nos. 5,645,081, 5,636,643, 7,198,046, and 7,216,651, as well as US Published Application Nos. 2003/0225347, 2004/0039391, and 2004/0122434, the contents of which are incorporated herein by reference), there remains a need for devices and methods specifically suited for use with the specialized tissues of the spinal cord.

SUMMARY OF THE INVENTION

The present invention provides devices and methods that use sub-atmospheric (or negative) pressure to treat damaged spinal cord tissue, such as spinal tissue damaged by disease, infection, or trauma, for example, which may lead to the presence of swelling, compression, and compromised blood flow secondary to interstitial edema. For instance, the spinal cord may be damaged by blunt trauma resulting in a recoverable or non-recoverable injury.

In one of its aspects the present invention provides a method for treating damaged spinal cord tissue using sub-atmospheric pressure. The method comprises locating a porous material proximate the damaged spinal cord tissue to provide gaseous communication between one or more pores of the porous material and the damaged spinal cord tissue. The porous material may be sealed in situ proximate the damaged spinal cord tissue to provide a region about the damaged spinal cord tissue for maintaining sub-atmospheric pressure at the damaged spinal cord tissue. The porous material may be operably connected with a vacuum system for producing sub-atmospheric pressure at the damaged spinal cord tissue, and the vacuum system activated to provide sub-atmospheric pressure at the damaged spinal cord tissue. The sub-atmospheric pressure may be maintained at the damaged spinal cord tissue for a time sufficient to decrease edema at the spinal cord. For example, the sub-atmospheric pressure may be maintained at about 25 mm Hg below atmospheric pressure. The method may also include locating a cover over damaged spinal cord tissue and sealing the cover to tissue proximate the damaged spinal cord tissue for maintaining sub-atmospheric pressure at the damaged spinal cord tissue. The cover may be provided in the form of a self-adhesive sheet which may be located over the damaged spinal cord tissue. In such a case, the step of sealing the cover may include adhesively sealing and adhering the self-adhesive sheet to tissue surrounding the damaged spinal cord tissue to form a seal between the sheet and tissue surrounding the damaged spinal cord tissue.

In another of its aspects the present invention provides an apparatus for treating damaged spinal cord tissue. The apparatus may include a porous bio-incorporable material, such as an open-cell collagen, having pore structure configured to permit gaseous communication between one or more pores of the porous material and the spinal cord tissue to be treated. The bio-incorporable nature of the porous material can obviate the need for a second procedure to remove the porous material. (As used herein the term "bio-incorporable" is defined to describe a material that may be left in the patient indefinitely and is capable of being remodeled, resorbed, dissolved, and/or otherwise assimilated or modified.) The apparatus also includes a vacuum source for producing sub-atmospheric pressure; the vacuum source may be disposed in gaseous communication with the porous material for distributing the sub-atmospheric pressure to the spinal cord tissue. The porous material may have, at least at a selected surface of the porous material, pores sufficiently small to prevent the growth of tissue therein. In addition, the porous material may have, at least at a selected surface of the porous material, a pore size smaller than the size of fibroblasts and spinal cord cells, and may have a pore size at a location other than the selected surface that is larger than that of fibroblasts and spinal cord cells. The pore size of the porous material may be large enough to allow movement of proteins the size of albumin therethrough. Also, the porous bio-incorporable material may include at least one surface that is sealed to prevent the transmission of sub-atmospheric pressure therethrough. The apparatus may also include a cover configured to cover the damaged spinal cord tissue to maintain sub-atmospheric pressure under the cover at the damaged spinal cord tissue.

Thus, the present invention provides devices and methods for minimizing the progression of pathologic processes, minimizing the disruption of physiological spinal cord integrity, and minimizing the interference with spinal cord blood flow and nutrition. By decreasing spinal cord edema and intraspinal pressure the risk of spinal cord herniation and compromise may be minimized. In addition, the present invention facilitates the removal of mediators, degradation products, and toxins that enhance the inflammatory and neuropathological response of tissues in the spinal cord.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Referring now to the figures, wherein like elements are numbered alike throughout, the present invention relates to devices and methods that use sub-atmospheric (or negative) pressure for treating damaged spinal cord tissue, where "damaged" tissue is defined to include tissue that is injured, compromised, or in any other way impaired, such as damage due to trauma, disease, infection, surgical complication, or other pathologic process, for example. More specifically, the devices and methods of the present invention can effect treatment of edema of the spinal cord parenchyma secondary to any cause, such as the aforementioned causes; treatment of any of the spaces surrounding the spinal cord, including the subdural/epidural spaces; and, treatment of elevated intraspinal pressure due to any cause, such as the aforementioned causes.

Figure 1:
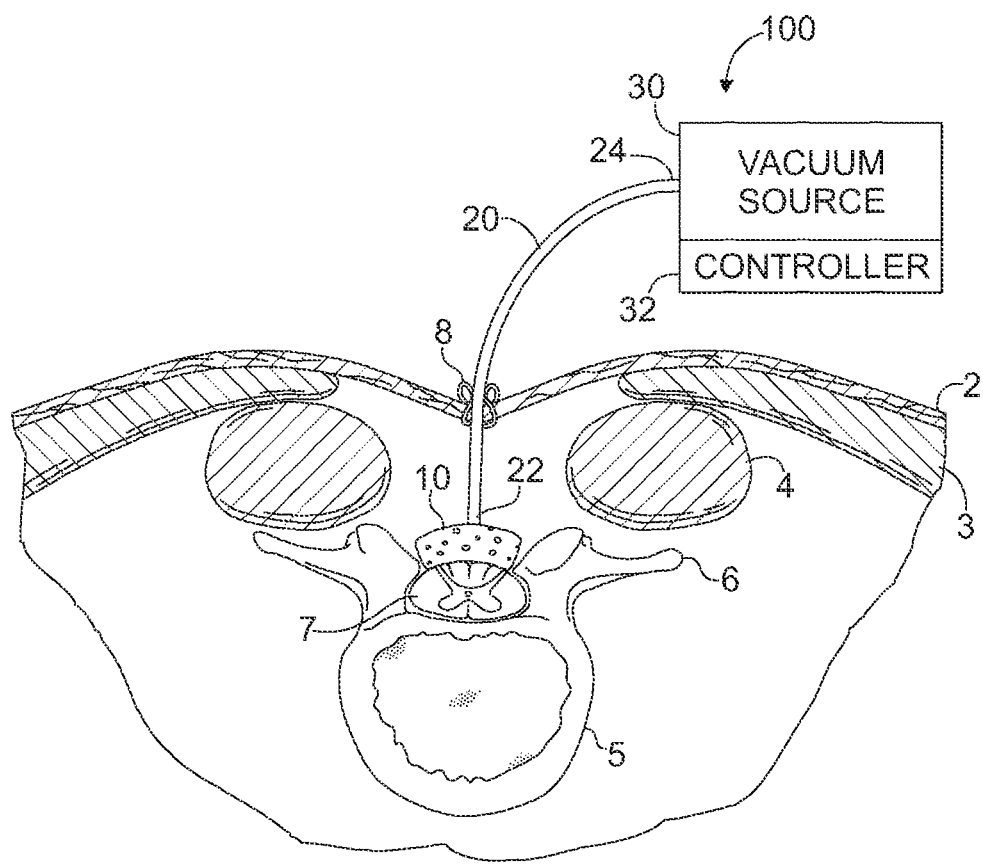
FIG. 1 schematically illustrates a partial cross-sectional view of an exemplary configuration of an apparatus of the present invention in situ prior to the application of sub-atmospheric pressure.
Figure 10:
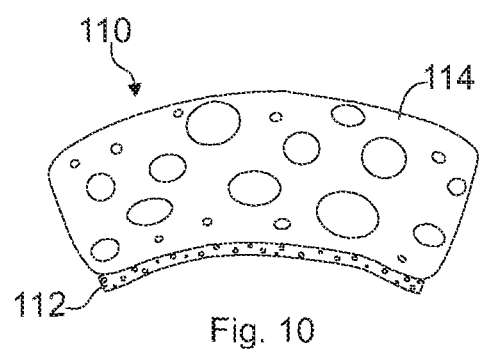
FIG. 10 schematically illustrates a porous material having a multi-layer structure for use in a sub-atmospheric pressure apparatus of the present invention.
Figure 2:
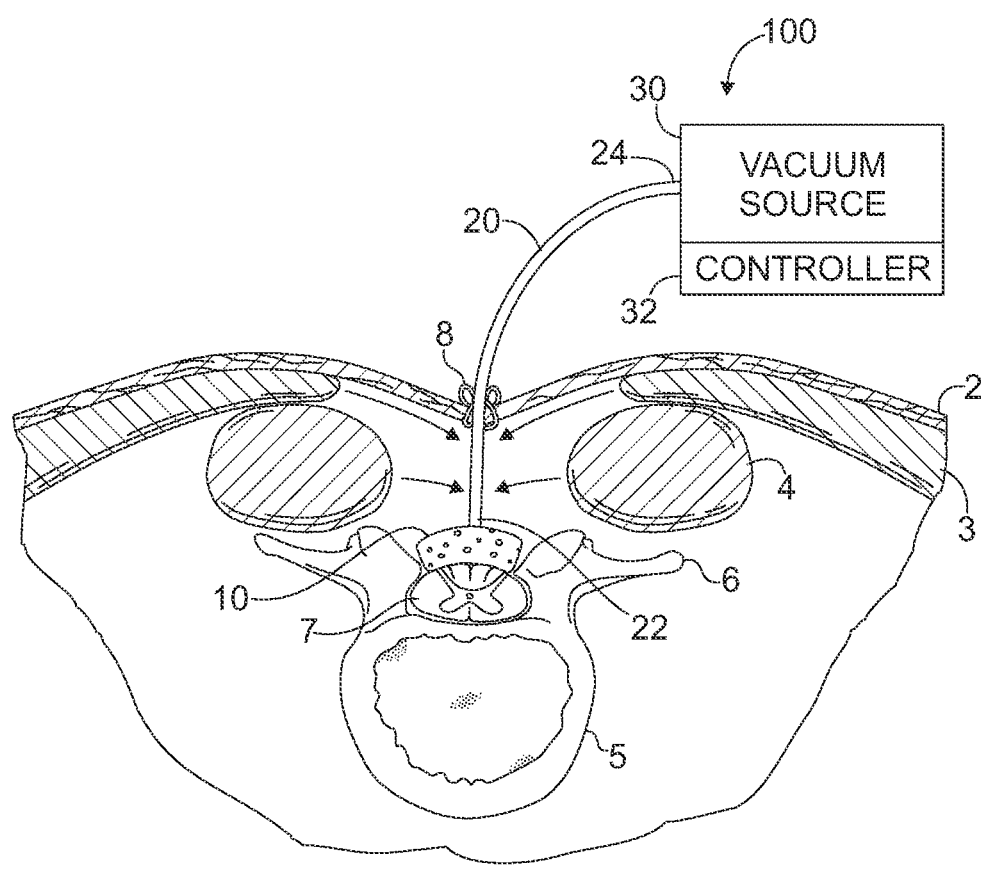
FIG. 2 schematically illustrates the partial cross-sectional view of FIG. 1 as a sub-atmospheric pressure is being applied.
Figure 3:
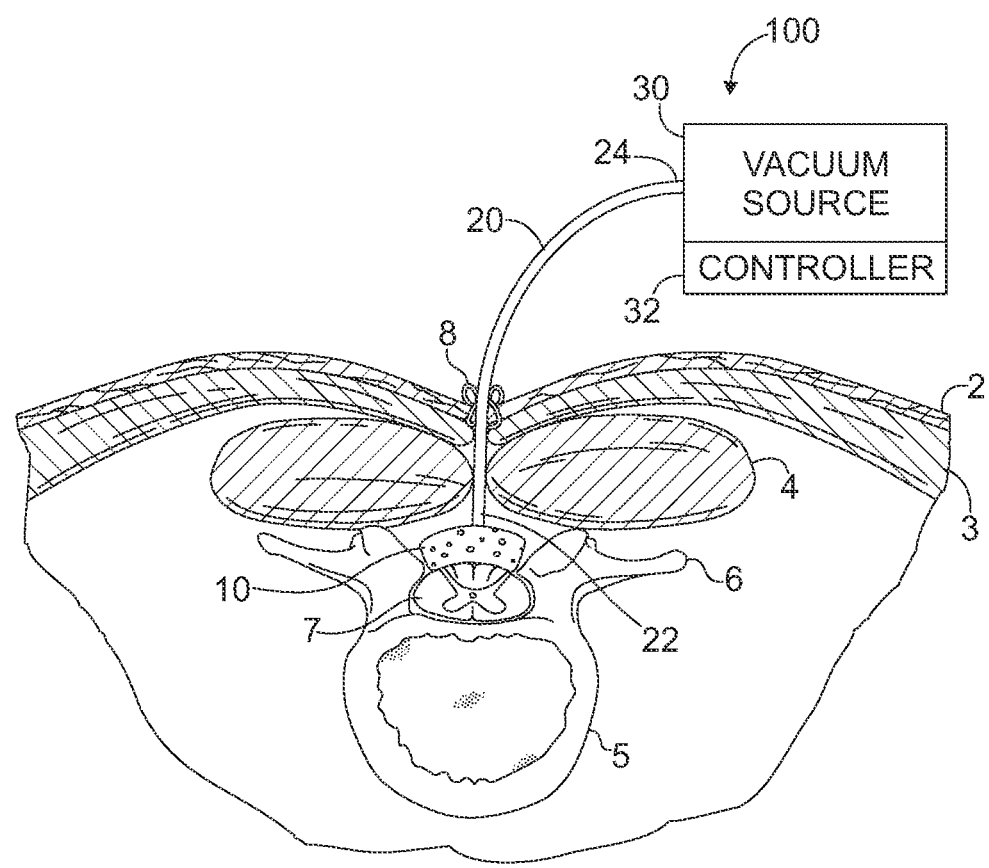
FIG. 3 schematically illustrates the partial cross-sectional view of FIGS. 1 and 2 showing the effect of the applied sub-atmospheric pressure on the tissues surrounding the spinal cord.

An exemplary configuration of a sub-atmospheric spinal cord treatment device 100 of the present invention may include a vacuum source 30 for supplying sub-atmospheric pressure via a tube 20 to a porous material 10 disposed proximate the spinal cord 7, FIGS. 1-3. In this regard, the porous material 10 may be structured to deliver and distribute sub-atmospheric pressure to the spinal cord 7. The spinal cord treatment device 100 may be applied to a patient by locating a porous material 10 proximate the damaged spinal cord tissue 7 to provide gaseous communication between one or more pores of the porous material 10 and the damaged spinal cord tissue 7. A tube 20 may be connected to the porous material 10 at a distal end 22 of the tube 20, and the porous material 10 may be sealed in situ by sutures 8 in the skin and subcutaneous tissues 2 to provide a region about the damaged spinal cord tissue 7 for maintaining sub-atmospheric pressure. The proximal end 24 of the tube 20 may be attached to a vacuum source 30 to operably connect the porous material 10 to the vacuum system 30 for producing sub-atmospheric pressure at the damaged spinal cord tissue 7 upon activation of the vacuum system 30.

Turning to FIG. 1 in greater detail, an exemplary configuration of a sub-atmospheric spinal cord treatment device 100 of the present invention is illustrated in situ in a patient with surrounding tissues shown in partial cross-section. The tissues illustrated include the skin and subcutaneous tissue 2, muscle tissue, such as the trapezius 3 and erector spinae 4, vertebrae 5, transverse process 6, and the spinal cord 7. To provide access to the spinal cord 7, a portion of the vertebrae 5 may be missing. For instance, the spinous process may be absent due to surgical dissection, disease, or injury. A porous material 10, such as an open-cell collagen material, may be placed in the subcutaneous space proximate the spinal cord tissue 7 to be treated with sub-atmospheric pressure to decrease edema in the parenchymal tissues and improve physiologic function, for example. In addition to an open-cell collagen material, the porous material 10 may also include a polyglycolic and/or polylactic acid material, a synthetic polymer, a flexible sheet-like mesh, an open-cell polymer foam, a foam section, a porous sheet, a polyvinyl alcohol foam, a polyethylene and/or polyester material, elastin, hyaluronic acid, alginates, polydiolcitrates, polyhyrdoxybutyrate, polyhyrdoxyfumarate, polytrimethylenecarbonate, polyglycerolsebecate, aliphatic/aromatic polyanhydride, or other suitable materials, and combinations of the foregoing any of which may be fabricated by electrospinning, casting, or printing, for example. Such materials include a solution of chitosan (1.33% weight/volume in 2% acetic acid, 20 ml total volume) which may be poured into an appropriately sized mold. The solution is then frozen for 2 hours at −70° C., and then transferred to the lyophylizer with a vacuum applied for 24 hours. The material may be cross-linked by 2.5%-5% glutaraldehyde vapor for 12-24 hours (or by ultraviolet radiation for 8 hours) to provide a cast porous material 10.

Additionally, the porous material 10 may be made by casting polycaprolactone (PCL). Polycaprolactone may be mixed with sodium chloride (1 part caprolactone to 10 parts sodium chloride) and placed in a sufficient volume of chloroform to dissolve the components. For example, 8 ml of the solution may be poured into an appropriately sized and shaped contained and allowed to dry for twelve hours. The sodium chloride may then be leached out in water for 24 hours.

It is also possible to use electrospun materials for the porous material 10. One exemplary of a formulation and method for making an electrospun porous material 10 was made using a combination of collagen Type I:chondroitin-6-sulfate (CS):poly 1,8-octanediol citrate (POC) in a ratio of 76%:4%:20%: by weight. Two solvents were utilized for the collagen/CS/POC. The CS was dissolved in water and the collagen and POC were dissolved in 2,2,2-trifluoroethanol (TFE). A 20% water/80% TFE solution (volume/volume) solution was then used. For electrospinning, the solution containing the collagen:CS:POC mixture was placed in a 3 ml syringe fitted to an 18 Ga needle. A syringe pump (New Era Pump Systems, Wantaugh, N.Y.) was used to feed the solution into the needle tip at a rate of 2.0 ml/hr. A voltage of 10-20 kV was provided by a high voltage power supply (HV Power Supply, Gamma High Voltage Research, Ormond Beach. FL) and was applied between the needle (anode) and the grounded collector (cathode) with a distance of 15-25 cm. The material was then cross-linked with glutaraldehyde (Grade II, 25% solution) and heat polymerized (80° C.) for 48 hours. It is also possible to electrospin collagen Type I porous materials 10 starting with an initial concentration of 80 mg/ml of collagen in 1,1,1,3,3,3-hexafluoro-2-propanol (HFP), then use the same electrospinning conditions as the collagen:CS:POC combination.

An additional method for creating porous materials 10 is to use thermal inkjet printing technologies. Bio-incorporable materials such as collagen, elastic, hyaluronic acid, alginates, and polylactic/polyglycolic acid co-polymers may be printed. As examples, Type I collagen (Elastin Products Co., Owensville, Mo.) dissolved in 0.05% acetic acid, then diluted to 1 mg/ml in water can be printed, as can sodium alginate (Dharma Trading Co., San Raphael, Calif.) 1 mg/ml in water. A mixture of Type I collagen (2.86 mg/ml in 0.05% acetic acid) and polylactic/polyglycolic acid (PURAC America, Blair, Nebr.) (14.29 mg/ml in tetraglycol (Sigma Aldrich, St. Louis Mo.)) can also be printed. Hardware from a Hewlett Packard 660c printer, including the stepper motors and carriage for the cartridges, can be mounted to a platform. The height of the hardware above the platform can then be adjusted for printing in layers.

The porous material 10 may comprise pores sufficiently small at the interface between the porous material 10 and the spinal cord 7 to prevent the growth of tissue therein, e.g., a pore size smaller than the size of fibroblasts and spinal cord cells; otherwise the porous material 10 may stick to the spinal cord 7 and cause bleeding or trauma when the porous material 10 is removed. In addition, the pore size at the interface between the porous material 10 and the spinal cord 7 may be sufficiently small so as to avoid the excessive production of granulation or scar tissue at the spinal cord 7 which may interfere with the physiologic function of the spinal cord 7. At the same time, the pore size of the porous material 10 may be large enough to allow movement of proteins the size of albumin therethrough to permit undesirable compounds to be removed, such as mediators, degradation products, and toxins.

The porous material 10 may, however, have a larger pore size (e.g., larger than that of fibroblasts and spinal cord cells) interior to the porous material 10 or at any other location of the porous material 10 that is not in contact with spinal cord tissue 7. For example, the porous material 110 may comprise a multi-layer structure with a non-ingrowth layer 112 having a sufficiently small pore size to prevent the growth of tissue therein for placement at the spinal cord, and may have an additional layer 114 of a different material that has a relatively larger pore size in contact with the non-ingrowth layer 112.

Alternatively, the porous material 10 may be homogeneous in composition and/or morphology. At a location away from the interface with the spinal cord 7, the porous material 10 may have a pore size sufficiently large to promote the formation of granulation tissue at other tissues in the spaces surrounding the spinal cord 7, such as promotion of granulation tissue in areas where spinal cord disruption has occurred. In addition, the porous material 10 may have a configuration in which one or more sides or surfaces of the porous material 10 are sealed to prevent the transmission of sub-atmospheric pressure through such a sealed surface, while at the same time having at least one surface through which sub-atmospheric pressure may be transmitted. Such a configuration of the porous material 10 can present preferential treatment of tissue on one side of the porous material 10 while not treating the other side. For instance, the parenchyma of the spinal cord 7 could be treated with the non-sealed interface on one side of the porous material 10.

The porous material 10 may be comprised of a material that needs to be removed after sub-atmospheric therapy is given, which could require a second surgery. Alternatively, the porous material 10 may be comprised of a material that is bioabsorbable or degrades harmlessly over time to avoid a second surgery, such as collagen. In addition, the porous material 10 may comprise a non-metallic material so that an MRI can be performed while the porous material 10 is in situ. The porous material 10 may also comprise a material that is sufficiently compliant so that if it presses against the spinal cord 7 the porous material 10 does not interfere with spinal cord function. At the same time, the porous material 10 may comprise a material that is sufficiently firm so that the porous material 10 does not collapsed so much as to create a pull on, or distortion of, the "normal spinal cord" that might interfere with spinal cord function.

To deliver sub-atmospheric pressure to the porous material 10 for distribution to the spinal cord 7, a tube 20 may be connected directly or indirectly in gaseous communication with the porous material 10 at the distal end 22 of the tube 20. For example, the distal end 22 of the tube 20 may be embedded in the porous material 10 or may be placed over the porous material 10. The distal end 22 of the tube 20 may also include one or more fenestrations to assist in delivering the sub-atmospheric pressure to the porous material 10 and the spinal cord 7. The tube 20 may extend through an opening in the skin and subcutaneous tissue 2 which may be secured about the tube 20 with a suture 8 to assist in providing a seal about the tube 20. The proximal end 24 of the tube 20 may be operably connected to a vacuum source 30, such as a vacuum pump, to provide sub-atmospheric pressure that is transmitted via the tube 20 to the porous material 10 and the spinal cord 7.

The vacuum source 30 may include a controller 32 to regulate the production of sub-atmospheric pressure. For instance, the vacuum source 30 may be configured to produce sub-atmospheric pressure continuously or intermittently; e.g. the vacuum source 30 may cycle on and off to provide alternating periods of production and non-production of sub-atmospheric pressure. The duty cycle between production and non-production may be between 1 to 10 (on/off) and 10 to 1 (on/off). In addition, intermittent sub-atmospheric pressure may be applied by a periodic or cyclical waveform, such as a sine wave. The vacuum source 30 may be cycled after initial treatment to mimic a more physiologic state, such as several times per minute. The sub-atmospheric pressure may be cycled on-off as-needed as determined by monitoring of the pressure in the spinal cord 7. In general, the vacuum source 30 may be configured to deliver sub-atmospheric pressure between atmospheric pressure and 75 mm Hg below atmospheric pressure to minimize the chance that the sub-atmospheric pressure may result in bleeding into the spinal cord 7 or otherwise be deleterious to the spinal cord 7. The application of such a sub-atmospheric pressure can operate to remove edema from the spinal cord 7, thus preserving neurologic function to increase the probability of recovery and survival in a more physiologically preserved state.

Figure 4:
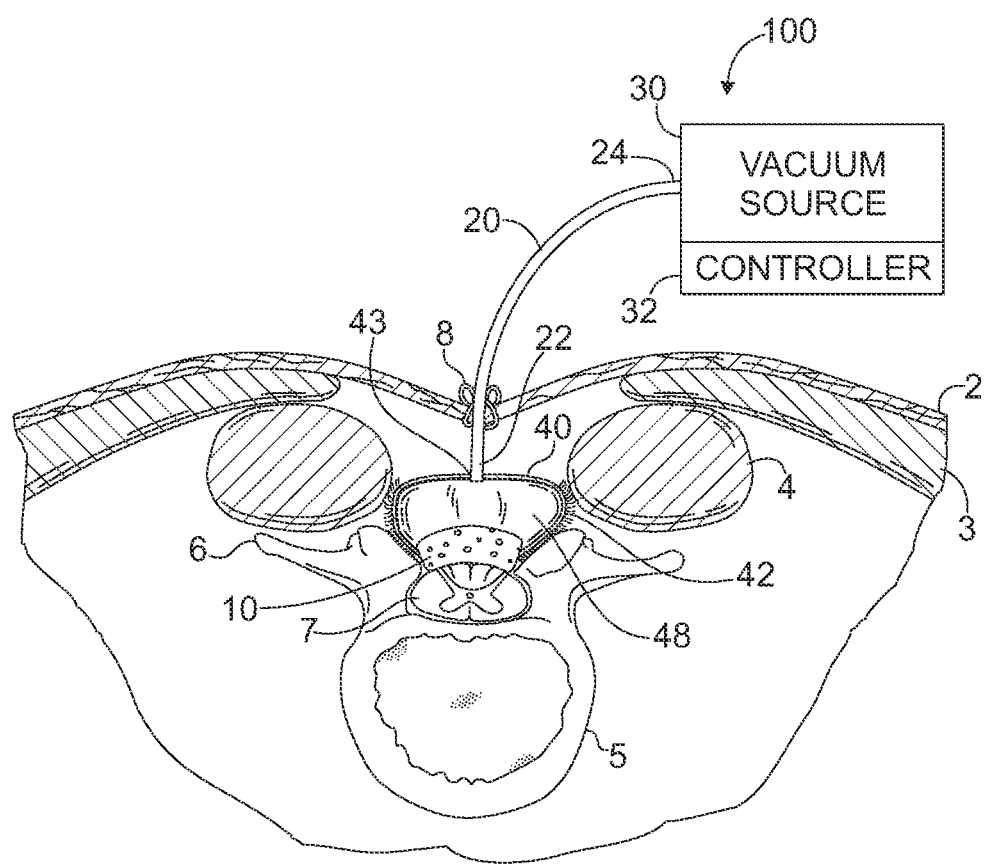
FIG. 4 schematically illustrates a partial cross-sectional view of a second exemplary configuration of the present invention in situ comprising a rigid or semi-rigid cover disposed subcutaneously over the spinal cord.
Figure 5:
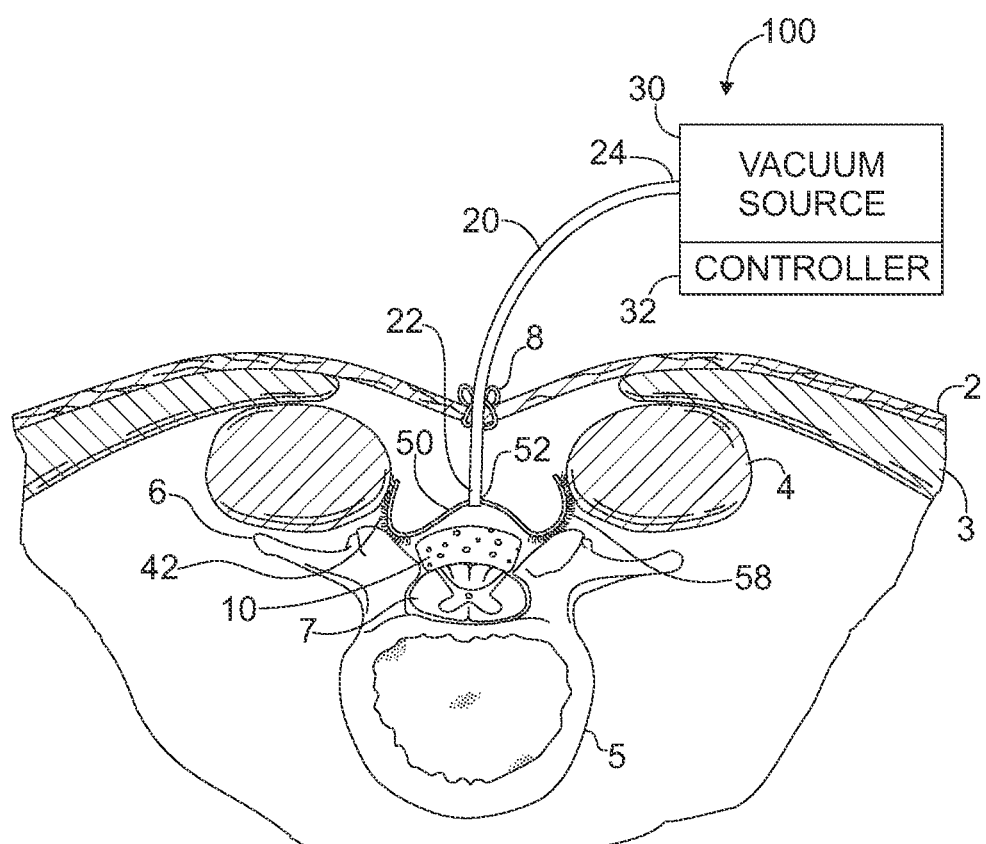
FIG. 5 schematically illustrates a partial cross-sectional view of a third exemplary configuration of the present invention in situ comprising a flexible cover disposed subcutaneously over the spinal cord.

To assist in maintaining the sub-atmospheric pressure at the spinal cord 7, a flexible cover/sheet 50 or rigid (or semi-rigid) cover 40 may be provided proximate the spinal cord 7 to provide a region about the spinal cord 7 where sub-atmospheric pressure may be maintained, FIGS. 4, 5. Specifically, with reference to FIGS. 4 and 5, a cover 40, 50 may be provided over the spinal cord 7 and porous material 10 by adhering the cover 40, 50 to tissues proximate the spinal cord 7 to define an enclosed region 48, 58 about the spinal cord 7 and porous material 10. For instance, the cover 40, 50 may be glued to the vertebrate 5, muscle tissue 4, and/or other appropriate tissues using an adhesive 42, such as a fibrin glue. The adhesive 42 may comprise an auto-polymerizing glue and/or may desirably include a filler to provide the adhesive 42 with sufficient bulk to permit the adhesive 42 to conform to the shapes of the potentially irregular surfaces which the adhesive 42 contacts. The adhesive 42 may be provided as a separate component or as a portion of the cover 40, 50 to provide a self-adhesive cover 40, 50. For instance, the cover 50 may comprise a flexible self-adhesive sheet which includes a suitable adhesive on one or more of its surfaces.

For the flexible cover 50, an outside edge or border of the flexible cover 50 may be rolled under (or toward) the spinal cord 7. Alternatively, the flexible cover 50 may be curled out away from the spinal cord 7 so that the underside of the cover 50 (that side facing with the porous material 10) may then contact with the vertebrae 5 and surrounding muscles and soft tissue, FIG. 5. If the flexible cover 50 is rolled under the spinal cord 7, an adhesive 52 may then be applied to the outside of the cover 50 between the cover 50 and the vertebrae 5, surrounding muscle and soft tissues to help promote an airtight seal. If the flexible cover 50 is curled away from the spinal cord 7, an adhesive may be applied to the underside of the cover 50, between the cover 50 and the vertebrae 5 and surrounding muscle and soft tissue to create an airtight seal.

Sub-atmospheric pressure may be delivered under the cover 40, 50 by cooperation between the cover 40, 50 and the tube 20. Specifically, the cover 40 (or flexible cover 50) may include a vacuum port 43 to which the distal end 22 of the tube 20 connects to provide gaseous communication between the tube 20 and the space 48 under the cover 40 over the spinal cord 7, FIG. 4. Alternatively, the cover 50 (or cover 40) may include a pass-through 52 through which the tube 20 passes so that the distal end 22 of the tube 20 is disposed interior to, and in gaseous communication with, the space 58 under the cover 50 over the spinal cord 7, FIG. 5.

The cover 40, 50 may serve to further confine the subcutaneous region about the spinal cord 7 at which sub-atmospheric pressure is maintained. That is, as illustrated in FIGS. 4 and 5, the cover 40, 50 provides an enclosed space/region 48, 58 about spinal cord 7 under the cover 40, 50, which can serve to isolate the tissues exterior to the cover 40, 50 from exposure to the sub-atmospheric pressure applied to the spinal cord 7. In contrast, as illustrated in FIGS. 2 and 3, in the absence of a cover, sub-atmospheric pressure delivered to the porous material 10 and spinal cord 7 may draw the surrounding tissues, such as muscles 3, 4, inward towards the tube 20 and porous material 10 along the directions of the arrows shown in FIG. 2 resulting in the configuration of tissues illustrated in FIG. 3. In this regard the stretched and/or moved tissues, such as muscles 3, 4, can help to confine the applied sub-atmospheric pressure to a region between the muscles 4 and the spinal cord 7. In addition the covers 40, 50 may further protect the spinal cord 7 from exogenous infection and contamination beyond the protection already afforded by the porous material 10 and sutured skin 2. Likewise, the covers 40, 50 may further protect surrounding tissues from the spread of infection from the spinal cord 7 such as spinal cord abscesses, meningitis, and spinal tissue infection.

In another of its aspects, the present invention also provides a method for treating damaged spinal cord tissue using sub-atmospheric pressure with, by way of example, the devices illustrated in FIGS. 1-5. In particular, the method may comprise locating a porous material 10 proximate the damaged spinal cord tissue 7 to provide gaseous communication between one or more pores of the porous material 10 and the damaged spinal cord tissue 7. The porous material 10 may be sealed in situ proximate the damaged spinal cord tissue 7 to provide a region about the damaged spinal cord tissue 7 for maintaining sub-atmospheric pressure at the damaged spinal cord tissue 7.

In this regard, the muscles 3,4 and subcutaneous tissues may be loosely re-approximated over top of the porous material 10 with the tube 20 exiting through the skin 2 and the skin 2 sutured closed. A further airtight dressing may optionally be placed over the suture site to promote an airtight seal. The porous material 10 may be operably connected with a vacuum system 30 for producing sub-atmospheric pressure at the damaged spinal cord tissue 7, and the vacuum system 30 activated to provide sub-atmospheric pressure at the damaged spinal cord tissue 7. For example, the sub-atmospheric pressure may be maintained at about 25 to 75 mm Hg below atmospheric pressure. The sub-atmospheric pressure may be maintained at the damaged spinal cord tissue 7 for a time sufficient to decrease edema at the spinal cord 7 or to control spinal fluid leaks. In addition, the sub-atmospheric pressure may be maintained at the damaged spinal cord tissue 7 for a time sufficient to prepare the spinal cord tissue 7 to achieve a stage of healing and diminution of bacterial counts such that acceptance of secondary treatments (e.g., flaps, skin grafts) can be successful. The method may be used for at least 4 hours, or can be used for many days. At the end of the vacuum treatment, the sutures 8 may be removed and the skin 2 re-opened. The porous material 10 may then be removed and the skin 2 re-sutured closed.

The method may also include locating a cover 40, 50 over the damaged spinal cord tissue 7 and sealing the cover 40, 50 to tissue proximate the damaged spinal cord tissue 7 for maintaining sub-atmospheric pressure at the damaged spinal cord tissue 7. The step of sealing the cover 40, 50 to tissue surrounding the damaged spinal cord tissue 7 may comprise adhesively sealing and adhering the cover 40, 50 to tissue surrounding the damaged spinal cord tissue 7. The cover 50 may be provided in the form of a self-adhesive sheet 50 which may be located over the damaged spinal cord tissue 7. In such a case, the step of sealing the cover 50 may include adhesively sealing and adhering the self-adhesive sheet 50 to tissue surrounding the damaged spinal cord tissue 7 to form a seal between the sheet 50 and tissue surrounding the damaged spinal cord tissue 7. In addition, the step of operably connecting a vacuum system 30 in gaseous communication with the porous material 10 may comprise connecting the vacuum system 30 with the vacuum port 42 of the cover 40.

EXAMPLES

Rat Spinal Cord Injuries and Sub-Atmospheric Pressure Exposure

Experiment 1

A series of experiments were conducted to determine the effects of sub-atmospheric pressure on the spinal cord in rats post contusion injury. In a first animal protocol, 250-300 gram Sprague Dawley rats were obtained and the model of spinal contusion developed and verified. The procedure for creating the injury and assessing recovery was based upon the description of spinal cord contusion injury in Wrathall, et al., Spinal Cord Contusion in the Rat: Production of Graded, Reproducible, Injury Groups, *Experimental Neurology* 88, 108-122 (1985). The surgical technique was developed for exposing the spinal cord in the anesthetized rats and consistent production of a contusion injury by dropping a cylindrical 10 gram weight through a glass tube from a height of 5 cm. Half of the rats were untreated controls while the other half had the area of contusion exposed to 4 hours of sub-atmospheric pressure (25 mm Hg below atmospheric). However, the degree of injury did not produce a significant injury in the control animals (they recovered quickly), and thus it was not possible to compare the treated animals to the control animals.

Experiment 2

A second protocol was developed in which a more severe injury was inflicted on the spinal cord (a 10 gram weight was dropped from a higher height—7.5 cm). Twenty-eight large (300 gram) Sprague Dawley rats were procured over time and allowed to acclimate to housing conditions. On the day of surgery, the animals were sedated and the back shaved and scrubbed for surgery. A midline incision made over the spine was made extending through the skin and subcutaneous tissue and the cutaneous maximus muscle and fascia exposing the deeper back muscles. The paired muscles that meet at the midline (trapezius and potentially latisimus dorsi) were separated at the midline and retracted laterally. The deep 'postural' muscles such as the spinotrapezius and/or the sacrospinal muscles that are attached to the bony structures of the spine itself were also divided on the midline and retracted laterally. This exposed the spinous process and potentially some of the transverse processes. At the level of T7-T9, the spinous processes and the small transversospinal muscles that extend between two consecutive vertebra were removed, exposing the surface (dura) of the spinal cord. A laminectomy was performed at T-8. The spine was stabilized at T-7 and T-9 and a 10 gram weight was dropped from a height of 7.5 cm to produce a moderate degree of spinal cord injury based on the procedure of Wrathall, et al. Five animals died on their respective day of initial surgery (three in the control group and two in the vacuum treated group), and early in the experiment one animal in the control group died two days into the experiment, leaving 22 animals. By the end of the experiment, eleven animals had been assigned randomly to each of the control group and the 25 mm Hg vacuum group.

For the control rats, no treatment was provided, and the injury was sutured closed. For the vacuum treated rats, a polyvinyl alcohol vacuum dressing (Vacuseal Plus, Polymedics, Belgium) was placed on the cord and the skin sutured closed, with the vacuum tube extending through the incision. After 1 hour delay, a vacuum (sub-atmospheric pressure) of 25 mm Hg below atmospheric pressure was applied for 4 hours to each animal in the vacuum treatment group. At the end of this time, the animals were re-sedated, the vacuum dressings removed, and the skin incision re-sutured with monofilament suture.

The incision sites were inspected daily. The animals were examined for signs of ability to self void their bladders. Any animal unable to void received manual assistance three times per day at 8 hour intervals. The animals were examined daily for signs of auto-cannibalism, pressure sores, and for degree of hydration (pinch test). The animals were housed in soft shavings to minimize potential for pressure sore development. Food was placed on the bottom of cages to facilitate eating. Animals were examined daily for recovery of motor function of hind limbs using a modified Tarlov scoring system for each hind limb. (0=no movement, no weight bearing; 1=slight movement, no weight bearing; 2=frequent movement, no weight bearing; 3=weight bearing, 1-2 steps; 4=walking with deficit; 5=walking with no deficit.) The animals were tested daily on an inclined plane (angle at which they can no longer hold on and slide off the plane), and for hind limb grip strength. The animals were euthanized 14 days post surgery, and the spines removed and examined histologically.

The results of the experiment are provided in Tables 1 and 2, with day "0" being the day of surgery. Several animals exhibited minimal injury/deficit and may not have had an adequate injury during weight drop. (Control animals 1, 2, 11 and treated animals 3, 9, 10. See Tables 1 and 2.) Two animals exhibited a severe/total injury and did not recover. (Control animal 5 and treated animal 2. See Tables 1 and 2.) This left a total of seven control and seven treated animals believed to have an adequate injury but not a severe/total injury.

For purposes of analysis, an animal was considered "recovered" as of the day on which it achieved a score of at least "4/4." Of the seven control animals, three had not recovered to at least a score of 4/4 (right leg/left leg—walking with deficit) by day eight post surgery. (Animals 3, 6, 7. Table 1.) Of the remaining four control animals (animals 4, 8, 9, 10), three animals reached a score of 4/4 on days 4, 6, and 13, and one reached a score of 4/5 on day 7. Thus, the four control animals reached a score of at least 4/4 in a mean of 7.5+/−3.35 days. For the treated animals, all seven (animals 1, 4, 5, 6, 7, 8, 11) reached a score of at least 4/4 in a mean of 5.14+/−1.24 days. Thus it is evident that application of 25 mm Hg vacuum to the injured spine was able to increase the rate of functional recovery ($p=0.059$).

TABLE 1

Control

| Animal | Time Post Surgery (days) | | | | | | | | |
|---|---|---|---|---|---|---|---|---|---|
| | 0 | 1 | 2 | 3 | 4 | 5 | 6 | 7 | 8 | 13 |
| 1 | 5/5 | 5/5 | 5/5 | 5/5 | 5/5 | 5/5 | 5/5 | 5/5 | 5/5 | |
| 2 | 5/4 | 5/4 | 5/4 | 5/4 | 5/4 | 5/4 | 5/4 | 5/4 | 5/4 | |
| 3 | 0/0 | 0/0 | 1/1 | 1/1 | 2/1 | 2/1 | 2/2 | 3/2 | 3/2 | |
| 4 | 2/2 | 2/2 | 3/3 | 3/3 | 4/4 | 4/4 | 4/4 | 5/4 | 5/4 | |
| 5 | 1/0 | 1/0 | 1/0 | 1/0 | 1/1 | 1/1 | 1/1 | 1/1 | 1/1 | |
| 6 | 0/0 | 0/0 | 1/0 | 1/0 | 1/1 | 2/1 | 2/2 | 3/2 | 3/2 | |
| 7 | 0/1 | 0/1 | 1/1 | 1/2 | 1/2 | 2/2 | 2/3 | 3/3 | 3/3 | |
| 8 | 0/0 | 0/0 | 1/1 | 1/1 | 2/2 | 2/2 | 3/3 | 3/3 | 3/3 | 4/4 |
| 9 | 0/0 | 0/0 | 0/1 | 0/1 | 1/2 | 2/2 | 3/4 | 4/5 | | |
| 10 | 0/0 | 0/0 | 1/1 | 1/1 | 1/1 | 1/1 | 4/4 | 4/4 | | |
| 11 | 4/4 | 4/4 | 5/4 | 5/5 | 5/5 | | | | | |

TABLE 2

Vacuum Treated

| Animal | Time Post Surgery (days) | | | | | | | | |
|---|---|---|---|---|---|---|---|---|---|
| | 0 | 1 | 2 | 3 | 4 | 5 | 6 | 7 | 8 | 13 |
| 1 | 1/1 | 1/2 | 1/2 | 2/2 | 3/4 | 4/4 | 4/4 | 4/4 | 4/4 | |
| 2 | 0/0 | 0/0 | 0/0 | 1/0 | 1/0 | 1/0 | 1/1 | 1/1 | 1/1 | |
| 3 | 4/4 | 4/5 | 5/5 | 5/5 | 5/5 | 5/5 | 5/5 | 5/5 | 5/5 | |
| 4 | 0/0 | 2/0 | 2/1 | 3/2 | 3/3 | 4/3 | 4/4 | 5/4 | 5/5 | |
| 5 | 2/1 | 2/1 | 3/2 | 3/3 | 4/4 | 5/5 | 5/5 | 5/5 | 5/5 | |
| 6 | 2/3 | 3/3 | 3/4 | 4/4 | 5/5 | 5/5 | 5/5 | 5/5 | 5/5 | |
| 7 | 1/0 | 1/0 | 1/1 | 2/3 | 3/4 | 4/5 | 5/5 | 5/5 | 5/5 | |

TABLE 2-continued

Vacuum Treated

| Animal | Time Post Surgery (days) | | | | | | | | |
|---|---|---|---|---|---|---|---|---|---|
| | 0 | 1 | 2 | 3 | 4 | 5 | 6 | 7 | 8 | 13 |
| 8 | 1/0 | 1/0 | 2/1 | 3/2 | 3/2 | 3/2 | 4/3 | 5/4 | 5/4 | 5/4 |
| 9 | 3/4 | 5/5 | 4/4 | 5/5 | 5/5 | | | | | |
| 10 | 4/4 | 4/4 | 4/4 | 5/5 | 5/5 | | | | | |
| 11 | 0/0 | 0/0 | 1/1 | 2/2 | 3/3 | 3/3 | 4/4 | 4/4 | | |

Experiment 3

An additional protocol was developed in which a still more severe injury was created that would result in a non-recoverable (permanent) functional deficit. The contusion paradigm was based upon techniques developed at the W.M. Keck Center for Collaborative Neuroscience—The Spinal Cord Injury Project using the NYU spinal cord contusion system. These systems (currently named "MASCIS") are custom built and are available commercially through the Biology Department at Rutgers University (W. M. Keck Center for Collaborative Neuroscience, Piscataway, N.J.).

In the preceding experiments, animals were operated on depending on weight, but in this experiment the animals were operated on depending on age. Long Evans hooded rats were operated on at 77 days of age to standardize the severity of injury. Between one and six days before surgery, some of the animals were sedated and transported to the Small Animal MRI Imaging Facility of Wake Forest University School of Medicine, and the spinal cord was scanned at the level of T9-T10 using a Bruker Biospin Horizontal Bore 7 Tesla small animal scanner (Ettlingen, Germany). The animals which were scanned were then allowed to recover from anesthesia in a heated cage. On the day of surgery the animals were anesthetized, and the backs of the animals were shaved and a depilatory cream used. Using aseptic technique, a laminectomy was performed at the level of T9-T10. The NYU spinal cord contusion system impactor was used, and the cord was impacted at T9-T10 with a 10 gram rod dropped from a height of 25 mm. Animals in the control group had the incision sutured closed, and the animals were allowed to recover in a heated cage. For treated animals, a polyvinyl alcohol vacuum dressing (VersaFoam, Kinetic Concepts, Inc., San Antonio, Tex.) was placed over the cord, the incision sutured closed, and 25 mm Hg vacuum, i.e. 25 mm Hg below atmospheric pressure, applied for 8 hours. After this time the treated animals were re-sedated, the incision opened, the vacuum dressing removed, and the incision re-sutured closed. If the animals received a post-surgery MRI, the animal was scanned 8 hours post impaction.

Functional recovery was assessed with the BBB scale, a 22 point scale from the W.M. Keck Center for Collaborative Neuroscience. (Table 3). The animals were monitored for 21 days, then euthanized by lethal $CO_2$ exposure. Bladders were expressed daily, and the animals were monitored for signs of auto-cannibalism, pressure sores, skin lesions, etc. Any animal exhibiting signs of auto-cannibalization were removed from the study and euthanized. Pressure sores and skin lesions were treated as appropriate and with consultation of ARP veterinary staff. Despite this care, in the course of this experiment, some animals died, while others were excluded for other problems.

TABLE 3

BBB Locomotor Rating Scale

Value  Condition

Figure 6:
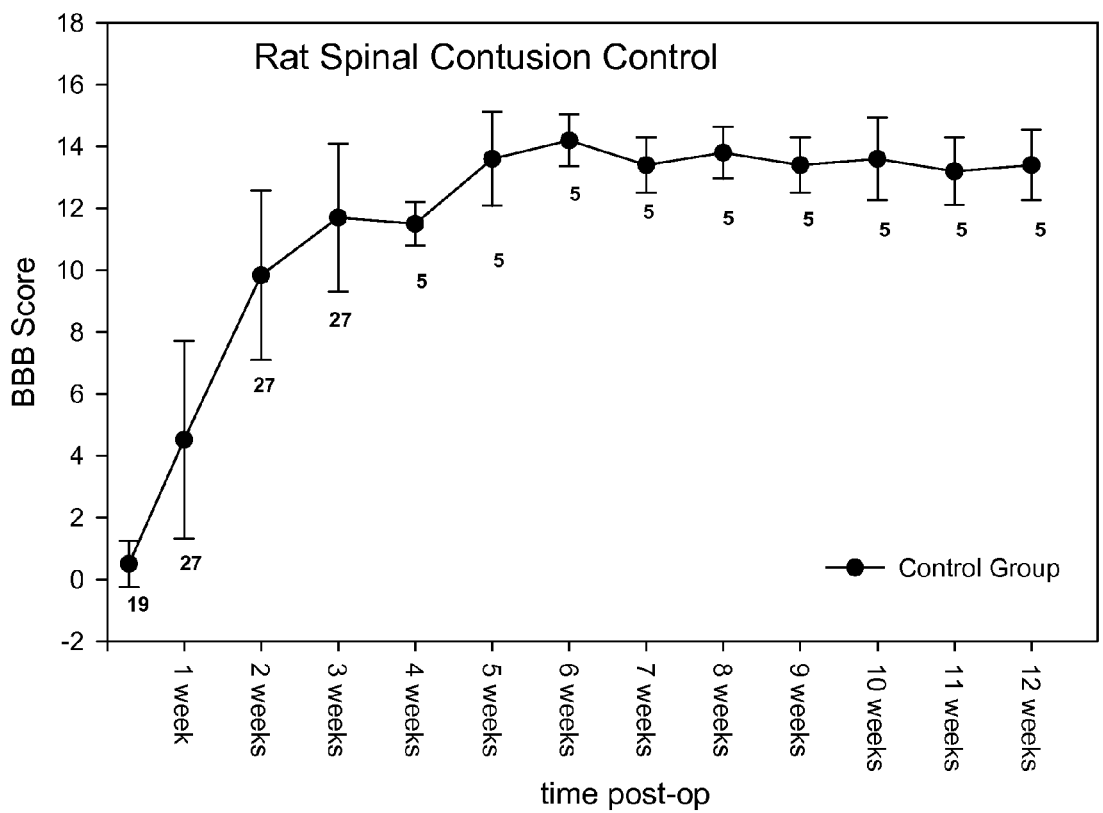
FIG. 6 illustrates the BBB score as a function of time for control animals exposed to recoverable blunt trauma of the spinal cord.
Figure 7:
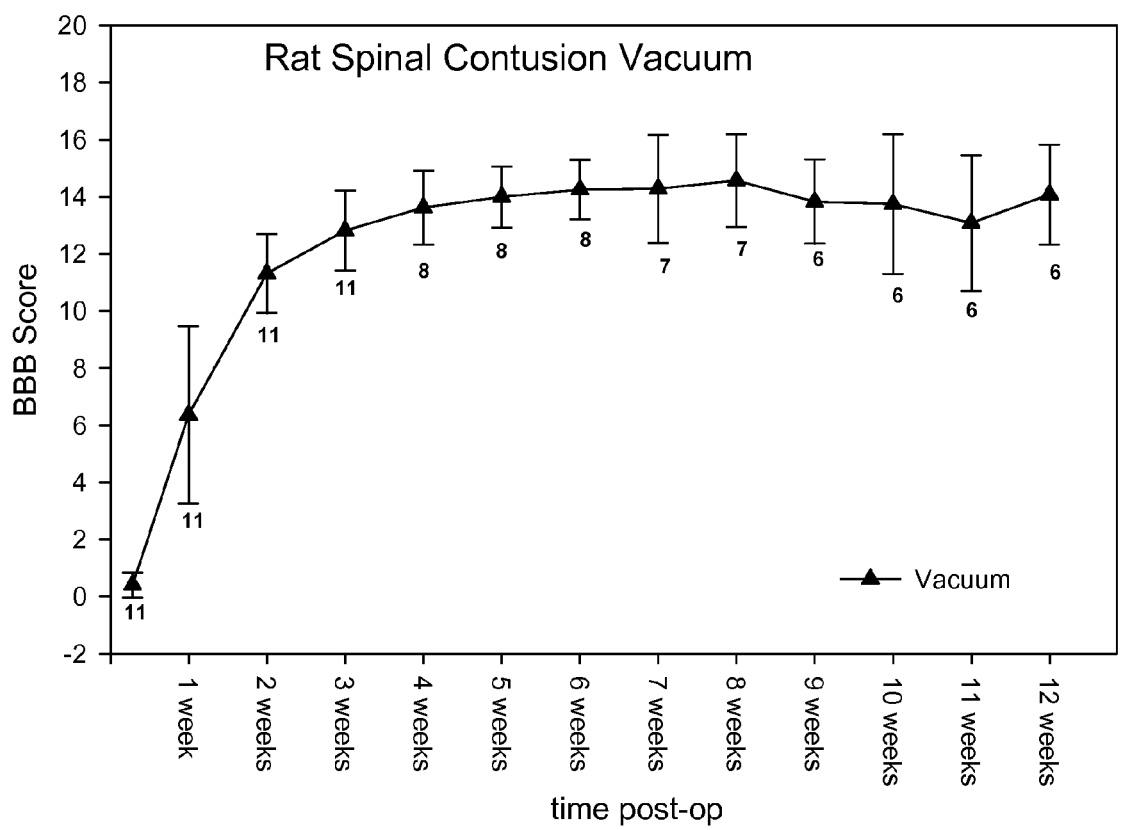
FIG. 7 illustrates the BBB score as a function of time for animals exposed to recoverable blunt trauma of the spinal cord and treated with sub-atmospheric pressure.

0   No observable hind limb (HL) movement
1   Slight Movement of one or two joints, usually the hip &/or knee
2   Extensive movement of one joint or Extensive movement of one joint and slight movement of one other joint
3   Extensive movement of two joints
4   Slight movement of all three joints of the HL
5   Slight movement of two joints and extensive movement of the third
6   Extensive movement of two joints and slight movement of the third
7   Extensive movement of all three joints of the HL
8   Sweeping with no weight support or Plantar placement of the paw with no weight support
9   Plantar placement of the paw with weight support in stance only (i.e. when stationary) or Occasional, Frequent, or Consistent weight supported dorsal stepping and no plantar stepping
10  Occasional weight supported plantar; no front limb (FL)-HL coordination
11  Frequent to consistent weight supported plantar steps and no FL-HL coordination
12  Frequent to consistent weight supported plantar steps and occasional FL-HL coordination
13  Frequent to consistent weight supported plantar steps and frequent FL-HL coordination
14  Consistent weight supported plantar steps, consistent FL-HL coordination and Predominant paw position during locomotion is rotated (internally or externally) when it makes initial contact with the surface as well as just before it is lifted off at the end of stance or Frequent plantar stepping; consistent FL-HL coordination; and occasional dorsal stepping
15  Consistent plantar stepping and Consistent FL-HL coordination; and No toe clearance or occasional toe clearance during forward limb advancement; Predominant paw position is parallel to the body at initial contact
16  Consistent plantar stepping and Consistent FL-HL coordination during gait; and Toe clearance occurs frequently during forward limb advancement; Predominant paw position is parallel at initial contact and rotated at lift off
17  Consistent plantar stepping and Consistent FL-HL coordination during gait; and Toe clearance occurs frequently during forward limb advancement; Predominant paw position is parallel at initial contact and lift off
18  Consistent plantar stepping and Consistent FL-HL coordination during gait; and Toe clearance occurs consistently during forward limb advancement; Predominant paw position is parallel at initial contact and rotated at lift off
19  Consistent plantar stepping and Consistent FL-HL coordination during gait; and Toe clearance occurs consistently during forward limb advancement; Predominant paw position is parallel at initial contact and lift off; and tail is down part or all of the time
20  Consistent plantar stepping and Consistent coordinated gait; consistent toe clearance' Predominant paw position is parallel at initial contact and lift off; and Trunk instability; Tail consistently up
21  Consistent plantar stepping and Consistent coordinated gait; consistent toe clearance; predominant paw position is parallel throughout stance; consistent trunk stability; tail consistently up For these studies of a permanent injury, 36 rats with the dura intact completed the study and were analyzed. Eleven (11) vacuum treated animals started the study, with one animal removed at five weeks and one at eight weeks due to urinary tract infections and kidney failure. Thus, 9 vacuum treated animals completed the 12 week study. Twenty seven control animals started and completed the study. The vacuum treated animals exhibited a greater functional recovery ($p<0.072$) at 3 weeks post injury: BBB Score=12.818+/−1.401 (n=1) vacuum treated versus 11.704+/−2.391 (n=27) control. The vacuum treated animals exhibited a significantly greater functional recovery ($p<0.001$) at 4 weeks post injury: BBB Score=13.625+/−1.303 (n=1) vacuum treated versus 11.500+/−0.707 control (n=27). FIGS. 6 and 7. The recovery of the vacuum treated animals plateaued, and the recovery levels of the control animals gradually approached the level of the vacuum treated animals. FIGS. 6 and 7. (Note, some animals were studied for three weeks (generally earlier in the study) while some were observed for 12 weeks for functional recovery.)

In addition to the BBB assessments, two animals with intact dura were analyzed for a change in the cross sectional area (e.g., in $mm^2$) of the spinal cord by pre- and post-injury MRI scans (with the post-injury scan performed post-treatment for the vacuum treated animals) using the procedures listed above for this experiment. Of the four animals produced for this analysis, only one vacuum treated animal did not have any technical or impaction error and could be used. Of the control animals, one had a minor height error which occurred when the release pin of the spinal cord contusion system was pulled from its housing; all other control animals had significant impaction errors which precluded analysis of the cross sectional area of the spinal cord. The machine recorded height from which the weight was dropped for the vacuum treated rat was 24.8 mm and for the control rat was 25.782 mm.

Figure 8:
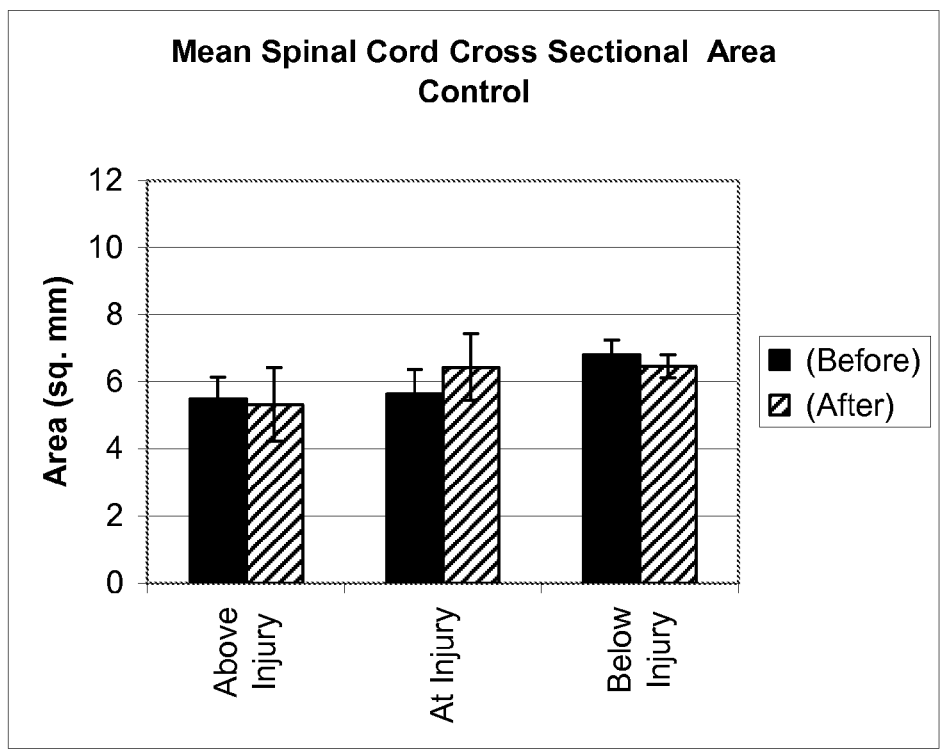
FIG. 8 illustrates the cross-sectional area of the spinal cord as a function of time for control animals exposed to non-recoverable blunt trauma of the spinal cord.

Turning to FIG. 8, the control animal showed a slight increase in cross sectional area as the scans went down (tailward) the spine. This was evident for both the pre-impaction scan and the post-impaction scan. At both the above-injury and below-injury sites, the cross sectional area was not significantly different between the pre-impaction scan and the post-impaction scan. The above-injury pre-impaction mean was 5.49 $mm^2$+/−0.2 (n=5) versus a post impaction mean of 5.32 mm²+/−0.23 (n=4): p<0.211) (The below-injury pre-impaction mean was 6.81 mm²+/−0.25 (n=3) versus a post-impaction mean of 6.46 mm²+/−0.78 (n=4): p<0.464) However, at the site of impaction, the post-impaction cross sectional area for the control animal was significantly larger (p<0.001) than the pre-impaction cross sectional area: mean of pre-impaction area of 5.63 mm²+/−0.24 (n=5 scans) versus mean post-impaction area of 6.43 mm²+/−0.32 (n=4 scans). This was most likely due to swelling of the cord due to the limits of the dura, as the bone which would be the limiting factor on diameter of the cord had been removed.

Figure 9:
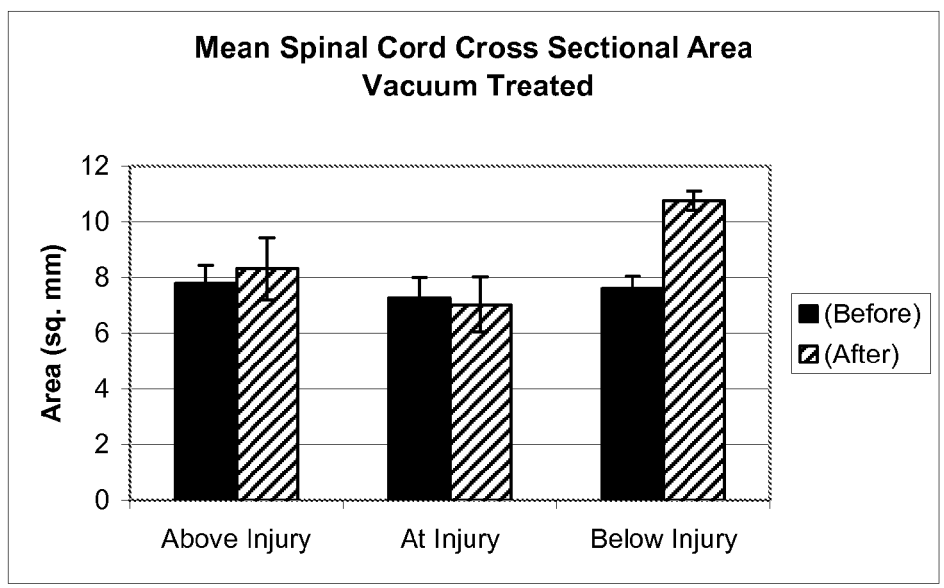
FIG. 9 illustrates the cross-sectional area of the spinal cord as a function of time for animals exposed to non-recoverable blunt trauma of the spinal cord and treated with sub-atmospheric pressure.

Unlike the control animal, the vacuum treated animal did not show an increase in mean diameter of the cord at the site of the injury after vacuum treatment, FIG. 9. The mean pre-impaction area at the level of the injury was 7.28 mm²+/−0.73 (n=4 scans) versus a mean post-treatment area of 7.03 mm²+/−0.99 (n=4 scans) (p<0.73). The similarity in the size of the spinal cord pre-impaction and post-treatment at the site of the injury was most likely due to removal of fluid from within the dura, thus maintaining the initial diameter of the cord.

The pre-impaction and post-treatment scans at the above-injury area were similar (not significantly different). The pre-impaction above-injury area was 7.79+/−0.64 (n=3 scans) versus post-treatment of 8.33+/−1.11 (n=5 scans) (p<0.48). For the scans of the vacuum treated animal below-injury, the post-treatment cross sectional area of the cord was significantly larger than the pre-impaction cross sectional area: Pre-impaction area of 7.61+/−0.43 (n=4 scans) versus post-treatment area of 10.76+/−0.35 (n=4 scans), p<0.001. A possible explanation for the increase in below-injury cross sectional area of the cord may be attributable to venous congestion. Alternatively, the applied vacuum may have actively withdrawn cerebrospinal fluid from around the cord, allowing the cord to expand to fill the area of the spinal canal within the vertebral bodies. This expansion would act to minimize the intra-dura pressure and help to preserve cell viability.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A method for treating damaged spinal cord tissue using sub-atmospheric pressure, comprising:
   i. locating a porous material proximate the damaged spinal cord tissue to provide gaseous communication between one or more pores of the porous material and the damaged spinal cord tissue;
   ii. sealing porous material in situ proximate the damaged spinal cord tissue to provide a region about the damaged spinal cord tissue for maintaining sub-atmospheric pressure at the damaged spinal cord tissue;
   iii. operably connecting a vacuum system in gaseous communication with the porous material for producing sub-atmospheric pressure at the damaged spinal cord tissue; and
   iv. activating the vacuum system to provide sub-atmospheric pressure at the damaged spinal cord tissue.

2. The method for treating damaged spinal cord tissue according to claim 1, wherein the step of locating a porous material comprises locating a porous material that comprises, at least at a selected surface of the porous material, pores sufficiently small to prevent the growth of tissue therein.

3. The method for treating damaged spinal cord tissue according to claim 1, wherein the step of locating a porous material comprises locating a porous material that comprises, at least at a selected surface of the porous material, a pore size smaller than the size of fibroblasts.

4. The method for treating damaged spinal cord tissue according to claim 2 or 3, wherein the selected surface is disposed proximate the interface with the damaged spinal cord tissue.

5. The method for treating damaged spinal cord tissue according to any one of claims 1-3, wherein the step of locating a porous material comprises locating a porous material that comprises a pore size sufficiently large to promote the formation of granulation tissue at other tissues in the spaces surrounding the damaged spinal cord tissue.

6. The method for treating damaged spinal cord tissue according to any one of claims 1-3, wherein the step of locating a porous material comprises locating a porous, open-cell collagen material proximate the damaged spinal cord tissue.

7. The method for treating damaged spinal cord tissue according to any one of claims 1-3, wherein the step of locating a porous material comprises locating a porous, bio-incorporable material proximate the damaged spinal cord tissue.

8. The method for treating damaged spinal cord tissue according to any one of claims 1-3, wherein the step of locating a porous material comprises locating a porous, electrospun material proximate the damaged spinal cord tissue.

9. The method for treating damaged spinal cord tissue according to any one of claims 1-3, wherein the step of locating a porous material comprises locating a porous, cast material proximate the damaged spinal cord tissue.

10. The method for treating damaged spinal cord tissue according to any one of claims 1-3, wherein the step of locating a porous material comprises locating a porous, printed material proximate the damaged spinal cord tissue.

11. The method for treating damaged spinal cord tissue according to any one of claims 1-3, wherein the step of locating a porous material comprises locating a polyglycolic and/or polylactic acid material proximate the damaged spinal cord tissue.

12. The method for treating damaged spinal cord tissue according to any one of claims 1-3, wherein the step of locating a porous material comprises locating a polydiolcitrate material proximate the damaged spinal cord tissue.

13. The method for treating damaged spinal cord tissue according to any one of claims 1-3, wherein the step of locating a porous material comprises locating a material comprising polydiolcitrate and collagen proximate the damaged spinal cord tissue.

14. The method for treating damaged spinal cord tissue according to any one of claims 1-3, wherein the step of locating a porous material comprises locating at least one of a foam, a polyvinyl alcohol foam, and an open-cell polymer foam proximate the damaged spinal cord tissue.

15. The method for treating damaged spinal cord tissue according to any one of claims 1-3, wherein the step of locating a porous material comprises locating at least one of a porous sheet and a flexible, sheet-like mesh proximate the damaged spinal cord tissue.

16. The method for treating damaged spinal cord tissue according to any one of claims 1-3, wherein the step of locating a porous material comprises locating a polyethylene and/or polyester material proximate the damaged spinal cord tissue.

17. The method for treating damaged spinal cord tissue according to any one of claims 1-3, wherein the step of locating a porous material comprises locating a material comprising elastin, hyaluronic acid, alginates, or combinations thereof proximate the damaged spinal cord tissue.

18. A method for treating damaged spinal cord tissue according to claim 1, comprising maintaining the sub-atmospheric pressure at the damaged spinal cord for a time sufficient to decrease edema at the spinal cord.

19. The method for treating damaged spinal cord tissue according to claim 1, comprising maintaining a sub-atmospheric pressure of about 25 mm Hg below atmospheric pressure.

20. The method for treating damaged spinal cord tissue according to claim 1, comprising maintaining a sub-atmospheric pressure of at least about 25 mm Hg below atmospheric pressure.

21. The method for treating damaged spinal cord tissue according to claim 1, comprising maintaining sub-atmospheric pressure of between about 25 and 75 mm Hg below atmospheric pressure at the damaged spinal cord tissue.

22. The method for treating damaged spinal cord tissue according to claim 1, wherein the step of sealing porous material in situ comprises locating a cover over damaged spinal cord tissue and sealing the cover to tissue proximate the damaged spinal cord tissue for maintaining sub-atmospheric pressure at the damaged spinal cord tissue.

23. The method for treating damaged spinal cord tissue according to claim 22, wherein the cover comprises a vacuum port for receiving sub-atmospheric pressure from the vacuum system, and wherein the step of operably connecting a vacuum system in gaseous communication with the porous material comprising connecting the vacuum system with the vacuum port.

24. The method for treating damaged spinal cord tissue according to claim 22, wherein the step of sealing the cover to tissue surrounding the damaged spinal cord tissue comprises adhesively sealing and adhering the cover to tissue surrounding the damaged spinal cord tissue.

25. The method for treating damaged spinal cord tissue according to claim 22, wherein the step of locating a cover comprises locating a self-adhesive sheet over the damaged spinal cord tissue, and wherein the step of sealing the cover comprises adhesively sealing and adhering the self-adhesive sheet to tissue surrounding the damaged spinal cord tissue to form a seal between the sheet and tissue surrounding the damaged spinal cord tissue.

* * * * *